United States Patent [19]
Lal et al.

[11] Patent Number: 6,060,250
[45] Date of Patent: May 9, 2000

[54] HUMAN TRANSFERASES

[75] Inventors: Preeti Lal, Santa Clara; Olga Bandman; Jennifer L. Hillman, both of Mountain View; Karl J. Guegler, Menlo Park; Gina A. Gorgone, Boulder Creek; Neil C. Corley; Chandra Patterson, both of Mountain View, all of Calif.

[73] Assignee: Incyte Pharmaceuticals, Inc., Palo Alto, Calif.

[21] Appl. No.: 09/109,204

[22] Filed: Jun. 30, 1998

[51] Int. Cl.$^7$ .............................. C12N 15/54; C12N 9/10; C12Q 1/68
[52] U.S. Cl. ........................... 435/6; 435/193; 435/252.3; 435/325; 435/320.1; 536/23.1; 536/23.2
[58] Field of Search .................................. 536/23.1, 23.2; 435/6, 193, 252.3, 325, 320.1

[56] References Cited

PUBLICATIONS

GenBank entry AA203508, Jan. 1997.
GenBank entry F11219, Sep. 1995.
GenBank entry W95847, Nov. 1996.
GenBank entry AA232780, Feb. 1997.
GenBank entry AA401238, May 1997.
GenBank entry AA404282, May 1997.
GenBank entry AA449047, Jun. 1997.
GenBank entry AA677466, Dec. 1997.
GenBank entry AA772088, Jan 1998
ExPASy Enzyme: EC 2.6.1.64.
Perry, S.J. et al., "Isolation and Expression of a cDNA Coding for Rat Kidney Cystosolic Cysteine conjugate β–Lyase", *Pharmacol.*, 43: 660–665 (1993).
Perry, S., et al., "Molecular cloning and expression of a cDNA for human kidney cysteine conjugate β–lyase", *FEBS Lett.*, 360: 277–280 (1995).
Alberati–Giani, D. et al., "Cloning and Characterization of a Soluble Kynurenine Aminotransferase from Rat Brain: Identity with Kidney Cysteine Conjugate β–Lyase", *J. Neurochem.*, 64: 1448–1455 (1995).
Nakatani, Y. et al., "α–Aminoadipate Aminotransferase of Rat Liver Mitochondria", *Biochim. Biophys. Acta.*, 198: 219–228 (1970).
Buchli, R. et al., "Cloning and Functional Expression of a Soluble Form of Kynurenine/α–Aminoadipate Aminotransferase from Rat Kidney", *J. Biol. Chem.*, 270: 29330–29335 (1995).
Lin, W.J. et al., "The Mammalian Immediate–early TIS21 Protein and the Leukemia–associated BTG1 Protein Interact with a Protein–arginine N–Methyltransferase", *J. Biol. Chem.*, 271: 15034–15044 (1996).
Abramovich, C. et al., "A protein–arginine methyltransferase binds the intracytoplasmic domain of the IFNAR1 chain in the type I interferon receptor", *EMBO J.*, 16: 260–266 (1997).
Scott, H.S., et al., "Identification and Characterization of Two Putative Human Arginine Methyltransferases (HRMT1L1 and HRMT1L2)", *Genomics*, 48: 330–340 (1998).
Cooper, A.J.L. and A. Meister, "Glutamine Transminase K from Rat Kidney", *Meth. Enzymol.*, 113: 344–349 (1985).
Perry, S. et al., (Direct Submission), GenBank Sequence Database (Accession X82224), National Center for Biotechnology Information, National Library of Medicine, Bethesda, Maryland, 20894, (GI 758590; GI 758591).
Buchli, R. et al., (Direct Submission), GenBank Sequence Database (Accession Z50144), National Center for Biotechnology Information, National Library of Medicine, Bethesda, Maryland, 20894, (GI 1050751; GI 1050752).
Scott, H.S. et al., (Direct Submission), GenBank Sequence Database (Acession Y10807), National Center for Biotechnology Information, National Library of Medicine, Bethesda, Maryland, 20894, (GI 1808647; GI 1808648).

*Primary Examiner*—Rebecca E. Prouty
*Attorney, Agent, or Firm*—Colette C. Muenzen; Incyte Pharmaceuticals, Inc.

[57] ABSTRACT

The invention provides three human transferases (HUTRAN) and polynucleotides which identify and encode HUTRAN. The invention also provides expression vectors, host cells, antibodies, agonists, and antagonists. The invention also provides methods for diagnosing, treating or preventing disorders associated with expression of HUTRAN.

10 Claims, 7 Drawing Sheets

| Pos | Sequence | ID |
|---|---|---|
| 200 | E A K E G D L H R I E I P F K F H M L H S G L V H G L A F W | 2525071 |
| 231 | T V K V E D L T - F T S P F C L Q V K R N D Y V H A L V A Y | GI 1808648 |
| 230 | F D V A F I G S I M T V W L S T A P T E P L T H W Y Q V R C | 2525071 |
| 260 | F N I E F T R C H K R T G F S T S P E S P Y T H W K Q T V F | GI 1808648 |
| 260 | L F Q S P L F A K A G D T L S G T C L L I A N K R Q S Y D I | 2525071 |
| 290 | Y M E D Y L T V K T G E E I F G T I G M R P N A K N N R D L | GI 1808648 |
| 290 | S I V A Q V D Q T G S K S S N L L D L K N P F F R Y T G T T | 2525071 |
| 320 | D F T I D - - - - - - - - L D F K G Q L - - - - - - - - - | GI 1808648 |
| 320 | P S P P P G S H Y T S P S E N M W N T G S T Y N L S S G M A | 2525071 |
| 332 | - - - - - - - - - - - - - - - - - - - - - - - - - - - - - | GI 1808648 |
| 350 | V A G M P T A Y D L S S V I A S G S S V G H N N L I P L A N | 2525071 |
| 332 | - - - - - - - - - C E L S C - - - - - - - - - - - - - - - | GI 1808648 |
| 380 | T G I V N H T H S R M G S I M S T G I V Q G S S G A Q G S G | 2525071 |
| 337 | - - - - - - - - - - - - - - - - - - - - - - - - - - - - - | GI 1808648 |
| 410 | G G S T S A H Y A V N S Q F T M G G P A I S M A S P M S I P | 2525071 |
| 337 | - - - - - - - - - S T D Y R M - - - - - - - - - - - - - - | GI 1808648 |

SEQUENCE LISTING (1) GENERAL INFORMATION:

(iii) NUMBER OF SEQUENCES: 32

(2) INFORMATION FOR SEQ ID NO: 1:

(i) SEQUENCE CHARACTERISTICS:
        (A) LENGTH: 454 amino acids
        (B) TYPE: amino acid
        (C) STRANDEDNESS: single
        (D) TOPOLOGY: linear (vii) IMMEDIATE SOURCE:
        (A) LIBRARY: PROSNOT20
        (B) CLONE: 1815528

(xi) SEQUENCE DESCRIPTION: SEQ ID NO: 1:

```
Met Phe Leu Ala Gln Arg Ser Leu Cys Ser Leu Ser Gly Arg Ala
                  5                  10                  15

Lys Phe Leu Lys Thr Ile Ser Ser Lys Ile Leu Gly Phe Ser
                 20                  25                  30

Thr Ser Ala Lys Met Ser Leu Lys Phe Thr Asn Ala Lys Arg Ile
                 35                  40                  45

Glu Gly Leu Asp Ser Asn Val Trp Ile Glu Phe Thr Lys Leu Ala
                 50                  55                  60

Ala Asp Pro Ser Val Val Asn Leu Gly Gln Gly Phe Pro Asp Ile
                 65                  70                  75

Ser Pro Pro Thr Tyr Val Lys Glu Glu Leu Ser Lys Ile Ala Ala
                 80                  85                  90

Ile Asp Ser Leu Asn Gln Tyr Thr Arg Gly Phe Gly His Pro Ser
                 95                 100                 105

Leu Val Lys Ala Leu Ser Tyr Leu Tyr Glu Lys Leu Tyr Gln Lys
                110                 115                 120

Gln Ile Asp Ser Asn Lys Glu Ile Leu Val Thr Val Gly Ala Tyr
                125                 130                 135

Gly Ser Leu Phe Asn Thr Ile Gln Ala Leu Ile Asp Glu Gly Asp
                140                 145                 150

Glu Val Ile Leu Ile Val Pro Phe Tyr Asp Cys Tyr Glu Pro Met
                155                 160                 165

Val Arg Met Ala Gly Ala Thr Pro Val Phe Ile Pro Leu Arg Ser
                170                 175                 180

Lys Pro Val Tyr Gly Lys Arg Trp Ser Ser Asp Trp Thr Leu
                185                 190                 195

Asp Pro Gln Glu Leu Glu Ser Lys Phe Asn Ser Lys Thr Lys Ala
                200                 205                 210

Ile Ile Leu Asn Thr Pro His Asn Pro Leu Gly Lys Val Tyr Asn
                215                 220                 225

Arg Glu Glu Leu Gln Val Ile Ala Asp Leu Cys Ile Lys Tyr Asp
                230                 235                 240

Thr Leu Cys Ile Ser Asp Glu Val Tyr Glu Trp Leu Val Tyr Ser
                245                 250                 255

Gly Asn Lys His Leu Lys Ile Ala Thr Phe Pro Gly Met Trp Glu
                260                 265                 270

Arg Thr Ile Thr Ile Gly Ser Ala Gly Lys Thr Phe Ser Val Thr
                275                 280                 285
```

-continued

```
Gly Trp Lys Leu Gly Trp Ser Ile Gly Pro Asn His Leu Ile Lys
            290                 295                 300

His Leu Gln Thr Val Gln Gln Asn Thr Ile Tyr Thr Cys Ala Thr
            305                 310                 315

Pro Leu Gln Glu Ala Leu Ala Gln Ala Phe Trp Ile Asp Ile Lys
            320                 325                 330

Arg Met Asp Asp Pro Glu Cys Tyr Phe Asn Ser Leu Pro Lys Glu
            335                 340                 345

Leu Glu Val Lys Arg Asp Arg Met Val Arg Leu Leu Glu Ser Val
            350                 355                 360

Gly Leu Lys Pro Ile Val Pro Asp Gly Gly Tyr Phe Ile Ile Ala
            365                 370                 375

Asp Val Ser Leu Leu Asp Pro Asp Leu Ser Asp Met Lys Asn Asn
            380                 385                 390

Glu Pro Tyr Asp Tyr Lys Phe Val Lys Trp Met Thr Lys His Lys
            395                 400                 405

Lys Leu Ser Ala Ile Pro Val Ser Ala Phe Cys Asn Ser Glu Thr
            410                 415                 420

Lys Ser Gln Phe Glu Lys Phe Val Arg Phe Cys Phe Ile Lys Lys
            425                 430                 435

Asp Ser Thr Leu Asp Ala Ala Glu Glu Ile Ile Lys Ala Trp Ser
            440                 445                 450

Val Gln Lys Ser
```

(2) INFORMATION FOR SEQ ID NO: 2:

(i) SEQUENCE CHARACTERISTICS:
        (A) LENGTH: 425 amino acids
        (B) TYPE: amino acid
        (C) STRANDEDNESS: single
        (D) TOPOLOGY: linear (vii) IMMEDIATE SOURCE:
        (A) LIBRARY: BRAINOT09
        (B) CLONE: 2150892

(xi) SEQUENCE DESCRIPTION: SEQ ID NO: 2:

```
Met Asn Tyr Ala Arg Phe Ile Thr Ala Ala Ser Ala Arg Arg Asn
              5                  10                  15

Pro Thr Pro Ile Arg Thr Met Thr Asp Ile Leu Ser Arg Gly Pro
             20                  25                  30

Lys Ser Met Ile Ser Leu Ala Gly Gly Leu Pro Asn Pro Asn Met
             35                  40                  45

Phe Pro Phe Lys Thr Ala Val Ile Thr Val Glu Asn Gly Lys Thr
             50                  55                  60

Ile Gln Phe Gly Glu Glu Met Met Lys Arg Ala Leu Gln Tyr Ser
             65                  70                  75

Pro Ser Ala Gly Ile Pro Glu Leu Leu Ser Trp Leu Lys Gln Leu
             80                  85                  90

Gln Ile Lys Leu His Asn Pro Pro Thr Ile His Tyr Pro Pro Ser
             95                 100                 105

Gln Gly Gln Met Asp Leu Cys Val Thr Ser Gly Ser Gln Gln Gly
            110                 115                 120

Leu Cys Lys Val Phe Glu Met Ile Ile Asn Pro Gly Asp Asn Val
            125                 130                 135

Leu Leu Asp Glu Pro Ala Tyr Ser Gly Thr Leu Gln Ser Leu His
            140                 145                 150
```

-continued

```
Pro Leu Gly Cys Asn Ile Ile Asn Val Ala Ser Asp Glu Ser Gly
            155                 160                 165

Ile Val Pro Asp Ser Leu Arg Asp Ile Leu Ser Arg Trp Lys Pro
            170                 175                 180

Glu Asp Ala Lys Asn Pro Gln Lys Asn Thr Pro Lys Phe Leu Tyr
            185                 190                 195

Thr Val Pro Asn Gly Asn Asn Pro Thr Gly Asn Ser Leu Thr Ser
            200                 205                 210

Glu Arg Lys Lys Glu Ile Tyr Glu Leu Ala Arg Lys Tyr Asp Phe
            215                 220                 225

Leu Ile Ile Glu Asp Asp Pro Tyr Tyr Phe Leu Gln Phe Asn Lys
            230                 235                 240

Phe Arg Val Pro Thr Phe Leu Ser Met Asp Val Asp Gly Arg Val
            245                 250                 255

Ile Arg Ala Asp Ser Phe Ser Lys Ile Ile Ser Ser Gly Leu Arg
            260                 265                 270

Ile Gly Phe Leu Thr Gly Pro Lys Pro Leu Ile Glu Arg Val Ile
            275                 280                 285

Leu His Ile Gln Val Ser Thr Leu His Pro Ser Thr Phe Asn Gln
            290                 295                 300

Leu Met Ile Ser Gln Leu Leu His Glu Trp Gly Gly Glu Gly Phe
            305                 310                 315

Met Ala His Val Asp Arg Val Ile Asp Phe Tyr Ser Asn Gln Lys
            320                 325                 330

Asp Ala Ile Leu Ala Ala Asp Lys Trp Leu Thr Gly Leu Ala
            335                 340                 345

Glu Trp His Val Pro Ala Ala Gly Met Phe Leu Trp Ile Lys Val
            350                 355                 360

Lys Gly Ile Asn Asp Val Lys Glu Leu Ile Glu Lys Ala Val
            365                 370                 375

Lys Met Gly Val Leu Met Leu Pro Gly Asn Ala Phe Tyr Val Asp
            380                 385                 390

Ser Ser Ala Pro Ser Pro Tyr Leu Arg Ala Ser Phe Ser Ser Ala
            395                 400                 405

Ser Pro Glu Gln Met Asp Val Ala Phe Gln Val Leu Ala Gln Leu
            410                 415                 420

Ile Lys Glu Ser Leu
            425
```

(2) INFORMATION FOR SEQ ID NO: 3:

(i) SEQUENCE CHARACTERISTICS:
        (A) LENGTH: 447 amino acids
        (B) TYPE: amino acid
        (C) STRANDEDNESS: single
        (D) TOPOLOGY: linear (vii) IMMEDIATE SOURCE:
        (A) LIBRARY: BRAITUT21
        (B) CLONE: 2525071

(xi) SEQUENCE DESCRIPTION: SEQ ID NO: 3:

```
Met Met Gln Asp Tyr Val Arg Thr Gly Thr Tyr Gln Arg Ala Ile
              5                  10                  15

Leu Gln Asn His Thr Asp Phe Lys Asp Lys Ile Val Leu Asp Val
             20                  25                  30
```

-continued

```
Gly Cys Gly Ser Gly Ile Leu Ser Phe Ala Ala Gln Ala Gly
             35                  40                  45

Ala Arg Lys Ile Tyr Ala Val Glu Ala Ser Thr Met Ala Gln His
             50                  55                  60

Ala Glu Val Leu Val Lys Ser Asn Asn Leu Thr Asp Arg Ile Val
             65                  70                  75

Val Ile Pro Gly Lys Val Glu Glu Val Ser Leu Pro Glu Gln Val
             80                  85                  90

Asp Ile Ile Ile Ser Glu Pro Met Gly Tyr Met Leu Phe Asn Glu
             95                 100                 105

Arg Met Leu Glu Ser Tyr Leu His Ala Lys Lys Tyr Leu Lys Pro
            110                 115                 120

Ser Gly Asn Met Phe Pro Thr Ile Gly Asp Val His Leu Ala Pro
            125                 130                 135

Phe Thr Asp Glu Gln Leu Tyr Met Glu Gln Phe Thr Lys Ala Asn
            140                 145                 150

Phe Trp Tyr Gln Pro Ser Phe His Gly Val Asp Leu Ser Ala Leu
            155                 160                 165

Arg Gly Ala Ala Val Asp Glu Tyr Phe Arg Gln Pro Val Val Asp
            170                 175                 180

Thr Phe Asp Ile Arg Ile Leu Met Ala Lys Ser Val Lys Tyr Thr
            185                 190                 195

Val Asn Phe Leu Glu Ala Lys Glu Gly Asp Leu His Arg Ile Glu
            200                 205                 210

Ile Pro Phe Lys Phe His Met Leu His Ser Gly Leu Val His Gly
            215                 220                 225

Leu Ala Phe Trp Phe Asp Val Ala Phe Ile Gly Ser Ile Met Thr
            230                 235                 240

Val Trp Leu Ser Thr Ala Pro Thr Glu Pro Leu Thr His Trp Tyr
            245                 250                 255

Gln Val Arg Cys Leu Phe Gln Ser Pro Leu Phe Ala Lys Ala Gly
            260                 265                 270

Asp Thr Leu Ser Gly Thr Cys Leu Leu Ile Ala Asn Lys Arg Gln
            275                 280                 285

Ser Tyr Asp Ile Ser Ile Val Ala Gln Val Asp Gln Thr Gly Ser
            290                 295                 300

Lys Ser Ser Asn Leu Leu Asp Leu Lys Asn Pro Phe Phe Arg Tyr
            305                 310                 315

Thr Gly Thr Thr Pro Ser Pro Pro Gly Ser His Tyr Thr Ser
            320                 325                 330

Pro Ser Glu Asn Met Trp Asn Thr Gly Ser Thr Tyr Asn Leu Ser
            335                 340                 345

Ser Gly Met Ala Val Ala Gly Met Pro Thr Ala Tyr Asp Leu Ser
            350                 355                 360

Ser Val Ile Ala Ser Gly Ser Ser Val Gly His Asn Asn Leu Ile
            365                 370                 375

Pro Leu Ala Asn Thr Gly Ile Val Asn His Thr His Ser Arg Met
            380                 385                 390

Gly Ser Ile Met Ser Thr Gly Ile Val Gln Ser Ser Gly Ala
            395                 400                 405

Gln Gly Ser Gly Gly Ser Thr Ser Ala His Tyr Ala Val Asn
            410                 415                 420

Ser Gln Phe Thr Met Gly Gly Pro Ala Ile Ser Met Ala Ser Pro
```

```
                425                 430                 435
Met Ser Ile Pro Thr Asn Thr Met His Tyr Gly Ser
                440                 445
```

(2) INFORMATION FOR SEQ ID NO: 4:

(i) SEQUENCE CHARACTERISTICS:
        (A) LENGTH: 1975 base pairs
        (B) TYPE: nucleic acid
        (C) STRANDEDNESS: single
        (D) TOPOLOGY: linear (vii) IMMEDIATE SOURCE:
        (A) LIBRARY: PROSNOT20
        (B) CLONE: 1815528

(xi) SEQUENCE DESCRIPTION: SEQ ID NO: 4:

```
CAAAAAAACA CCCCTCATCC AGTCTCTTCC AGCCTAGAGA TCCTGGCCTA CCCCTCCGCC      60
AAAGCGCGCA CTGAGTGCAA ACCCCAGAGT CAATCCCTGT CCCGGCTCCG CCCCCCGCGT     120
CCGAATCCCG CCCAGCCGGG CCCTCAAGCC CAGTCGGGAC TCGAGCCTAG GGAGGCGAGG     180
TTCCCGCACC GGATAGCATG TTTTTGGCCC AGAGGAGCCT CTGCTCTCTT AGCGGTAGAG     240
CAAAATTCCT GAAGACAATT TCTTCTTCCA AAATCCTCGG ATTCTCTACT TCTGCTAAAA     300
TGTCACTGAA ATTCACAAAT GCAAACGGA TTGAAGGACT TGATAGTAAT GTGTGGATTG      360
AATTTACCAA ATTGGCTGCA GACCCTTCTG TTGTGAATCT TGGCCAAGGC TTTCCAGATA     420
TATCCCCTCC TACATATGTA AAAGAAGAAT TATCAAAGAT TGCAGCAATC GATAGCCTGA     480
ATCAGTATAC ACGAGGCTTT GGCCATCCAT CACTTGTGAA AGCTCTGTCC TATCTGTATG     540
AAAAGCTTTA TCAAAAGCAA ATTGATTCAA ATAAAGAAAT CCTTGTGACA GTAGGAGCAT     600
ATGGATCTCT TTTTAACACC ATTCAAGCAT TAATTGATGA GGGAGATGAA GTCATACTAA     660
TAGTGCCTTT CTATGACTGC TATGAGCCCA TGGTGAGAAT GGCTGGAGCA ACACCTGTTT     720
TTATTCCCCT GAGATCTAAA CCTGTTTATG GAAAAAGATG GTCTAGTTCT GACTGGACAT     780
TAGATCCTCA AGAACTGGAA AGTAAATTTA ATTCCAAAAC CAAAGCTATT ATACTAAATA     840
CTCCACATAA CCCACTTGGC AAGGTGTATA ACAGAGAGGA ACTGCAAGTA ATTGCTGACC     900
TTTGCATCAA ATATGACACA CTCTGCATCA GTGATGAGGT TTATGAATGG CTTGTATATT     960
CTGGAAATAA GCACTTAAAA ATAGCTACTT TTCCAGGTAT GTGGGAGAGA ACAATAACAA    1020
TAGGAAGTGC TGGAAAGACT TTCAGTGTAA CTGGCTGGAA GCTTGGCTGG TCCATTGGTC    1080
CAAATCATTT GATAAAACAT TTACAGACAG TTCAACAAAA CACGATTTAT ACTTGTGCAA    1140
CTCCTTTACA GGAAGCCTTG GCTCAAGCTT TCTGGATTGA CATCAAGCGC ATGGATGACC    1200
CAGAATGTTA CTTTAATTCT TTGCCAAAAG AGTTAGAAGT AAAAAGAGAT CGGATGGTAC    1260
GTTTACTTGA AAGTGTTGGC CTAAAACCCA TAGTTCCTGA TGGAGGATAC TTCATCATCG    1320
CTGATGTGTC TTTGCTAGAT CCAGACCTCT CTGATATGAA GAATAATGAG CCTTATGACT    1380
ATAAGTTTGT GAAATGGATG ACTAAACATA AGAAACTATC AGCCATCCCC GTTTCAGCAT    1440
TCTGTAACTC AGAGACTAAA TCACAGTTTG AGAAGTTTGT GCGTTTTTGC TTCATTAAAA    1500
AAGACAGCAC ACTGGATGCT GCTGAAGAAA TCATCAAGGC ATGGAGTGTA CAGAAGTCTT    1560
GATTTGTGCA GAATGGATTA ATGTTTCTGT TAGATGACCT AGTATGGAAT TGTTACTTAG    1620
TGCTGCCACC TGCTGGATGT TAAAAGGTAT TTCAGTACAA CTGGAATTTA AATATTTCCA    1680
TTGTTTTTCC AAAGCAGTTA ACCCAACTCC TAACAACATT TTCGGGGGAT CTGACCTTTT    1740
TTTTCCAGTT GAAATGTATT AACACACCTT CCACAATCAT TTTATAAGAG TCAGCATAAC    1800
```

| | |
|---|---|
| ATAGTGGATA AGAACTGTGA GATGTTTAAC CTCTCAGTAA CTCGGTTCTC TCATTATAAA | 1860 |
| ATAGGAATAA AATCAGTACC TGTTTCATAT GAAGGTCGTT TCTGAGAATT AAATGGACTA | 1920 |
| ATGTATGCAA AAAGCCTGGC AAACAATAAA CACTCATCTG ACTTTAAAAA AAAAA | 1975 |

(2) INFORMATION FOR SEQ ID NO: 5:

(i) SEQUENCE CHARACTERISTICS:
        (A) LENGTH: 2125 base pairs
        (B) TYPE: nucleic acid
        (C) STRANDEDNESS: single
        (D) TOPOLOGY: linear (vii) IMMEDIATE SOURCE:
        (A) LIBRARY: BRAINOT09
        (B) CLONE: 2150892

(xi) SEQUENCE DESCRIPTION: SEQ ID NO: 5:

| | |
|---|---|
| GCGCGTGGGA AGCCAGACGC AGCGGGGGA CACATCTCGC GGTGGCGTTG CCAGAGTGAG | 60 |
| GAGTTAGCAG GCAGGACTTG ACGAGGCTCT TTGGTTTTTC TAGTCCTCAA CCACTGAAGA | 120 |
| AGAAGCTTGA TGCTTGGCTG TCAGAAGACA TGAATTACGC ACGGTTCATC ACGGCAGCGA | 180 |
| GCGCACGCAG AAACCCTACT CCCATCCGGA CCATGACTGA CATATTGAGC AGAGGACCAA | 240 |
| AATCGATGAT CTCCTTGGCT GGTGGCTTAC CAAATCCAAA CATGTTTCCT TTTAAGACTG | 300 |
| CCGTAATCAC TGTAGAAAAT GGAAAGACCA TCCAATTTGG AGAAGAGATG ATGAAGAGAG | 360 |
| CACTTCAGTA TTCTCCGAGT GCTGGAATTC CAGAGCTTTT GTCCTGGCTA AAACAGTTAC | 420 |
| AAATAAAATT GCATAATCCT CCTACCATCC ATTACCCACC CAGTCAAGGA CAAATGGATC | 480 |
| TATGTGTCAC ATCTGGCAGC CAACAAGGTC TTTGTAAGGT GTTTGAAATG ATCATTAATC | 540 |
| CTGGAGATAA TGTCCTCCTA GATGAACCTG CTTATTCAGG AACTCTTCAA AGTCTGCACC | 600 |
| CACTGGGCTG CAACATTATT AATGTTGCCA GTGATGAGAG TGGGATTGTT CCAGATTCCC | 660 |
| TAAGAGACAT ACTTTCCAGA TGGAAACCAG AAGATGCAAA GAATCCCCAG AAAAACACCC | 720 |
| CCAAATTTCT TTATACTGTT CCAAATGGCA ACAACCCTAC TGGAAACTCA TTAACCAGTG | 780 |
| AACGCAAAAA GGAAATCTAT GAGCTTGCAA GAAAATATGA TTTCCTCATA ATAGAAGATG | 840 |
| ATCCTTACTA TTTTCTCCAG TTTAACAAGT TCAGGGTACC AACATTTCTT TCCATGGATG | 900 |
| TTGATGGACG TGTCATCAGA GCTGACTCTT TTTCAAAAAT CATTTCCTCT GGGTTGAGAA | 960 |
| TAGGATTTTT AACTGGTCCA AAACCCTTAA TAGAGAGAGT TATTTTACAC ATACAAGTTT | 1020 |
| CAACATTGCA CCCCAGCACT TTTAACCAGC TCATGATATC ACAGCTTCTA CACGAATGGG | 1080 |
| GAGGAGAAGG TTTCATGGCT CATGTAGACA GGGTTATTGA TTTCTATAGT AACCAGAAGG | 1140 |
| ATGCAATACT GGCAGCTGCA GACAAGTGGT TAACTGGTTT GGCAGAATGG CATGTTCCTG | 1200 |
| CTGCTGGAAT GTTTTTATGG ATTAAAGTTA AAGGCATTAA TGATGTAAAA GAACTGATTG | 1260 |
| AAGAAAAGGC CGTTAAGATG GGGGTATTAA TGCTCCCTGG AAATGCTTTC TACGTCGATA | 1320 |
| GCTCAGCTCC TAGCCCTTAC TTGAGAGCAT CCTTCTCTTC AGCTTCTCCA GAACAGATGG | 1380 |
| ATGTGGCCTT CCAGGTATTA GCACAACTTA TAAAAGAATC TTTATGAAGA AATTAAACTA | 1440 |
| GGTTGGGCAT GGTGGCTCAC ACCTATAATC CCAGCACTTT GGGAGGCAGA GGAGGGAGGA | 1500 |
| TCACTTGGAC CCAGGAATTC AAGGCTGCAG TAAGCTACGA TCACACCACT GCACTCTGGC | 1560 |
| CTGCATGCAC TCTGGCCTGC ATGGCAGAAC AAGACCCTGT CTCTAAAAAA AGAGAAAGAA | 1620 |
| ATCAAACTAA TCATGCTGCT CATGGATTTT TCCAATAAAT TTCTTGTTTT GGCAGGAAGA | 1680 |
| AATGAACACT GGTATTAGAC TTAAAGATTA AATTTCCTCA AACATGTCCT ATCTGTAGTA | 1740 |

-continued

```
GTTCAACTAG ACACCTTTTA AAGTGCCTCT AAATTCATCA GATGGCCAAA CTGTATTTAT      1800

AATCCACTTA GGCATTTTGA AAAACTTTCA ACCTGTAAAA AGTTACTTTT ATCTTGGATT      1860

TATTATGAAG AACTTTGTAG TTGCTTTGTA ATTTCCCATA AATTGTCTTT GAAACTAACA      1920

TTTTACACTG AATTATTTTG AGATTTTAAA GAAGTAATTA AGTGCAAAAT GGTATATAAT      1980

GTGTACTTTT TCTACTTTTA GGAAAATTTA ATGAGAGCTT ATTGCAAAAA TTGTTATAAT      2040

TTGGTCATTA TAAGTGACTT TTAGTAAAAG TACCATAAAC CTTATGTTAT GCCACAGAAA      2100

TTCCTTTAAA ATAAAATTCT TAAAT                                            2125
```

(2) INFORMATION FOR SEQ ID NO: 6:

(i) SEQUENCE CHARACTERISTICS:
  (A) LENGTH: 2224 base pairs
  (B) TYPE: nucleic acid
  (C) STRANDEDNESS: single
  (D) TOPOLOGY: linear (vii) IMMEDIATE SOURCE:
  (A) LIBRARY: BRAITUT21
  (B) CLONE: 2525071

(xi) SEQUENCE DESCRIPTION: SEQ ID NO: 6:

```
CAGAGTGCAG CCGTGTGGGC AAGCAGTCCT TCATCATCAC CCTGGGCTGC AACAGCGTCC        60

TCATCCAGTT CGCCACACCC AACGATTCGG CTCGAGCTTC TACAACATCC TGAAAACCTG       120

CCGGGGCCAC ACCCTGGAGC GGTCTGTGTT CAGCGAGCGG ACGGAGGAGT CTTCTGCCGT       180

GCAGTACTTC CAGTTTTATG GCTACCTGTC CCAGCAGCAG AACATGATGC AGGACTACGT       240

GCGGACAGGC ACCTACCAGC GCGCCATCCT GCAAAACCAC ACCGACTTCA AGGACAAGAT       300

CGTTCTTGAT GTTGGCTGTG GCTCTGGGAT CCTGTCGTTT TTTGCCGCCC AAGCTGGAGC       360

ACGGAAAATC TACGCGGTGG AGGCCAGCAC CATGGCCCAG CACGCTGAGG TCTTGGTGAA       420

GAGTAACAAC CTGACGGACC GCATCGTGGT CATCCCGGGC AAGGTGGAGG AGGTGTCACT       480

CCCCGAGCAG GTGGACATCA TCATCTCGGA GCCCATGGGC TACATGCTCT TCAACGAGCG       540

CATGCTGGAG AGCTACCTCC ACGCCAAGAA GTACCTGAAG CCCAGCGGAA ACATGTTTCC       600

TACCATTGGT GACGTCCACC TTGCACCCTT CACGGATGAA CAGCTCTACA TGGAGCAGTT       660

CACCAAGGCC AACTTCTGGT ACCAGCCATC TTTCCATGGA GTGGACCTGT CGGCCCTCCG       720

AGGTGCCGCG GTGGATGAGT ATTTCCGGCA GCCTGTGGTG GACACATTTG ACATCCGGAT       780

CCTGATGGCC AAGTCTGTCA AGTACACGGT GAACTTCTTA GAAGCCAAAG AAGGAGATTT       840

GCACAGGATA GAAATCCCAT TCAAATTCCA CATGCTGCAT TCAGGGCTGG TCCACGGCCT       900

GGCTTTCTGG TTTGACGTTG CTTTCATCGG CTCCATAATG ACCGTGTGGC TGTCCACAGC       960

CCCGACGAG CCCCTGACCC ACTGGTACCA GGTGCGGTGC CTGTTCCAGT CACCACTGTT      1020

CGCCAAGGCA GGGGACACGC TCTCAGGGAC ATGTCTGCTT ATTGCCAACA AAGACAGAG      1080

CTACGACATC AGTATTGTGG CCCAGGTGGA CCAGACCGGC TCCAAGTCCA GTAACCTCCT      1140

GGATCTGAAA AACCCCTTCT TTAGATACAC GGGCACAACG CCCTCACCCC CACCCGGCTC      1200

CCACTACACA TCTCCCTCGG AAAACATGTG GAACACGGGC AGCACCTACA ACCTCAGCAG      1260

CGGGATGGCC GTGGCAGGGA TGCCGACCGC CTATGACTTG AGCAGTGTTA TTGCCAGTGG      1320

CTCCAGCGTG GGCCACAACA ACCTGATTCC TTTAGCCAAC ACGGGGATTG TCAATCACAC      1380

CCACTCCCGG ATGGGCTCCA TAATGAGCAC GGGGATTGTC CAAGGGTCCT CCGGCGCCCA      1440

GGGCAGTGGT GGTGGCAGCA CGAGTGCCCA CTATGCAGTC AACAGCCAGT TCACCATGGG      1500
```

```
CGGCCCCGCC ATCTCCATGG CGTCGCCCAT GTCCATCCCG ACCAACACCA TGCACTACGG      1560

GAGCTAGGGG CCCGCCCCGC GGACTGACAG CACCAGGAAA CCAAATGATG TCCCTGCCCG      1620

CCGCCCCCGC CGGGCGGCTT TCCCCCTTGT ACTGGAGAAG CTCGAACACC CGGTCACAGC      1680

TCTCTTTGCT ATGGGAACTG GGACACTTTT TTACACGATG TTGCCGCCGT CCCCACCCTA      1740

ACCCCCACCT CCCGGCCCTG AGCGTGTGTC GCTGCCATAT TTTACACAAA ATCATGTTGT      1800

GGGAGCCCTC GTCCCCCCTC CTGCCCGCTC TACCCTGACC TGGGCTTGTC ATCTGCTGGA      1860

ACAGGCGCCA TGGGGCCTGC CAGCCCTGCC TGCCAGGTCC CTTAGCACCT GTCCCCCTGC      1920

CTGTCTCCAG TGGGAAGGTA GCCTGGCCAG GCGGGGCCTC CCCTTCGACG ACCAGGCCTC      1980

GGTCACAACG GACGTGACAT GCTGCTTTTT TTAATTTTAT TTTTTTATGA AAAGAACCAG      2040

TGTCAATCCG CAGACCCTCT GTGAAGCCAG GCCGGCCGGG CCGAGCCAGC AGCCCCTCTC      2100

CCTAGACTCA GAGGCGCCGC GGGGAGGGGT GGCCCCGCCG AGGCTTCAGG GGCCCCCTCC      2160

CCACCAAAGG GTTCACCTCA CACTTGAATG TACAACCCAC CCCACTGTCG GGAAGGCCTC      2220

CGTC                                                                 2224

(2) INFORMATION FOR SEQ ID NO: 7:

(i) SEQUENCE CHARACTERISTICS:
        (A) LENGTH: 244 base pairs
        (B) TYPE: nucleic acid
        (C) STRANDEDNESS: single
        (D) TOPOLOGY: linear (vii) IMMEDIATE SOURCE:
        (A) LIBRARY: PROSNOT20
        (B) CLONE: 1815528H1

(xi) SEQUENCE DESCRIPTION: SEQ ID NO: 7:

ATTATACTAA ATACTCCACA TAACCCACTT GGCAAGGTGT ATAACAGAGA GGAACTGCAA       60

GTAATTGCTG ACCTTTGCAT CAAATATGAC ACACTCTGCA TCAGTGATGA GGTTTATGAA      120

TGGCTTGTAT ATTCTGGAAA TAAGCACTTA AAAATAGCTA CTTTTCCAGG TATGTGGGAG      180

AGAACAATAA CAATAGGAAG TGCTGGAAAG ACTTTCAGTG TAACTGGCTG GAAGCTTGGC      240

TGGT                                                                  244

(2) INFORMATION FOR SEQ ID NO: 8:

(i) SEQUENCE CHARACTERISTICS:
        (A) LENGTH: 528 base pairs
        (B) TYPE: nucleic acid
        (C) STRANDEDNESS: single
        (D) TOPOLOGY: linear (vii) IMMEDIATE SOURCE:
        (A) LIBRARY: UTRSTUT05
        (B) CLONE: 2880980F6

(xi) SEQUENCE DESCRIPTION: SEQ ID NO: 8:

ATTAAAGTTA CATTATCTAA AAAAAAAACT AGAAATAACT ATACTGGCTA AATTATAACA       60

CACTTATTTT CATTGAATTT ATGTATCTTT GTTATGTTTT TAGATTATAC TAAATGTGAT      120

TAATTGGAAA ACAATATTTA CCCTTTTTTC CTCCTCTGTT TAGCTACTTT TCCAGGTATG      180

TGGGAGAGAA CAATAACAAT AGGAAGTGCT GGAAAGACTT TCAGTGTAAC TGGCTGGAAG      240

CTTGGCTGGT CCATTGGTCC AAATCATTTG ATAAAACATT TACAGACAGT TCAACAAAAC      300

ACGATTTATA CTTGTGCAAC TCCTTTACAG GAAGCCTTGG CTCAAGCTTT CTGGATTGAC      360
```

```
ATCAAGCGCA TGGATGACCC AGAATGTTAC TTTAATTCTT TGCCAAAAGN GTTAGAAGTA      420

AAAAGAGATC GGATGGTACG TTTACTTGAA AAGTGTTGGG CCTAAAAACC CATAGTTCCN      480

GGANGGAGGG ATACTTCATC ATCGGCTGGA TGNGGNCTTT GGCCAGAT                   528

(2) INFORMATION FOR SEQ ID NO: 9:

(i) SEQUENCE CHARACTERISTICS:
        (A) LENGTH: 622 base pairs
        (B) TYPE: nucleic acid
        (C) STRANDEDNESS: single
        (D) TOPOLOGY: linear (vii) IMMEDIATE SOURCE:
        (A) LIBRARY: PROSNOT20
        (B) CLONE: 1815528X12C1

(xi) SEQUENCE DESCRIPTION: SEQ ID NO: 9:

CAATCGATAG CCTGNAATCA GTATACACGA GGCTTTGGCC ATCCATCACT TGTGAAAGCT       60

CTGTCCTATC TGTATGAAAA GCTTTATCAA AAGCAAATTG ATTCAAATAA AGAAATCCTT      120

GTGACAGTAG GAGCATATGG ATCTCTTTTT AACACCATTC AAGCATTAAT TGATGAGGGA      180

GATGAAGTCA TACTAATAGT GCCTTTCTAT GACTGCTATG AGCCCATGGT GAGAATGGCT      240

GGAGCAACAC CTGTTTTTAT TCCCCTGAGA TCTAAACCTG TTTATGGAAA AAGATGGTCT      300

AGTTCTGACT GGACATTAGA TCCTCAAGAA CTGGAAAGTA AATTTAATTC CAAAACCAAA      360

GCTATTATAC TAAATACTCC ACATAACCCA CTTGGCAAGG TGTATAACAG AGAGGAACTG      420

CAAGTAATTG CTGACCTTTG CATCAAATAT GACACACTCT GATTCAGTGA TGAGGTTTAT      480

GAATGGCTTG TATATTCGGA AATAAGCACT AAAAATAGCT ACTTTCCGGT ATGTGGGAGA      540

GAACAATAAC AATAGGAAGT GCTGGAAAGA CTTCGTGTAA CTGGCTGGAA GCTGGGCTGG      600

TCCTTNGTCC AATCATTGAT AA                                              622

(2) INFORMATION FOR SEQ ID NO: 10:

(i) SEQUENCE CHARACTERISTICS:
        (A) LENGTH: 602 base pairs
        (B) TYPE: nucleic acid
        (C) STRANDEDNESS: single
        (D) TOPOLOGY: linear (vii) IMMEDIATE SOURCE:
        (A) LIBRARY: PROSNOT20
        (B) CLONE: 1815528X17C1

(xi) SEQUENCE DESCRIPTION: SEQ ID NO: 10:

AGCATTAATT GATGAGGGAG ATGAAGTCAT ACTAATAGTG CCTTTCTATG ACTGCTATGA       60

GCCCATGGTG AGAATGGCTG GAGCAACACC TGTTTTTATT CCCCTGAGAT CTAAACCTGT      120

TTATGGAAAA AGATGGTCTA GTTCTGACTG GACATTAGAT CCTCAAGAAC TGGAAAGTAA      180

ATTTAATTCC AAAACCAAAG CTATTATACT AAATACTCCA CATAACCCAC TTGGCAAGGT      240

GTATAACAGA GAGGAACTGC AAGTAATTGC TGACCTTTGC ATCAAATATG ACACACTCTG      300

CATCAGTGAT GAGGTTTATG AATGGCTTGT ATATTCTGGA AATAAGCACT AAAAATAGC      360

TACTTTTCCA GGTATGTGGG AGAGAACAAT AACAATAGGA AGTGCTGGAA AGACTTTCAG      420

TGTAACTGGG CTGGAAGCTT GGCTGGTCCA TTGGTTCCAA ATTCTTTGAT AAAACTTTAC      480

AGACGTTCAA CAAAACACGA TTTATACTGT GGCAACTTCC TTTACAGGAA GCCTGGCTCA      540

AGCTTCTGGA TTGACTCAAG CGCTGGATGA CCCGAATGTT ACTTAATTCT TGCCAAAGAG      600

TA                                                                    602
```

(2) INFORMATION FOR SEQ ID NO: 11:

(i) SEQUENCE CHARACTERISTICS:
        (A) LENGTH: 789 base pairs
        (B) TYPE: nucleic acid
        (C) STRANDEDNESS: single
        (D) TOPOLOGY: linear (vii) IMMEDIATE SOURCE:
        (A) LIBRARY: PROSNOT20
        (B) CLONE: 1819092T6

(xi) SEQUENCE DESCRIPTION: SEQ ID NO: 11:

```
CNAATTTTTA ATTTAATATT TGGTAAGTGT GTGGTTATAT AATTATTTTC ATCATAAGAA    60

TTATGGANAA AATTTACAAA TNACAAAAAT TTGTGATAAT TTACCTTTTT CTCATACTAA   120

ATCCTTCAAG GCCTCACTGT CTTTTTCCTG GGGTCCTGGA GCCTTCTGAC TGGCTTCTCT   180

CTGTGCATTG CAGGACTTCT CCTCAGGTCA ACTTATCTTC TTNTAACATC CANCAGGTNG   240

CAGCNCTAAN TAACNANTCC ATACTAGGTC ATCTAACAGA AACATNAATC CATTCTGCAN   300

NANTCAAGAC TTCTGTACAC TCCANGCCTN GATGATTTCT TCAGCANCAT CCAGTGTGCT   360

GNCTTTTTTA ATGAAGCANA AACGCNCAAA CTTCTCAAAC TGTGATTTAG TCTCTGAGTT   420

ACAGAATGCT GAAACGGGGA TGGCTGATAG TTTCTTATGN TTAGTCATCC ANTTNACNAA   480

CTTATNGTCA TAAGGCTCAT TANTCTCATA TCAGAGATGG CTGGATCTAG CAAAGTCACA   540

TCAGCGATGA TGAAGTATCC TCCNACAGGA CTATGGGGTT TAGGCCACAC TNTCAAGTAN   600

ACGTACCNTC CGNGTCTNCT TACTCCAACT CTTTNGNAAG ATTAAAGTAA CATTCTGGGN   660

CAACATGCGC CGATGCATCN AGAAGCTNAN CCAGGGNCTG NTNNAGATCT AAAACCGAAA   720

GNATTGGNCG TATTTNGTAC TTNNGTAGAA TGGAGCCGGT AATTTGGAAG AGCNCCCGAA   780

ACGGATCTG                                                          789
```

(2) INFORMATION FOR SEQ ID NO: 12:

(i) SEQUENCE CHARACTERISTICS:
        (A) LENGTH: 646 base pairs
        (B) TYPE: nucleic acid
        (C) STRANDEDNESS: single
        (D) TOPOLOGY: linear (vii) IMMEDIATE SOURCE:
        (A) LIBRARY: HNT2NOT01
        (B) CLONE: 269916F1

(xi) SEQUENCE DESCRIPTION: SEQ ID NO: 12:

```
AAAGTCAGAT GAGTGTTTAT TGTTTGCCAG GNTTTTTGCA TACATTAGTC CATTTAATTC    60

TCAGAAACGA CCTTCATATG AAACAGGTAC TGATTTTATT CCTATTTTAT AATGAGAGAA   120

CCGAGTTACT GAGAGGTTAA ACATCTCACA TTTCTTATCC ACTATGTTAT GCTGACTCTT   180

ATAAAATGAT TGTGGAAGGT GTGTTAATAC ATTTCAACTG GAAAAAAAAG GTCAGATCCC   240

CCGAAAATGT TGTTAGGAGT TGGGTTAACT GCTTTGGAAA AACAATGGAA ATATTTAAAT   300

TCCAGTTGTA CTGAAATACC TTTTAACATC CAGCAGGTGG CAGCACTAAG TAACAATTCC   360

ATACTAGGTC ATCTAACAGA AACATTAATC CATTCTGCAC AAATCAAGAC TTCTGTACAC   420

TCCATGCCTT GATGATTTCT TCAGCAGCAT CCAGTGTGCT GTCTTTTTTA ATGAAGCAAA   480

AACGCACAAA CTTCTCAACT GTGATTTAGT CTCTGAGTTA CAGANTGCTG AAACGGGGTG   540

GCTGNTAGTT TCTTATGTTT AGGCCATCCA TTTCACAAAC TTATAGNCAT AAGGCTCATT   600
```

```
ATTCTTCATA TCAGNGNGGT CTGGGNCTGG CAANGGCACA TNAGCG                    646
```

(2) INFORMATION FOR SEQ ID NO: 13:

(i) SEQUENCE CHARACTERISTICS:
        (A) LENGTH: 369 base pairs
        (B) TYPE: nucleic acid
        (C) STRANDEDNESS: single
        (D) TOPOLOGY: linear (vii) IMMEDIATE SOURCE:
        (A) LIBRARY: UCMCNOT02
        (B) CLONE: 1717401F6

(xi) SEQUENCE DESCRIPTION: SEQ ID NO: 13:

```
AGCTAGTATG GAATTGTTAC TTAGTGCTGC CACCTGCTGG ATGTTAAAAG GNATTTCAGT      60

ACAACTGGAA TTTAAATATT TCCATTGTTT TTCCAAAGCA GTTAACCCAA CTCCTAACAA     120

CATTTTCGGG GGATCTGACC TTTTTTTTCC AGTTGAAATG TATTAACACA CCTTCCACAA     180

TCATTTTATA AGAGTCAGCA TAACATAGTG GATAAGAACT GTGAGATGTT TAACCTCTCA     240

GTAACTCGGT TCTCTCATTA TAAAATAGGA ATAAAATCAG TACCTGTTTC ATATGAAGGT     300

CGTTTCTGAG AATTAAATGG ACTAATGTAT GCAAAAAGCC TGGCAAACAA TAAACACTCA     360

TCTGACTTT                                                            369
```

(2) INFORMATION FOR SEQ ID NO: 14:

(i) SEQUENCE CHARACTERISTICS:
        (A) LENGTH: 243 base pairs
        (B) TYPE: nucleic acid
        (C) STRANDEDNESS: single
        (D) TOPOLOGY: linear (vii) IMMEDIATE SOURCE:
        (A) LIBRARY: BRAINOT09
        (B) CLONE: 2150892H1

(xi) SEQUENCE DESCRIPTION: SEQ ID NO: 14:

```
GACCATCCAA TTTGGAGAAG AGATGATGAA GAGAGCACTT CAGTATTCTC CGAGTGCTGG      60

AATTCCAGAG CTTTTGTCCT GGCTAAAACA GTTACAAATA AAATTGCATA ATCCTCCTAC     120

CATCCATTAC CCACCCAGTC AAGGACAAAT GGATCTATGT GTCACATCTG GCAGCCAACA     180

AGGTCTTTGT AAGGTGTTTG ANATGATCAT TAATCCTGGA GATAATGTCC TCCTAGATGA     240

ACC                                                                  243
```

(2) INFORMATION FOR SEQ ID NO: 15:

(i) SEQUENCE CHARACTERISTICS:
        (A) LENGTH: 569 base pairs
        (B) TYPE: nucleic acid
        (C) STRANDEDNESS: single
        (D) TOPOLOGY: linear (vii) IMMEDIATE SOURCE:
        (A) LIBRARY: N/A
        (B) CLONE: SAGA00872F1

(xi) SEQUENCE DESCRIPTION: SEQ ID NO: 15:

```
AGGCGCGTGG GAAGCCAGAC GCAGCGGGGG GACACATCTC GCGGTGGCGT TGCAGAGTGA      60

GGNGTTAGCA GGCAGGACTT GACGAGGCTC TTTGGTTTTT CTAGTCCTCA ACCACTGAAG     120

AAGAAGCTTG ATGCTTGGCT GTCAGAAGAC ATGAATTACG CACGGTTCAT CACGGCAGCG     180

AGCGCANCAG AAACCCTACT CCCATCCGGA CCATGACTGA CATATTGAGC AGAGGACCAA     240
```

-continued

```
AATCGATGAT CTCCTTGGCT GGTGGCTTAC CAAATCCAAA CATGTTTCCT TTTAAGACTG      300

CCGTAATCAC TGTAGAAAAT GGAAAGACCA TCCAATTTGG AGAAGAGATG ATGAAGAGAG      360

CACTTCAGTA TTCTCCGAGT GCTGGAATTC CAGAGCTTTT GTCCTGGCTA AAACAGTTAC      420

AAATAAAATT GCATAATCCT CCTACCATCC ATTACCACCC AGTCAAGGAC AAATGGATCT      480

ATGTGTCACA TCTGGCAGCC AACAAGGTCT TTGTAAGGTG TTTGAAATGA TCATTAATCC      540

TGGAGATAAT GTCCTCCTAG ATGAACCTG                                       569
```

(2) INFORMATION FOR SEQ ID NO: 16:

(i) SEQUENCE CHARACTERISTICS:
        (A) LENGTH: 526 base pairs
        (B) TYPE: nucleic acid
        (C) STRANDEDNESS: single
        (D) TOPOLOGY: linear (vii) IMMEDIATE SOURCE:
        (A) LIBRARY: N/A
        (B) CLONE: SAGA01877F1

(xi) SEQUENCE DESCRIPTION: SEQ ID NO: 16:

```
GGTCGACTCT AGAGGATCCC CCCATGAAAC CTTCTCCTCC CCATTCGTGT AGAAGCTGTG       60

ATATCATGAG CTGGTCAAAA GTGCTGGGGT GCAATGTTGA AACTTGTATG TGTAAAATAA      120

CTCTCTCTAT TAAGGGTTTT GGACCAGTTA AAAATCCTAT TCTCAACCCA GAGGGAATGA      180

TTTTTGAAAA AGAGTCAGCT CTGATGACAC GTCCATCAAC ATCCATGGAA AGAAATGTTG      240

GTACCCTGAA CTTGTTAAAC TGGAGAAAAT AGTAAGGATC ATCTTCTATT ATGAGGAAAT      300

CATATTTTCT TGCAAGCTCA TAGATTTCCT TTTTGCGTTC ACTGGTTAAT GAGTTTCCAG      360

TAGGGTTGTT GCCATTTGGA ACAGTATAAA GAAATTTGGG GGTGTTTTTC TGGGGATTCT      420

TTGCATCTTC TGGTTTCCAT CTGGAAAGTA TGTCTCTTAG GGAATCTGGA ACAATCCCAC      480

TCTCATCACT GGCAACATTA ATAATGTTGC AGGGGTACCG AGCTCG                    526
```

(2) INFORMATION FOR SEQ ID NO: 17:

(i) SEQUENCE CHARACTERISTICS:
        (A) LENGTH: 467 base pairs
        (B) TYPE: nucleic acid
        (C) STRANDEDNESS: single
        (D) TOPOLOGY: linear (vii) IMMEDIATE SOURCE:
        (A) LIBRARY: N/A
        (B) CLONE: SAGA01269R1

(xi) SEQUENCE DESCRIPTION: SEQ ID NO: 17:

```
TTATTAATGT TGCCAGTNAT GAGAGTGGGA TTGTTCCAGA TTCCCTAAGA GACATACTTT       60

CCAGATGGAA ACCAGAAGAT GCAAAGAATC CCCAGAAAAA CACCCCCAAA TTTCTTTATA      120

CTGTTCCAAA TGGCAACAAC CCTACTGGAA ACTCATTAAC CAGTGAACGC AAAAAGGAAA      180

TCTATGAGCT TGCAAGAAAA TATGATTTCC TCATAATAGA AGATGATCCT TACTATTTTC      240

TCCAGTTTAA CAAGTTCAGG GTACCAACAT TTCTTTCCAT GGATGTTGAT GGACGTGTCA      300

TCAGAGCTGA CTCTTTTTCA AAAATCATTT CCTCTGGGTT GAGAATAGGA TTTTTAACTG      360

GTCCAAAACC CTTAATAGAG AGAGTTATTT TACACATACA AGTTTCAACA TTGCACCCCA      420

GCACTTTTAA CCAGCTCATG ATATCACAGG GGGATCCTCT AGAGTCG                   467
```

(2) INFORMATION FOR SEQ ID NO: 18:

(i) SEQUENCE CHARACTERISTICS:
        (A) LENGTH: 338 base pairs
        (B) TYPE: nucleic acid
        (C) STRANDEDNESS: single
        (D) TOPOLOGY: linear (vii) IMMEDIATE SOURCE:
        (A) LIBRARY: N/A
        (B) CLONE: SAGA02228F1

(xi) SEQUENCE DESCRIPTION: SEQ ID NO: 18:

```
GCAGGTCGAC TCTAGAGGAT CCCCCTGCAG ACAAGTGGTT AACTGGTTTG GCAGAATGGC      60

ATGTTCCTGC TGCTGGAATG TTTTTATGGA TTAAAGTTAA AGGCATTAAT GATGTAAAAG     120

AACTGATTGA AGAAAAGGCC GTTAAGATGG GGGTATTAAT GCTCCCTGGA AATGCTTTCT     180

ACGTCGATAG CTCAGCTCCT AGCCCTTACT TGAGAGCATC CTTCTCTTCA GCTTCTCCAG     240

AACAGATGGA TGTGGCCTTC CAGGTATTAG CACAACTTAT AAAAGAATCT TTATGAAGAA     300

ATTAAACTAG GTTGGGCATG GTGGGGGTAC CGAGCTCG                             338
```

(2) INFORMATION FOR SEQ ID NO: 19:

(i) SEQUENCE CHARACTERISTICS:
        (A) LENGTH: 605 base pairs
        (B) TYPE: nucleic acid
        (C) STRANDEDNESS: single
        (D) TOPOLOGY: linear (vii) IMMEDIATE SOURCE:
        (A) LIBRARY: N/A
        (B) CLONE: SAGA01614F1

(xi) SEQUENCE DESCRIPTION: SEQ ID NO: 19:

```
TGCAGGTCGA CTCTAGAGGA TCCCCCCGTT AAGATGGGGG TATTAATGCT CCCTGGAAAT      60

GCTTTCTACG TCGATAGCTC AGCTCCTAGC CCTTACTTGA GAGCATCCTT CTCTTCAGCT     120

TCTCCAGAAC AGATGGATGT GGCCTTCCAG GTATTAGCAC AACTTATAAA AGAATCTTTA     180 nnnnnnnnnn nnnnnnnnnn nnnnnnnnnn nnnnnnnnnn nnnnnnnnnn nnnnnnnnnn     240 nnnnnnnnnn nnnnnnnnnn nnnnnnnnnn nnnnnnnnnn nnnnnnnnnn nnnnnnnnnn     300 nnnnnnnnnn nnnnnnnnnn nnnnnnnnnn nnnnnnnnnn nnnnnnnnnn nnnnnnnnnn     360 nnnnnnnnnn nnnnnnnnnn nnnnnnTCAT GCTGCTCATG GATTTTTCCA ATAAATTTCT     420

TGTTTTGGCA GGAAGAAATG AACACTGGTA TTAGACTTAA AGATTAAATT TCCTCAAACA     480

TGTCCTATTC TGTAGNAGTT CAACTAGACA CCTTTTAAAG TGCCTCTAAA TTCATCAGAT     540

GGCCAAACTG TATTTATAAT CCACTTAGGC ATTTTGAAAA ACTTCAACCT GTAAAAAGNT     600

ACTTT                                                                 605
```

(2) INFORMATION FOR SEQ ID NO: 20:

(i) SEQUENCE CHARACTERISTICS:
        (A) LENGTH: 495 base pairs
        (B) TYPE: nucleic acid
        (C) STRANDEDNESS: single
        (D) TOPOLOGY: linear (vii) IMMEDIATE SOURCE:
        (A) LIBRARY: TESTNOT04
        (B) CLONE: 301251T6

(xi) SEQUENCE DESCRIPTION: SEQ ID NO: 20:

```
GTTAAGAATT TTATTTTAAA GGAATTTCTG TGGCATAACA TAAGGTTTAT GGTACTTTTA      60

CTAAAGTCA CTTATAATGA CCAAATTATA ACAATTTTTG CAATAAGCTC TCATTAAATT      120
```

| | | |
|---|---|---|
| TTCCTAAAAG TAGAAAAAGT ACACATTATA TACCATTTTG CACTTAATTA CTTCTTTAAA | 180 | |
| ATCTCAAAAT AATTCAGTGT AAAATGTTAG TTTCAAAGAC AATTTATGGG AAATTACAAA | 240 | |
| GCAACTACAA AGTTCTTCAT AATAANTCCA AGATAAAAGT AACTTTTTAC AGGTTGAAAG | 300 | |
| TTTTTCAAAA TGCCTAAGTG GATTATAAAT ACAGTTTGGC CATCTGATGA ATTTAGAGGC | 360 | |
| ACTTTAAAAG GTGTCTAGTT GAACTACTAC AGATAGGACA TGTTTGAGGA AATTTAATCT | 420 | |
| TTAAGTCTAA TACCAGTGGT CATTTCCTCC TGCCAAAACA AGANATTTAT TGGAAAAATC | 480 | |
| CATGAGCAGC ATGAT | 495 | |

(2) INFORMATION FOR SEQ ID NO: 21:

(i) SEQUENCE CHARACTERISTICS:
        (A) LENGTH: 256 base pairs
        (B) TYPE: nucleic acid
        (C) STRANDEDNESS: single
        (D) TOPOLOGY: linear (vii) IMMEDIATE SOURCE:
        (A) LIBRARY: BRAITUT21
        (B) CLONE: 2525071H1

(xi) SEQUENCE DESCRIPTION: SEQ ID NO: 21:

| | | |
|---|---|---|
| CTTCTACAAC ATCCTGAAAA CCTGCCGGGG CCACACCCTG GAGCGGTCTG TGTTCAGCGA | 60 | |
| GCGGACGGAG GAGTCTTCTG CCGTGCAGTA CTTCCAGTTT TATGGCTACC TGTCCCAGCA | 120 | |
| GCAGAACATG ATGCAGGACT ACGTGCGGAC AGGCACCTAC CAGCGCGCCA TCCTGCAAAA | 180 | |
| CCACACCGAC TTCAAGGACA AGATCGTTCT TGATGTTGGC TGTGGCTCTG GGATCCTGTC | 240 | |
| GTTTTTTGCC GCCCAA | 256 | |

(2) INFORMATION FOR SEQ ID NO: 22:

(i) SEQUENCE CHARACTERISTICS:
        (A) LENGTH: 258 base pairs
        (B) TYPE: nucleic acid
        (C) STRANDEDNESS: single
        (D) TOPOLOGY: linear (vii) IMMEDIATE SOURCE:
        (A) LIBRARY: BLADTUT07
        (B) CLONE: 1889292H1

(xi) SEQUENCE DESCRIPTION: SEQ ID NO: 22:

| | | |
|---|---|---|
| CAGAGTGCAG CCGTGTGGGC AAGCAGTCCT TCATCATCAC CCTGGGCTGC AACAGCGTCC | 60 | |
| TCATCCAGTT CGCCACACCC AACGATTTCT GTTCCTTCTA CAACATCCTG AAAACCTGCC | 120 | |
| GGGGCCACAC CCTGGAGCGG TCTGTGTTCA GCGAGCGGAC GGAGGAGTCT TCTGCCGTGC | 180 | |
| AGTACTTCCA GTTTTATGGC TACCTGTCCC AGCAGCAGAA CATGATGCAG GACTACGTGC | 240 | |
| GGACANGCAC CTTACCAG | 258 | |

(2) INFORMATION FOR SEQ ID NO: 23:

(i) SEQUENCE CHARACTERISTICS:
        (A) LENGTH: 631 base pairs
        (B) TYPE: nucleic acid
        (C) STRANDEDNESS: single
        (D) TOPOLOGY: linear (vii) IMMEDIATE SOURCE:
        (A) LIBRARY: BRAITUT21
        (B) CLONE: 2525071F6

(xi) SEQUENCE DESCRIPTION: SEQ ID NO: 23:

```
CTTCTACAAC ATCCTGAAAA CCTGCCGGGG CCACACCCTG GAGCGGTCTG TGTTCAGCGA      60

GCGGACGGAG GAGTCTTCTG CCGTGCAGTA CTTCCAGTTT TATGGCTACC TGTCCCAGCA     120

GCAGAACATG ATGCAGGACT ACGTGCGGAC AGGCACCTAC CAGCGCGGCA TCCTGCAAAA     180

CCACACCGAC TTCAAGGACA AGATCGTTCT TGATGTTGGC TGTGGCTCTG GGATCCTGTC     240

GTTTTTTGCC GCCCAAGCTG GAGCACGGAA AATCTACGCG GTGGAGGCCA GCACCATGGG     300

CCCAGCACGC TGAGGTCTTG GTGAAGAGTA CAACCTGAC GGGACCGCAT CGTGGTCATC      360

CCGGGGCAAA AGTNGAAGGA AGGTGTCACT TCCCCCGAGC AAGGTGGACA TCATTAATCT     420

TGGGANGCCC CATGGGGCNT AANATGGNTC TTTCAAACGA AGCGGCATTG NTGGGAAGAA     480

GCTAACCTTC CANGGGCCAA AGAAAGGTAA CTTGAAAAGN CCCCAANCCG GGAAAAAAAA     540

TGGTTTTTCC CTAAACCATT TTGGGNGGAA NGTTCCCAAC NTTTGGGAAA CCCCTTTCAA     600

GNGGGTTGGA AAAANGTTTC TTAAAANTNG G                                    631

(2) INFORMATION FOR SEQ ID NO: 24:

(i) SEQUENCE CHARACTERISTICS:
        (A) LENGTH: 621 base pairs
        (B) TYPE: nucleic acid
        (C) STRANDEDNESS: single
        (D) TOPOLOGY: linear (vii) IMMEDIATE SOURCE:
        (A) LIBRARY: N/A
        (B) CLONE: SAEA10009P1

(xi) SEQUENCE DESCRIPTION: SEQ ID NO: 24:

ATTTCNGNCN TGTTGCANAA ATGCNNAATT AGGACNCGGA CCCCAACGTC NTCATCCCGG      60

GCAAGGTGGA GGAGGTGTCA CTCCCCGAGC AGGTGGACAT CATCATCTCG GAGCCCATGG     120

GCTACATGCT CTTCAACGAG CGCATGCTGG ANAGCTACCT CCACGCCAAG AAGTACCTGA     180

AGCCCAGCGG AAACATGTTT CCTACCATTG GTGACGTCCA CCTTGCACCC TTCACGGATG     240

AACAGCTCTA CATGGAGCAG TTCACCAAGG CCAACTTCTG GTACCAGCCA TCTTTCCATG     300

GAGTGGACCT GTCGGCCCTC CGAGGTGCCG CNNTGNNTTN TTNTTTCCGG CAGCCTGTGG     360

TGGACACATT TGACATCCGG ATCCTGATGG CCAAGTCTGT CAAGTACACG GTGAACTTCT     420

TAGAAGCCAA AGAAGGAGAT TTGCACAGGA TANAAATCCC ATTCAAATTC CACATGCTGC     480

ATTCAGGGCT GGTCCACGGC CTGGCTTTCT GGTTTGACGT TGCTTTCATC GGCTCCATAA     540

TGACCGTGTG GCTGTCCACA GCCCCGACAG AACCCCTGAC CCACTGGTAC CAGGTGCGGT     600

GCCTGTTCCA GTCACCACTG T                                              621

(2) INFORMATION FOR SEQ ID NO: 25:

(i) SEQUENCE CHARACTERISTICS:
        (A) LENGTH: 549 base pairs
        (B) TYPE: nucleic acid
        (C) STRANDEDNESS: single
        (D) TOPOLOGY: linear (vii) IMMEDIATE SOURCE:
        (A) LIBRARY: N/A
        (B) CLONE: SAEA03283F1

(xi) SEQUENCE DESCRIPTION: SEQ ID NO: 25:

GGCTGGCTGT TGACTGCATA GTGGGCACTC GTGCTGCCAC CACCACTGCC CTGGGCGCCG      60

GAGGACCCTT GGACAATCCC CGTGCTCATT ATGGAGCCCA TCCGGGAGTG GGTGTGATTG     120
```

```
ACAATCCCCG TGTTGGCTAA AGGAATCAGG TTGTTGTGGC CCACGCTGGA GCCACTGGCA      180

ATAACACTGC TCAAGTCATA GGCGGTCGGC ATCCCTGCCA CGGCCATCCC GCTGCTGAGG      240

TTGTAGGTGC TGCCCGTGTT CCACATGTTT TCCGAGGGGA ATGTGTAGTG GGAGCCGGGT      300

GGGGGTGAGG GCGTTGTGCC CGTGTATCTA AGAAGGGGT TTTTCAGATC CAGGAGGTTA       360

CTGGACTTGG AGCCGGTCTG GTCCACCTGG GCCACAATAC TGATGTCGTA GCTCTGTCTT      420

TTGTTGGCAA TAAGCAGACA TGTCCCTGAG AGCGTGTCCC CTGCCTTGGC GAACAGTGGT     480

GACTGGAACA GGCACCGCAC CTGGTACCAG TGGGTCAGGG GCTCTGTCGG GGCTGTGGAC     540

AGCCACACG                                                              549

(2) INFORMATION FOR SEQ ID NO: 26:

(i) SEQUENCE CHARACTERISTICS:
        (A) LENGTH: 647 base pairs
        (B) TYPE: nucleic acid
        (C) STRANDEDNESS: single
        (D) TOPOLOGY: linear (vii) IMMEDIATE SOURCE:
        (A) LIBRARY: N/A
        (B) CLONE: SAEA01931R1

(xi) SEQUENCE DESCRIPTION: SEQ ID NO: 26:

GGTGGACCAG ACCGGCTCCA AGTCCAGTAA CCTCCTGGAT CTGAAAAACC CCTTCTTTAG      60

ATACACGGGC ACAACGCCCT CACCCCCACC CGGCTCCCAC TACACATCTC CCTCGGAAAA    120

CATGTGGAAC ACGGGCAGCA CCTACAACCT CAGCAGCGGG ATGGCCGTGG CAGGGATGCC     180

GACCGCCTAT GACTTGAGCA GTGTTATTGC CAGTGGCTCC AGCGTGGGCC ACAACAACCT     240

GATTCCTTTA GCCAACACGG GGATTGTCAA TCACACCCAC TCCCGGATGG GCTCCATAAT     300

GAGCACGGGG ATTGTCCAAG GGTCCTCCGG CGCCCAGGGC AGTGGTGGTG GCAGCACGAG     360

TGCCCACTAT GCAGTCAACA GCCAGTTCAC CATGGGCGGC CCCGCCAATC TCCATGGCGT     420

CGCCCATGTC CATCCCGACC AACACCATGC ACTACGGGAG CTAGGGGCCC GCCCCGCGGA    480

ACTGACAGCA CCAGGAAACC AAATGATGTC CCTGCNCGCC GCNCCCGCCG GGCGGCTTTT    540

CCCCCTTGTA CTGGAGAAGC TCGAAACAAC CCGGTCACAG CTCTCTTTGC TATGGGAACT    600

GGGACATTTT TTTACACGAT GTTGCCGCCG TCCCCAAAAC GCGGGCG                  647

(2) INFORMATION FOR SEQ ID NO: 27:

(i) SEQUENCE CHARACTERISTICS:
        (A) LENGTH: 655 base pairs
        (B) TYPE: nucleic acid
        (C) STRANDEDNESS: single
        (D) TOPOLOGY: linear (vii) IMMEDIATE SOURCE:
        (A) LIBRARY: LUNGFET03
        (B) CLONE: 1253024T6

(xi) SEQUENCE DESCRIPTION: SEQ ID NO: 27:

CTGCCATATT TTACACAAAA TCATGTTGTG GGAGCCCTCG NCCCCCCTCC TGCCCGCTCT      60

ACCCTGACCT GGGCTTGTCA TCTGCTGGAA CAGGCGCCAT GGGGCCTGCC AGCCCTGCCT    120

GCCAGGTCCC TTAGCACCTG TCCCCCNGCC NGTCTCCAGT GGGAAGGTAG CCTGGCCAGG    180

CGGGGCCTCC CCTTCGACGA CCAGGCCTCG GTCACAACGG ACGTGACATG CTGCTTTTTT    240

TAATTTTATT TTTTTATGAA AAGAACCCAG TGTCAATCCG CAGACCCTCT GTGAAGCCAG    300

GCCGGCCGGG CCGANCAAGA GGNCCTTTTC CCTAGACTCA GAGCCNCCCC GGGGAAGGGG    360
```

```
TTTCCCCGCC GAAGGTTCAG GGNNGCCCCC TTCCCNACCA AAANGGGTTT AACCTCAAAA        420

TTNNAAANGN AANATCTTAC CCCCCATTNN TGGGGAAAGG GCTNCCGNTC CTTNNGCCCC        480

NGNNTTTTTT GGNNNNNTNN TTTTTTTCCN NAANCCCCNG GAAGNTCCCN NNNTTTTTNT        540

TTNNNNANTT AANNNTTTAN ANNNNGGNNG GNNAAAGGNN TTTNGGCCCC CNTGGGGNAA        600

GNNNNTTGNG NGGCNAATTT NGGGGGNNAA AAANGNNNCC NNNAANGGNT TTTTT            655

(2) INFORMATION FOR SEQ ID NO: 28:

(i) SEQUENCE CHARACTERISTICS:
        (A) LENGTH: 529 base pairs
        (B) TYPE: nucleic acid
        (C) STRANDEDNESS: single
        (D) TOPOLOGY: linear (vii) IMMEDIATE SOURCE:
        (A) LIBRARY: BRSTNOT09
        (B) CLONE: 1664573F6

(xi) SEQUENCE DESCRIPTION: SEQ ID NO: 28:

TGCCTGTCTC CAGTGGGAAG GTAGCCTGGC CAGGCGGGGC CTCCCCTTCG ACGACCAGGC         60

CTCGGTCACA ACGGACGTGA CATGCTGCTT TTTTTAATTT TATTTTTTTA TGAAAAGAAC        120

CAGTGTCAAT CCGCAGACCC TCTGTGAAGC CAGGCCGGCC GGGCCGAGCC AGCNGCCCCT        180

CTCCCTAGAC TCAGAGGCGC CGCGGGGAGG GGTNNCCCCG CCGAGGCTTC AGGGNNNCCC        240

TCCCCACCAA AGGGTTCACC TCACACTTGA ATGTACANCC CANCCCACTG TCGGGAAGGC        300

TCCGTCCTCN NCCCCTGCCT CTTGCTGCTG TCCTGTCCCC GANCCCCTGC AGTCNNCTNC        360

NTTTNNCANT NAAGANTAGA GNAGTGGTGN NGCTTGGGCC GGAGGAAGGC ATGCGGCCAN        420

TGGGANAANA GACACTCAAG ATTGTAGGAG GGTCTTTCCT TGAGTAAGTA GCTGAGAGTC        480

CCTCATCTGN TAGTCAGTCT ATATGGAGGA TTCATCCTCC TGCGGAAGA                   529

(2) INFORMATION FOR SEQ ID NO: 29:

(i) SEQUENCE CHARACTERISTICS:
        (A) LENGTH: 220 base pairs
        (B) TYPE: nucleic acid
        (C) STRANDEDNESS: single
        (D) TOPOLOGY: linear (vii) IMMEDIATE SOURCE:
        (A) LIBRARY: LUNGTUT03
        (B) CLONE: 1474156T1

(xi) SEQUENCE DESCRIPTION: SEQ ID NO: 29:

GNNCCTTAAT TTTATTTTTT TATGAAAAGA ACCAGTGTCA ATCCGCAGAC CCTCTGTGAA         60

GCCAGGCCGG CCGGGCCGAG CCAGCAGCCC CTCTCCCTAG ACTCAGAGGC GCCGCGGGGA        120

GGGGTGGCCC CGCCGAGGCT TCAGGGGCCC CCTCCCCACC AAAGGGTTCA CCTCACACTT        180

GAATGTACAA CCCACCCCAC TGTCGGGAAG GCCTCCGTCC                             220

(2) INFORMATION FOR SEQ ID NO: 30:

(i) SEQUENCE CHARACTERISTICS:
        (A) LENGTH: 422 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: GI 758591
```

(xi) SEQUENCE DESCRIPTION: SEQ ID NO: 30:

Met Ala Lys Gln Leu Gln Ala Arg Arg Leu Asp Gly Ile Asp Tyr
                5                  10                  15

Asn Pro Trp Val Glu Phe Val Lys Leu Ala Ser Glu His Asp Val
                20                  25                  30

Val Asn Leu Gly Gln Gly Phe Pro Asp Phe Pro Pro Asp Phe
                35                  40                  45

Ala Val Glu Ala Phe Gln His Ala Val Ser Gly Asp Phe Met Leu
                50                  55                  60

Asn Gln Tyr Thr Lys Thr Phe Gly Tyr Pro Pro Leu Thr Lys Ile
                65                  70                  75

Leu Ala Ser Phe Phe Gly Glu Leu Leu Gly Gln Glu Ile Asp Pro
                80                  85                  90

Leu Arg Asn Val Leu Val Thr Val Gly Gly Tyr Gly Ala Leu Phe
                95                 100                 105

Thr Ala Phe Gln Ala Leu Val Asp Glu Gly Asp Glu Val Ile Ile
               110                 115                 120

Ile Glu Pro Phe Phe Asp Cys Tyr Glu Pro Met Thr Met Met Ala
               125                 130                 135

Gly Gly Arg Pro Val Phe Val Ser Leu Lys Pro Gly Pro Ile Gln
               140                 145                 150

Asn Gly Glu Leu Gly Ser Ser Ser Asn Trp Gln Leu Asp Pro Met
               155                 160                 165

Glu Leu Ala Gly Lys Phe Thr Ser Arg Thr Lys Ala Leu Val Leu
               170                 175                 180

Asn Thr Pro Asn Asn Pro Leu Gly Lys Val Phe Ser Arg Glu Glu
               185                 190                 195

Leu Glu Leu Val Ala Ser Leu Cys Gln Gln His Asp Val Val Cys
               200                 205                 210

Ile Thr Asp Glu Val Tyr Gln Trp Met Val Tyr Asp Gly His Gln
               215                 220                 225

His Ile Ser Ile Ala Ser Leu Pro Gly Met Trp Glu Arg Thr Leu
               230                 235                 240

Thr Ile Gly Ser Ala Gly Lys Thr Phe Ser Ala Thr Gly Trp Lys
               245                 250                 255

Val Gly Trp Val Leu Gly Pro Asp His Ile Met Lys His Leu Arg
               260                 265                 270

Thr Val His Gln Asn Ser Val Phe His Cys Pro Thr Gln Ser Gln
               275                 280                 285

Ala Ala Val Ala Glu Ser Phe Glu Arg Glu Gln Leu Leu Phe Arg
               290                 295                 300

Gln Pro Ser Ser Tyr Phe Val Gln Phe Pro Gln Ala Met Gln Arg
               305                 310                 315

Cys Arg Asp His Met Ile Arg Ser Leu Gln Ser Val Gly Leu Lys
               320                 325                 330

Pro Ile Ile Pro Gln Gly Ser Tyr Phe Leu Ile Thr Asp Ile Ser
               335                 340                 345

Asp Phe Lys Arg Lys Met Pro Asp Leu Pro Gly Ala Val Asp Glu
               350                 355                 360

Pro Tyr Asp Arg Arg Phe Val Lys Trp Met Ile Lys Asn Lys Gly
               365                 370                 375

Leu Val Ala Ile Pro Val Ser Ile Phe Tyr Ser Val Pro His Gln

```
                        380                 385                 390
Lys His Phe Asp His Tyr Ile Arg Phe Cys Phe Val Lys Asp Glu
                395                 400                 405
Ala Thr Leu Gln Ala Met Asp Glu Lys Leu Arg Lys Trp Lys Val
                410                 415                 420
Glu Leu (2) INFORMATION FOR SEQ ID NO: 31:

(i) SEQUENCE CHARACTERISTICS:
        (A) LENGTH: 425 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: GI 1050752

(xi) SEQUENCE DESCRIPTION: SEQ ID NO: 31:

Met Asn Tyr Ser Arg Phe Leu Thr Ala Thr Ser Leu Ala Arg Lys
                 5                  10                  15
Thr Ser Pro Ile Arg Ala Thr Val Glu Ile Met Ser Arg Ala Pro
                20                  25                  30
Lys Asp Ile Ile Ser Leu Ala Pro Gly Ser Pro Asn Pro Lys Val
                35                  40                  45
Phe Pro Phe Lys Ser Ala Val Phe Thr Val Glu Asn Gly Ser Thr
                50                  55                  60
Ile Arg Phe Glu Gly Glu Met Phe Gln Arg Ala Leu Gln Tyr Ser
                65                  70                  75
Ser Ser Tyr Gly Ile Pro Glu Leu Leu Ser Trp Leu Lys Gln Leu
                80                  85                  90
Gln Ile Lys Leu His Asn Pro Pro Thr Val Asn Tyr Ser Pro Asn
                95                 100                 105
Glu Gly Gln Met Asp Leu Cys Ile Thr Ser Gly Cys Gln Asp Gly
               110                 115                 120
Leu Cys Lys Val Phe Glu Met Leu Ile Asn Pro Gly Asp Thr Val
               125                 130                 135
Leu Val Asn Glu Pro Leu Tyr Ser Gly Ala Leu Phe Ala Met Lys
               140                 145                 150
Pro Leu Gly Cys Asn Phe Ile Ser Val Pro Ser Asp Asp Cys Gly
               155                 160                 165
Ile Ile Pro Glu Gly Leu Lys Lys Val Leu Ser Gln Trp Lys Pro
               170                 175                 180
Glu Asp Ser Lys Asp Pro Thr Lys Arg Thr Pro Lys Phe Leu Tyr
               185                 190                 195
Thr Ile Pro Asn Gly Asn Asn Pro Thr Gly Asn Ser Leu Thr Gly
               200                 205                 210
Asp Arg Lys Lys Glu Ile Tyr Glu Leu Ala Arg Lys Tyr Asp Phe
               215                 220                 225
Leu Ile Ile Glu Asp Asp Pro Tyr Tyr Phe Leu Gln Phe Thr Lys
               230                 235                 240
Pro Trp Glu Pro Thr Phe Leu Ser Met Asp Val Asp Gly Arg Val
               245                 250                 255
Ile Arg Ala Asp Ser Leu Ser Lys Val Ile Ser Ser Gly Leu Arg
               260                 265                 270
```

-continued

```
Val Gly Phe Ile Thr Gly Pro Lys Ser Leu Ile Gln Arg Ile Val
                275                 280                 285

Leu His Thr Gln Ile Ser Ser Leu His Pro Cys Thr Leu Ser Gln
                290                 295                 300

Leu Met Ile Ser Glu Leu Leu Tyr Gln Trp Gly Glu Gly Phe
                305                 310                 315

Leu Ala His Val Asp Arg Ala Ile Asp Phe Tyr Lys Asn Gln Arg
                320                 325                 330

Asp Phe Ile Leu Ala Ala Asp Lys Trp Leu Arg Gly Leu Ala
                335                 340                 345

Glu Trp His Val Pro Lys Ala Gly Met Phe Leu Trp Ile Lys Val
                350                 355                 360

Asn Gly Ile Ser Asp Ala Lys Lys Leu Ile Glu Glu Lys Ala Ile
                365                 370                 375

Glu Arg Glu Ile Leu Leu Val Pro Gly Asn Ser Phe Phe Val Asp
                380                 385                 390

Asn Ser Ala Pro Ser Ser Phe Phe Arg Ala Ser Phe Ser Gln Val
                395                 400                 405

Thr Pro Ala Gln Met Asp Leu Val Phe Gln Arg Leu Ala Gln Leu
                410                 415                 420

Ile Lys Asp Val Ser
                425
```

(2) INFORMATION FOR SEQ ID NO: 32:

(i) SEQUENCE CHARACTERISTICS:
        (A) LENGTH: 343 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: GI 1808648

(xi) SEQUENCE DESCRIPTION: SEQ ID NO: 32:

```
Met Glu Val Ser Cys Gly Gln Ala Glu Ser Ser Glu Lys Pro Asn
                5                   10                  15

Ala Glu Asp Met Thr Ser Lys Asp Tyr Tyr Phe Asp Ser Tyr Ala
                20                  25                  30

His Phe Gly Ile His Glu Glu Met Leu Lys Asp Glu Val Arg Thr
                35                  40                  45

Leu Thr Tyr Arg Asn Ser Met Phe His Asn Arg His Leu Phe Lys
                50                  55                  60

Asp Lys Val Val Leu Asp Val Gly Ser Gly Thr Gly Ile Leu Cys
                65                  70                  75

Met Phe Ala Ala Lys Ala Gly Ala Arg Lys Val Ile Gly Ile Val
                80                  85                  90

Cys Ser Ser Ile Ser Asp Tyr Ala Val Lys Ile Val Lys Ala Asn
                95                  100                 105

Lys Leu Asp His Val Val Thr Ile Ile Lys Gly Lys Val Glu Glu
                110                 115                 120

Val Glu Leu Pro Val Glu Lys Val Asp Ile Ile Ile Ser Glu Trp
                125                 130                 135

Met Gly Tyr Cys Leu Phe Tyr Glu Ser Met Leu Asn Thr Val Leu
                140                 145                 150

Tyr Ala Arg Asp Lys Trp Leu Ala Pro Asp Gly Leu Ile Phe Pro
```

-continued

```
                155                 160                 165
Asp Arg Ala Thr Leu Tyr Val Thr Ala Ile Glu Asp Arg Gln Tyr
                170                 175                 180

Lys Asp Tyr Lys Ile His Trp Trp Glu Asn Val Tyr Gly Phe Asp
                185                 190                 195

Met Ser Cys Ile Lys Asp Val Ala Ile Lys Glu Pro Leu Val Asp
                200                 205                 210

Val Val Asp Pro Lys Gln Leu Val Thr Asn Ala Cys Leu Ile Lys
                215                 220                 225

Glu Val Asp Ile Tyr Thr Val Lys Val Glu Asp Leu Thr Phe Thr
                230                 235                 240

Ser Pro Phe Cys Leu Gln Val Lys Arg Asn Asp Tyr Val His Ala
                245                 250                 255

Leu Val Ala Tyr Phe Asn Ile Glu Phe Thr Arg Cys His Lys Arg
                260                 265                 270

Thr Gly Phe Ser Thr Ser Pro Glu Ser Pro Tyr Thr His Trp Lys
                275                 280                 285

Gln Thr Val Phe Tyr Met Glu Asp Tyr Leu Thr Val Lys Thr Gly
                290                 295                 300

Glu Glu Ile Phe Gly Thr Ile Gly Met Arg Pro Asn Ala Lys Asn
                305                 310                 315

Asn Arg Asp Leu Asp Phe Thr Ile Asp Leu Asp Phe Lys Gly Gln
                320                 325                 330

Leu Cys Glu Leu Ser Cys Ser Thr Asp Tyr Arg Met Arg
                335                 340
```

HUMAN TRANSFERASES

FIELD OF THE INVENTION

This invention relates to nucleic acid and amino acid sequences of human transferases and to the use of these sequences in the diagnosis, treatment, and prevention of autoimmune/inflammatory, neurological, reproductive, and gastrointestinal disorders and cancer.

BACKGROUND OF THE INVENTION

Transferases, enzymes that catalyze group transfer reactions, are classified by the type of group transferred. One-carbon groups are transferred; for example, methyltransferases transfer methyl groups from S-adenosylmethionine to substrates. Nitrogenous groups are transferred; for example, aminotransferases transfer amino groups. Other groups transferred include aldehyde or ketone, acyl, glycosyl, alkyl and aryl other than methyl, phosphorus-containing, sulfur-containing, and selenium-containing groups.

The enzyme glutamine-phenylpyruvate aminotransferase, also known as glutamine transaminase K (GTK), catalyzes several reactions with a pyridoxal phosphate cofactor. GTK catalyzes the reversible conversion of L-glutamine and phenylpyruvate to 2-oxoglutaramate and L-phenylalanine. L-methionine, L-histidine, and L-tyrosine can substitute for L-glutamine in this reaction. GTK also catalyzes the conversion of kynurenine to kynurenic acid. Kynurenic acid, a tryptophan metabolite, is an antagonist of the N-methyl-D-aspartate (NMDA) receptor in the brain and may exert a neuromodulatory function. Alteration of the kynurenine metabolic pathway may be among the causative factors leading to several neurological disorders. GTK also possesses cysteine conjugate β-lyase activity which is involved in the metabolism of halogenated xenobiotics conjugated to glutathione. GTK action on the cysteine conjugates of xenobiotics yields metabolites that are nephrotoxic in rats and neurotoxic in humans. The neurotoxicity may be related to the kynurenine aminotransferase activity of GTK. GTK is expressed in kidney, liver, and brain. Both cytosolic and mitochondrial forms exist. Human and rat GTK genes have been isolated which encode proteins of 422 and 423 amino acids respectively. Both human and rat GTKs contain a putative pyridoxal phosphate binding site. (ExPASy ENZYME: EC 2.6.1.64; Perry, S. J. et al. (1993) Mol. Pharmacol. 43:660–665; Perry, S. et al. (1995) FEBS Lett. 360:277–280; and Alberati-Giani, D. et al. (1995) J. Neurochem. 64:1448–1455.)

The enzyme kynurenine/α-aminoadipate aminotransferase (AadAT) catalyzes two reactions with a pyridoxal phosphate cofactor. AadAT catalyzes the reversible conversion of α-aminoadipate and α-ketoglutarate to α-ketoadipate and L-glutamate. This conversion is involved in lysine metabolism. AadAT also catalyzes the transamination of kynurenine acid to kynurenic acid. As described above, kynurenic acid is an NMDA receptor antagonist. Both soluble and mitochondrial forms of AadAT have been purified. A soluble AadAT is expressed in rat kidney, liver, and brain. The rat AadAT nucleotide gene encodes a protein of 425 amino acids which contains a putative pyridoxal phosphate binding site. (Nakatani, Y. et al. (1970) Biochim. Biophys. Acta 198:219–228; Buchli, R. et al. (1995) J. Biol. Chem. 270:29330–29335.)

Protein-arginine methyltransferases catalyze the post-translational methylation of arginine residues in proteins, resulting in the mono- and dimethylation of arginine on the guanidino group. Known substrates are histones, heterogeneous nuclear ribonucleoproteins (hnRNPs), and myelin basic protein. This otherwise unusual posttranslational modification is common in hnRNPs and may regulate their function. hnRNPs function in the nucleus in mRNA processing, splicing, and transport into the cytoplasm. Homologous protein-arginine methyltransferases that methylate hnRNPs have been cloned from yeast, rat, and man. These protein-arginine methyltransferases contain five sequence motifs, termed region I, post-region I, region II, region III, and post-region III, that may be involved in binding S-adenosyl-methionine. One human gene (HRMT1L1) encodes a 433 amino acid protein. The other human gene (HRMT1L2) may be alternatively spliced to yield three protein-arginine methyltransferases, of length 343, 347, and 361 amino acids respectively, with different amino termini. The protein encoded by the cloned rat protein-arginine methyltransferase gene (PRMT1) interacts with the TIS21 protein and the homologous BTG1 protein. The intermediate-early TIS21 protein is the product of a gene induced by treatment of cells with mitogens such as epidermal growth factor, and the BTG1 protein is the product of a human gene located near a chromosome translocation breakpoint associated with chronic lymphocytic leukemia. The HRMT 1L2 protein interacts with the cytoplasmic domain of the interferon receptor. This interaction suggests that protein methylation may be an important signaling mechanism for cytokine receptors. (Lin, W.-J. et al. (1996) J. Biol. Chem. 271:15034–15044; Abramovich, C. et al. (1997) EMBO J. 16:260–266; and Scott, H. S. et al. (1998) Genomics 48:330–340.)

The discovery of new human transferases and the polynucleotides encoding them satisfies a need in the art by providing new compositions which are useful in the diagnosis, treatment, and prevention of autoimmune/inflammatory, neurological, reproductive, and gastrointestinal disorders and cancer.

SUMMARY OF THE INVENTION

The invention features substantially purified polypeptides, human transferases, referred to collectively as "HUTRAN" and individually as "HUTRAN-1", "HUTRAN-2", and "HUTRAN-3.". In one aspect, the invention provides a substantially purified polypeptide comprising an amino acid sequence selected from the group consisting of SEQ ID NO:1, SEQ ID NO:2, and SEQ ID NO:3 (SEQ ID NO:1–3) and fragments thereof.

The invention further provides a substantially purified variant having at least 90% amino acid identity to the amino acid sequences of SEQ ID NO:1–3 or to fragments of any of these sequences. The invention also provides an isolated and purified polynucleotide encoding the polypeptide comprising an amino acid sequence selected from the group consisting of SEQ ID NO:1–3 and fragments thereof. The invention also includes an isolated and purified polynucleotide variant having at least 70% polynucleotide sequence identity to the polynucleotide encoding the polypeptide comprising an amino acid sequence selected from the group consisting of SEQ ID NO:1–3 and fragments thereof.

Additionally, the invention provides an isolated and purified polynucleotide which hybridizes under stringent conditions to the polynucleotide encoding the polypeptide comprising an amino acid sequence selected from the group consisting of SEQ ID NO:1–3 and fragments thereof, as well as an isolated and purified polynucleotide having a sequence which is complementary to the polynucleotide encoding the polypeptide comprising the amino acid sequence selected from the group consisting of SEQ ID NO:1–3 and fragments thereof.

The invention also provides an isolated and purified polynucleotide comprising a polynucleotide sequence selected from the group consisting of SEQ ID NO:4, SEQ ID NO:5, and SEQ ID NO:6 (SEQ ID NO:4–6), and fragments thereof. The invention further provides an isolated and purified polynucleotide variant having at least 70% polynucleotide sequence identity to the polynucleotide sequence comprising a polynucleotide sequence selected from the group consisting of SEQ ID NO:4–6 and fragments thereof, as well as an isolated and purified polynucleotide having a sequence which is complementary to the polynucleotide comprising a polynucleotide sequence selected from the group consisting of SEQ ID NO:4–6 and fragments thereof.

The invention further provides an expression vector containing at least a fragment of the polynucleotide encoding the polypeptide comprising an amino acid sequence selected from the group consisting of SEQ ID NO:1–3 and fragments thereof. In another aspect, the expression vector is contained within a host cell.

The invention also provides a method for producing a polypeptide comprising the amino acid sequence selected from the group consisting of SEQ ID NO:1–3 and fragments thereof, the method comprising the steps of: (a) culturing the host cell containing an expression vector containing at least a fragment of a polynucleotide encoding the polypeptide under conditions suitable for the expression of the polypeptide; and (b) recovering the polypeptide from the host cell culture.

The invention also provides a pharmaceutical composition comprising a substantially purified polypeptide having the amino acid sequence selected from the group consisting of SEQ ID NO:1–3 and fragments thereof in conjunction with a suitable pharmaceutical carrier.

The invention further includes a purified antibody which binds to a polypeptide comprising the amino acid sequence selected from the group consisting of SEQ ID NO:1–3 and fragments thereof, as well as a purified agonist and a purified antagonist to the polypeptide. The invention also provides a method for treating or preventing an autoimmune/inflammatory disorder, the method comprising administering to a subject in need of such treatment an effective amount of an antagonist of the polypeptide having an amino acid sequence selected from the group consisting of SEQ ID NO:1–3 and fragments thereof.

The invention also provides a method for treating or preventing a neurological disorder, the method comprising administering to a subject in need of such treatment an effective amount of a pharmaceutical composition comprising a substantially purified polypeptide having an amino acid sequence selected from the group consisting of SEQ ID NO:1–3 and fragments thereof.

The invention also provides a method for treating or preventing a reproductive disorder, the method comprising administering to a subject in need of such treatment an effective amount of a pharmaceutical composition comprising a substantially purified polypeptide having an amino acid sequence selected from the group consisting of SEQ ID NO:1–3 and fragments thereof.

The invention also provides a method for treating or preventing a gastrointestinal disorder, the method comprising administering to a subject in need of such treatment an effective amount of a pharmaceutical composition comprising a substantially purified polypeptide having an amino acid sequence selected from the group consisting of SEQ ID NO:1–3 and fragments thereof.

The invention also provides a method for treating or preventing a cancer, the method comprising administering to a subject in need of such treatment an effective amount of an antagonist of the polypeptide having an amino acid sequence selected from the group consisting of SEQ ID NO:1–3 and fragments thereof.

The invention also provides a method for detecting a polynucleotide encoding the polypeptide comprising the amino acid sequence selected from the group consisting of SEQ ID NO:1–3 and fragments thereof in a biological sample containing nucleic acids, the method comprising the steps of: (a) hybridizing the complement of the polynucleotide sequence encoding the polypeptide comprising the amino acid sequence selected from the group consisting of SEQ ID NO:1–3 and fragments thereof to at least one of the nucleic acids of the biological sample, thereby forming a hybridization complex; and (b) detecting the hybridization complex, wherein the presence of the hybridization complex correlates with the presence of a polynucleotide encoding the polypeptide in the biological sample. In one aspect, the method further comprises amplifying the polynucleotide prior to the hybridizing step.

BRIEF DESCRIPTION OF THE FIGURES AND TABLES

Figure 1A:
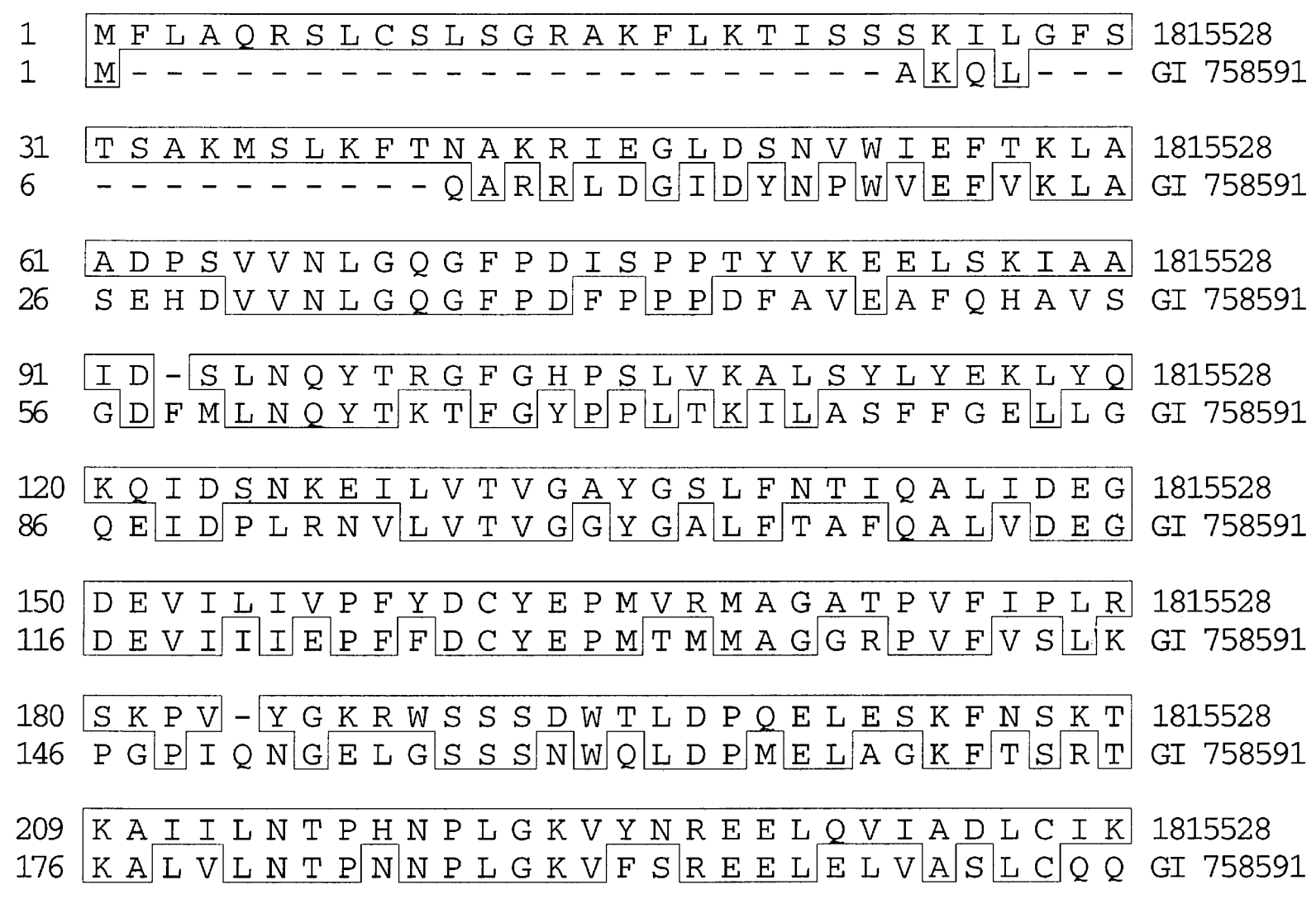
Figure 1B:
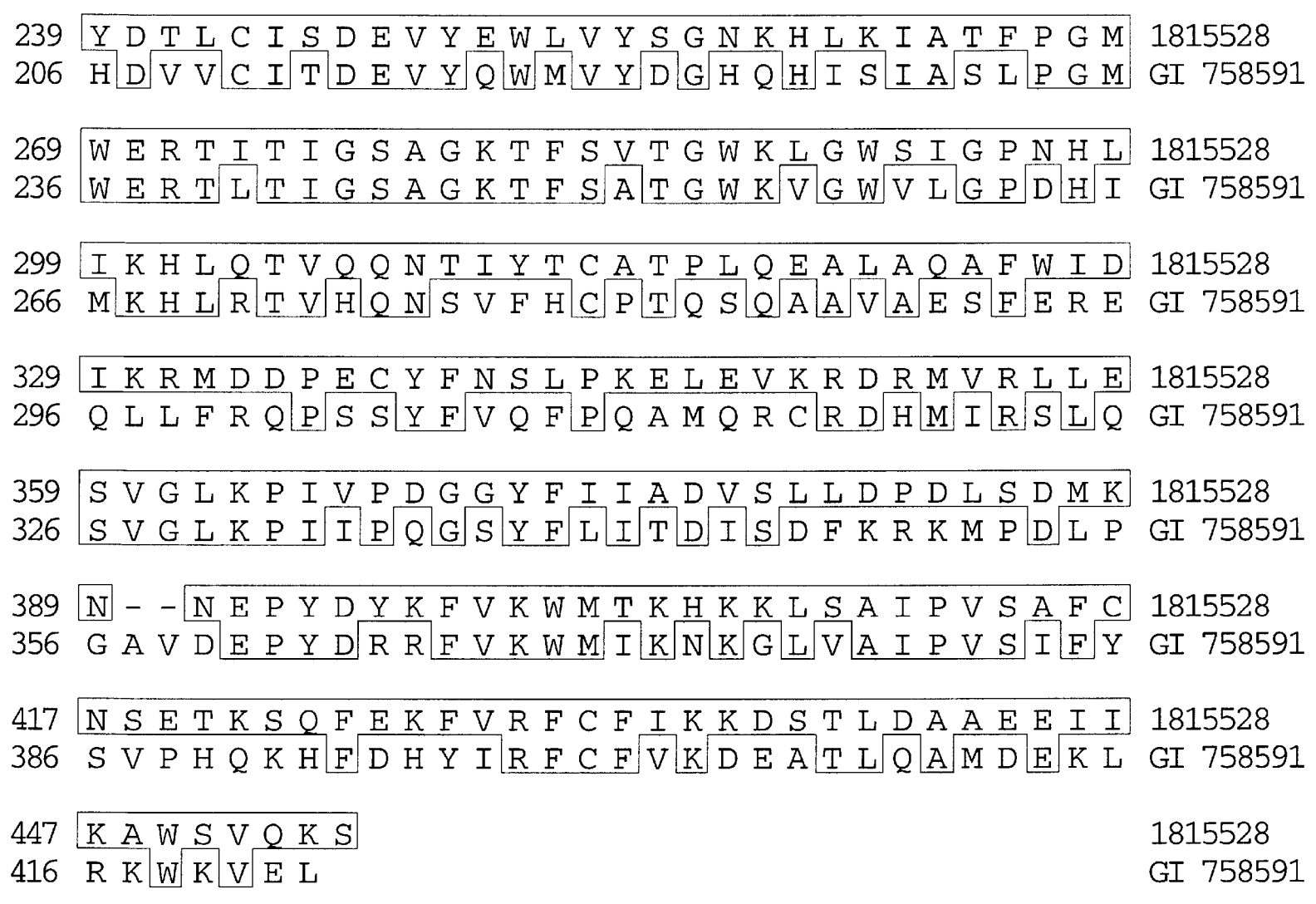

FIGS. 1A and 1B show the amino acid sequence alignment between HUTRAN-1 (1815528; SEQ ID NO:1) and human glutamine-phenylpyruvate aminotransferase (GI 758591; SEQ ID NO:30), produced using the multisequence alignment program of LASERGENE™ software (DNASTAR Inc, Madison Wis.).

Figure 2A:
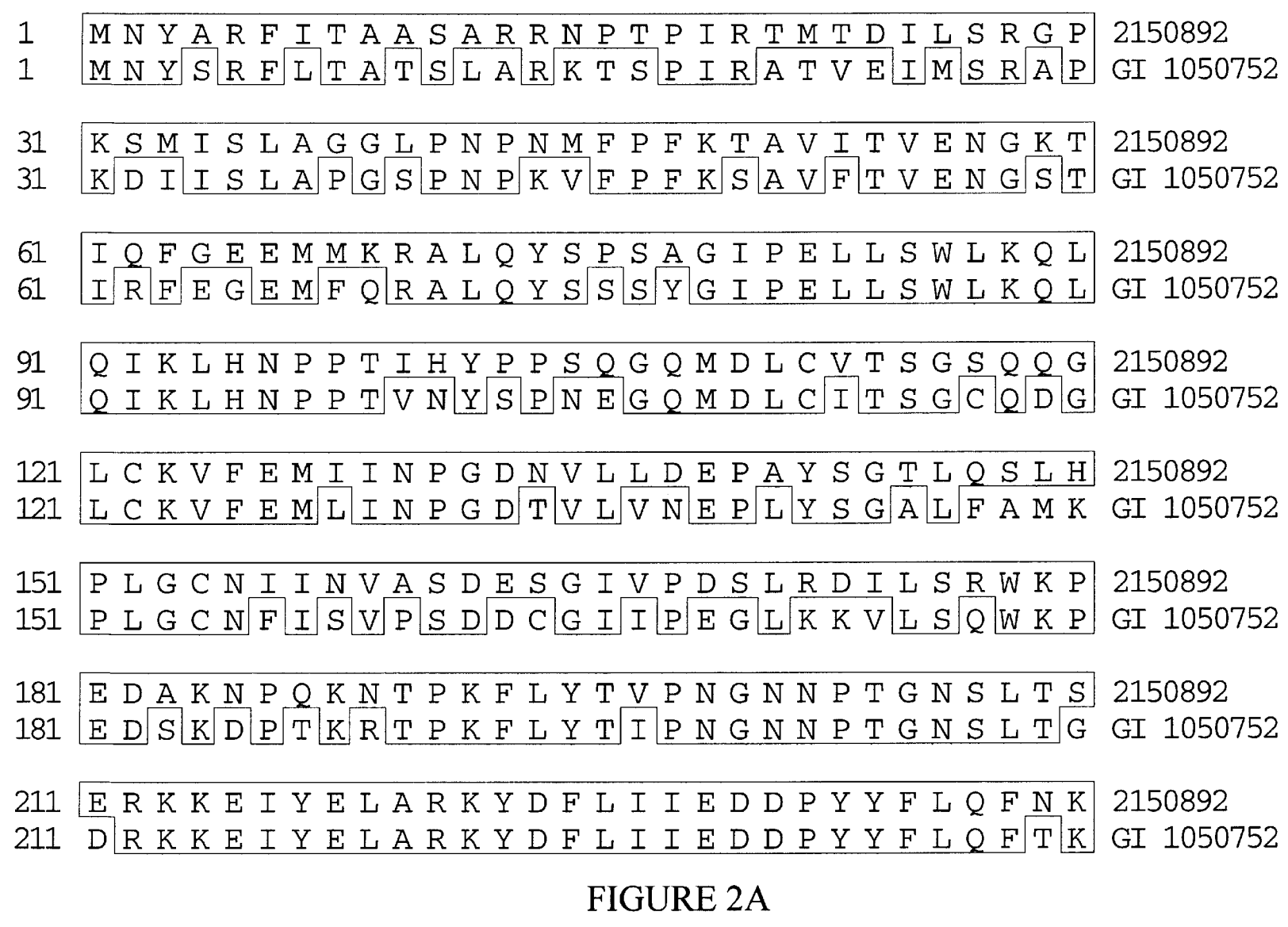
Figure 2B:
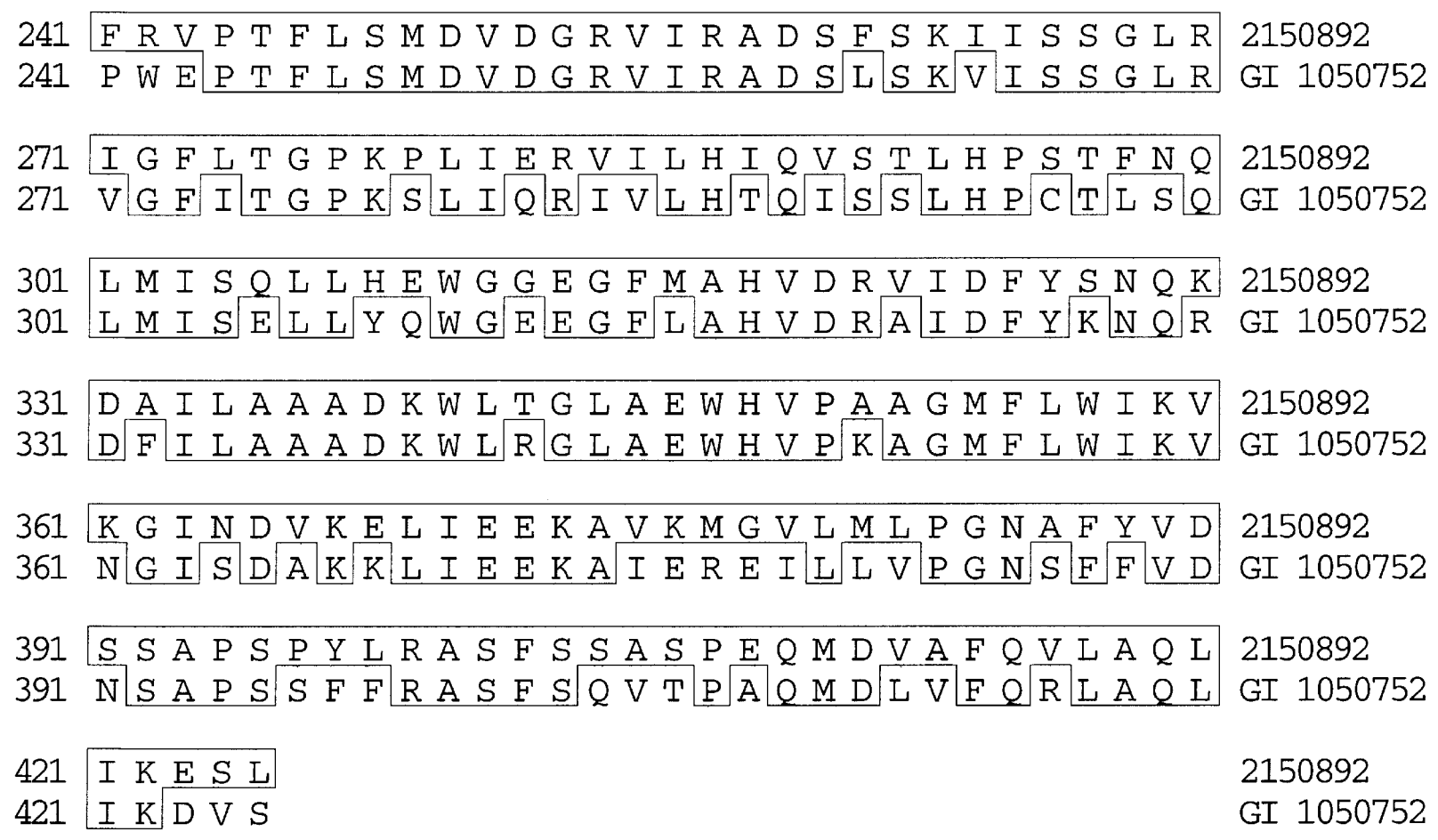

FIGS. 2A and 2B show the amino acid sequence alignment between HUTRAN-2 (2150892; SEQ ID NO:2) and rat kynurenine/α-aminoadipate aminotransferase (GI 1050752; SEQ ID NO:31).

Figure 3A:
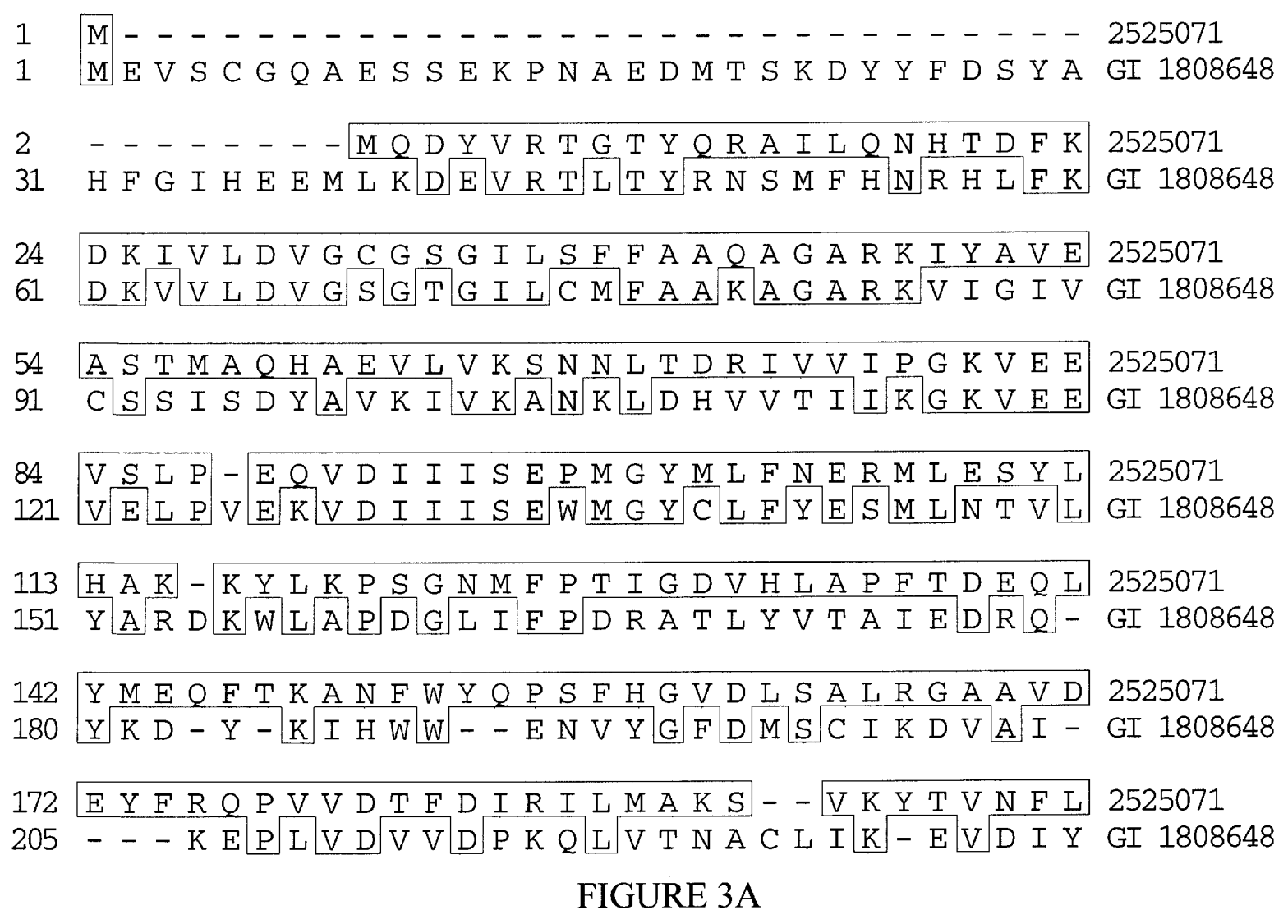

FIGS. 3A, 3B, and 3C show the amino acid sequence alignment between HUTRAN-3 (2525071; SEQ ID NO:3) and human arginine methyltransferase (GI 1808648; SEQ ID NO:32).

In Table 1, columns 1 and 2 show the sequence identification numbers (SEQ ID NO:) of the amino acid and nucleic acid sequence, respectively. Column 3 shows the Clone ID of the Incyte Clone in which nucleic acids encoding each HUTRAN were first identified, and column 4, the cDNA library of this clone. Column 5 shows the Incyte clones (and libraries) and shotgun sequences useful as fragments in hybridization technologies, and which are part of the consensus nucleotide sequence of each HUTRAN.

Table 2 shows various properties of the polypeptides of the invention: column 1 references the SEQ ID NO; column 2 shows the number of amino acid residues; column 3, potential phosphorylation sites; column 4, potential glycosylation sites; column 5, signature sequences associated with known proteins; column 6, the identity of the protein; and column 7, analytical methods used to identify the protein through sequence homologies, protein motifs, and protein signatures.

Table 3 shows the tissue expression of each nucleic acid sequence by northern analysis, diseases or conditions associated with this tissue expression, and the vector into which each cDNA was cloned.

Table 4 describes the tissues used in cDNA library construction.

Table 5 describes the programs, algorithms, databases, and qualifying scores used to analyze HUTRAN. The first column of Table 5 shows the tool, program, or algorithm; the second column, the database; the third column, a brief description; and the fourth column (where applicable), scores for determining the strength of a match between two sequences (the higher the value, the more homologous).

DESCRIPTION OF THE INVENTION

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are cited for the purpose of describing and disclosing the cell lines, vectors, and methodologies which are reported in the publications and which might be used in connection with the invention. Nothing herein is to be construed as an admission that the invention is not entitled to antedate such disclosure by virtue of prior invention.

Definitions

"HUTRAN," as used herein, refers to the amino acid sequences of substantially purified HUTRAN obtained from any species, particularly a mammalian species, including bovine, ovine, porcine, murine, equine, and preferably the human species, from any source, whether natural, synthetic, semi-synthetic, or recombinant.

The term "agonist," as used herein, refers to a molecule which, when bound to HUTRAN, increases or prolongs the duration of the effect of HUTRAN. Agonists may include proteins, nucleic acids, carbohydrates, or any other molecules which bind to and modulate the effect of HUTRAN.

An "allelic variant," as this term is used herein, is an alternative form of the gene encoding HUTRAN. Allelic variants may result from at least one mutation in the nucleic acid sequence and may result in altered mRNAs or in polypeptides whose structure or function may or may not be altered. Any given natural or recombinant gene may have none, one, or many allelic forms. Common mutational changes which give rise to allelic variants are generally ascribed to natural deletions, additions, or substitutions of nucleotides. Each of these types of changes may occur alone, or in combination with the others, one or more times in a given sequence.

"Altered" nucleic acid sequences encoding HUTRAN, as described herein, include those sequences with deletions, insertions, or substitutions of different nucleotides, resulting in a polynucleotide the same as HUTRAN or a polypeptide with at least one functional characteristic of HUTRAN. Included within this definition are polymorphisms which may or may not be readily detectable using a particular oligonucleotide probe of the polynucleotide encoding HUTRAN, and improper or unexpected hybridization to allelic variants, with a locus other than the normal chromosomal locus for the polynucleotide sequence encoding HUTRAN. The encoded protein may also be "altered," and may contain deletions, insertions, or substitutions of amino acid residues which produce a silent change and result in a functionally equivalent HUTRAN. Deliberate amino acid substitutions may be made on the basis of similarity in polarity, charge, solubility, hydrophobicity, hydrophilicity, and/or the amphipathic nature of the residues, as long as the biological or immunological activity of HUTRAN is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine.

The terms "amino acid" or "amino acid sequence," as used herein, refer to an oligopeptide, peptide, polypeptide, or protein sequence, or a fragment of any of these, and to naturally occurring or synthetic molecules. In this context, "fragments," "immunogenic fragments," or "antigenic fragments" refer to fragments of HUTRAN which are preferably at least 5 to about 15 amino acids in length, most preferably at least 14 amino acids, and which retain some biological activity or immunological activity of HUTRAN. Where "amino acid sequence" is recited herein to refer to an amino acid sequence of a naturally occurring protein molecule, "amino acid sequence" and like terms are not meant to limit the amino acid sequence to the complete native amino acid sequence associated with the recited protein molecule.

"Amplification," as used herein, relates to the production of additional copies of a nucleic acid sequence. Amplification is generally carried out using polymerase chain reaction (PCR) technologies well known in the art. (See, e.g., Dieffenbach, C. W. and G. S. Dveksler (1995) *PCR Primer, a Laboratory Manual,* Cold Spring Harbor Press, Plainview, N.Y., pp.1–5.)

The term "antagonist," as it is used herein, refers to a molecule which, when bound to HUTRAN, decreases the amount or the duration of the effect of the biological or immunological activity of HUTRAN. Antagonists may include proteins, nucleic acids, carbohydrates, antibodies, or any other molecules which decrease the effect of HUTRAN.

As used herein, the term "antibody" refers to intact molecules as well as to fragments thereof, such as Fab, F(ab')$_2$, and Fv fragments, which are capable of binding the epitopic determinant. Antibodies that bind HUTRAN polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant," as used herein, refers to that fragment of a molecule (i.e., an epitope) that makes contact with a particular antibody. When a protein or a fragment of a protein is used to immunize a host animal, numerous regions of the protein may induce the production of antibodies which bind specifically to antigenic determinants (given regions or three-dimensional structures on the protein). An antigenic determinant may compete with the intact antigen (i.e., the immunogen used to elicit the immune response) for binding to an antibody.

The term "antisense," as used herein, refers to any composition containing a nucleic acid sequence which is complementary to the "sense" strand of a specific nucleic acid sequence. Antisense molecules may be produced by any method including synthesis or transcription. Once introduced into a cell, the complementary nucleotides combine with natural sequences produced by the cell to form duplexes and to block either transcription or translation. The designation "negative" can refer to the antisense strand, and the designation "positive" can refer to the sense strand.

As used herein, the term "biologically active," refers to a protein having structural, regulatory, or biochemical functions of a naturally occurring molecule. Likewise, "immunologically active" refers to the capability of the natural, recombinant, or synthetic HUTRAN, or of any oligopeptide thereof, to induce a specific immune response in appropriate animals or cells and to bind with specific antibodies.

The terms "complementary" or "complementarity," as used herein, refer to the natural binding of polynucleotides by base pairing. For example, the sequence "5' A-G-T 3'" binds to the complementary sequence "3'T-C-A5'." Complementarity between two single-stranded molecules may be "partial," such that only some of the nucleic acids bind, or it may be "complete," such that total complementarity exists between the single stranded molecules. The degree of complementarity between nucleic acid strands has significant effects on the efficiency and strength of the hybridization between the nucleic acid strands. This is of particular importance in amplification reactions, which depend upon binding between nucleic acids strands, and in the design and use of peptide nucleic acid (PNA) molecules.

A "composition comprising a given polynucleotide sequence" or a "composition comprising a given amino acid sequence," as these terms are used herein, refer broadly to any composition containing the given polynucleotide or amino acid sequence. The composition may comprise a dry formulation or an aqueous solution. Compositions comprising polynucleotide sequences encoding HUTRAN or fragments of HUTRAN may be employed as hybridization probes. The probes may be stored in freeze-dried form and may be associated with a stabilizing agent such as a carbohydrate. In hybridizations, the probe may be deployed in an aqueous solution containing salts, e.g., NaCl, detergents, e.g.,sodium dodecyl sulfate (SDS), and other components, e.g., Denhardt's solution, dry milk, salmon sperm DNA, etc.

"Consensus sequence," as used herein, refers to a nucleic acid sequence which has been resequenced to resolve uncalled bases, extended using XL-PCR™ (Perkin Elmer, Norwalk, Conn.) in the 5' and/or the 3' direction, and resequenced, or which has been assembled from the overlapping sequences of more than one Incyte Clone using a computer program for fragment assembly, such as the GELVIEW™ fragment assembly system (GCG, Madison, Wis.). Some sequences have been both extended and assembled to produce the consensus sequence.

As used herein, the term "correlates with expression of a polynucleotide" indicates that the detection of the presence of nucleic acids, the same or related to a nucleic acid sequence encoding HUTRAN, by Northern analysis is indicative of the presence of nucleic acids encoding HUTRAN in a sample, and thereby correlates with expression of the transcript from the polynucleotide encoding HUTRAN.

A "deletion," as the term is used herein, refers to a change in the amino acid or nucleotide sequence that results in the absence of one or more amino acid residues or nucleotides.

The term "derivative," as used herein, refers to the chemical modification of a polypeptide sequence, or a polynucleotide sequence. Chemical modifications of a polynucleotide sequence can include, for example, replacement of hydrogen by an alkyl, acyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

The term "similarity," as used herein, refers to a degree of complementarity. There may be partial similarity or complete similarity. The word "identity" may substitute for the word "similarity." A partially complementary sequence that at least partially inhibits an identical sequence from hybridizing to a target nucleic acid is referred to as "substantially similar." The inhibition of hybridization of the completely complementary sequence to the target sequence may be examined using a hybridization assay (Southern or Northern blot, solution hybridization, and the like) under conditions of reduced stringency. A substantially similar sequence or hybridization probe will compete for and inhibit the binding of a completely similar (identical) sequence to the target sequence under conditions of reduced stringency. This is not to say that conditions of reduced stringency are such that non-specific binding is permitted, as reduced stringency conditions require that the binding of two sequences to one another be a specific (i.e., a selective) interaction. The absence of non-specific binding may be tested by the use of a second target sequence which lacks even a partial degree of complementarity (e.g., less than about 30% similarity or identity). In the absence of non-specific binding, the substantially similar sequence or probe will not hybridize to the second non-complementary target sequence.

The phrases "percent identity" or "% identity" refer to the percentage of sequence similarity found in a comparison of two or more amino acid or nucleic acid sequences. Percent identity can be determined electronically, e.g., by using the MegAlign™ program (DNASTAR, Inc., Madison Wis.). The MegAlign™ program can create alignments between two or more sequences according to different methods, e.g., the clustal method. (See, e.g., Higgins, D. G. and P. M. Sharp (1988) Gene 73:237–244.) The clustal algorithm groups sequences into clusters by examining the distances between all pairs. The clusters are aligned pairwise and then in groups. The percentage similarity between two amino acid sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no similarity between the two amino acid sequences are not included in determining percentage similarity. Percent identity between nucleic acid sequences can also be counted or calculated by other methods known in the art, e.g., the Jotun Hein method. (See, e.g., Hein, J. (1990) Methods Enzymol. 183:626–645.) Identity between sequences can also be determined by other methods known in the art, e.g., by varying hybridization conditions.

"Human artificial chromosomes" (HACs), as described herein, are linear microchromosomes which may contain DNA sequences of about 6 kb to 10 Mb in size, and which contain all of the elements required for stable mitotic chromosome segregation and maintenance. (See, e.g., Harrington, J. J. et al. (1997) Nat Genet. 15:345–355.)

The term "humanized antibody," as used herein, refers to antibody molecules in which the amino acid sequence in the non-antigen binding regions has been altered so that the antibody more closely resembles a human antibody, and still retains its original binding ability.

"Hybridization," as the term is used herein, refers to any process by which a strand of nucleic acid binds with a complementary strand through base pairing.

As used herein, the term "hybridization complex" refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The words "insertion" or "addition," as used herein, refer to changes in an amino acid or nucleotide sequence resulting in the addition of one or more amino acid residues or nucleotides, respectively, to the sequence found in the naturally occurring molecule.

"Immune response" can refer to conditions associated with inflammation, trauma, immune disorders, or infectious or genetic disease, etc. These conditions can be characterized by expression of various factors, e.g., cytokines, chemokines, and other signaling molecules, which may affect cellular and systemic defense systems.

The term "microarray," as used herein, refers to an arrangement of distinct polynucleotides arrayed on a substrate, e.g., paper, nylon or any other type of membrane, filter, chip, glass slide, or any other suitable solid support.

The terms "element" or "array element" as used herein in a microarray context, refer to hybridizable polynucleotides arranged on the surface of a substrate.

The term "modulate," as it appears herein, refers to a change in the activity of HUTRAN. For example, modulation may cause an increase or a decrease in protein activity, binding characteristics, or any other biological, functional, or immunological properties of HUTRAN.

The phrases "nucleic acid" or "nucleic acid sequence," as used herein, refer to a nucleotide, oligonucleotide, polynucleotide, or any fragment thereof. These phrases also refer to DNA or RNA of genomic or synthetic origin which may be single-stranded or double-stranded and may represent the sense or the antisense strand, to peptide nucleic acid (PNA), or to any DNA-like or RNA-like material. In this context, "fragments" refers to those nucleic acid sequences which, when translated, would produce polypeptides retaining some functional characteristic, e.g., antigenicity, or structural domain characteristic, e.g., ATP-binding site, of the full-length polypeptide.

The terms "operably associated" or "operably linked," as used herein, refer to functionally related nucleic acid sequences. A promoter is operably associated or operably linked with a coding sequence if the promoter controls the translation of the encoded polypeptide. While operably associated or operably linked nucleic acid sequences can be contiguous and in the same reading frame, certain genetic elements, e.g., repressor genes, are not contiguously linked to the sequence encoding the polypeptide but still bind to operator sequences that control expression of the polypeptide.

The term "oligonucleotide," as used herein, refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay or microarray. As used herein, the term "oligonucleotide" is substantially equivalent to the terms "amplimer," "primer," "oligomer," and "probe," as these terms are commonly defined in the art.

"Peptide nucleic acid" (PNA), as used herein, refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA or RNA and stop transcript elongation, and may be pegylated to extend their lifespan in the cell. (See, e.g., Nielsen, P. E. et al. (1993) Anticancer Drug Des. 8:53–63.)

The term "sample," as used herein, is used in its broadest sense. A biological sample suspected of containing nucleic acids encoding HUTRAN, or fragments thereof, or HUTRAN itself, may comprise a bodily fluid; an extract from a cell, chromosome, organelle, or membrane isolated from a cell; a cell; genomic DNA, RNA, or cDNA, in solution or bound to a solid support; a tissue; a tissue print; etc.

As used herein, the terms "specific binding" or "specifically binding" refer to that interaction between a protein or peptide and an agonist, an antibody, or an antagonist. The interaction is dependent upon the presence of a particular structure of the protein, e.g., the antigenic determinant or epitope, recognized by the binding molecule. For example, if an antibody is specific for epitope "A," the presence of a polypeptide containing the epitope A, or the presence of free unlabeled A, in a reaction containing free labeled A and the antibody will reduce the amount of labeled A that binds to the antibody.

As used herein, the term "stringent conditions" refers to conditions which permit hybridization between polynucleotides and the claimed polynucleotides. Stringent conditions can be defined by salt concentration, the concentration of organic solvent, e.g., formamide, temperature, and other conditions well known in the art. In particular, stringency can be increased by reducing the concentration of salt, increasing the concentration of formamide, or raising the hybridization temperature.

The term "substantially purified," as used herein, refers to nucleic acid or amino acid sequences that are removed from their natural environment and are isolated or separated, and are at least about 60% free, preferably about 75% free, and most preferably about 90% free from other components with which they are naturally associated.

A "substitution," as used herein, refers to the replacement of one or more amino acids or nucleotides by different amino acids or nucleotides, respectively.

"Transformation," as defined herein, describes a process by which exogenous DNA enters and changes a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, viral infection, electroporation, heat shock, lipofection, and particle bombardment. The term "transformed" cells includes stably transformed cells in which the inserted DNA is capable of replication either as an autonomously replicating plasmid or as part of the host chromosome, as well as transiently transformed cells which express the inserted DNA or RNA for limited periods of time.

A "variant" of HUTRAN polypeptides, as used herein, refers to an amino acid sequence that is altered by one or more amino acid residues. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, LASERGENE™ software.

The term "variant," when used in the context of a polynucleotide sequence, may encompass a polynucleotide sequence related to HUTRAN. This definition may also include, for example, "allelic" (as defined above), "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs) in which the polynucleotide sequence varies by one base. The presence of SNPs may be indicative of, for example, a certain population, a disease state, or a propensity for a disease state.

The Invention

The invention is based on the discovery of three new human transferases (HUTRAN), the polynucleotides encoding HUTRAN, and the use of these compositions for the diagnosis, treatment, or prevention of autoimmune/inflammatory, neurological, reproductive, and gastrointestinal disorders and cancer. Table 1 summarizes the sequence identification numbers, identifying clone numbers, and libraries of HUTRAN.

As shown in Table 2, each HUTRAN has been characterized with regard to its chemical and structural similarity with transferase molecules. As shown in FIGS. 1A and 1B, HUTRAN-1 and human glutamine-phenylpyruvate aminotransferase (GI 758591; SEQ ID NO:30) share 49% identity. As shown in FIGS. 2A and 2B, HUTRAN-2 and rat kynurenine/α-aminoadipate aminotransferase (GI 1050752; SEQ ID NO:31) share 71% identity. As shown in FIGS. 3A, 3B, and 3C, HUTRAN-3 and human arginine methyltransferase (GI 1808648; SEQ ID NO:32) share 27% identity.

In Table 3, northern analysis shows the expression of HUTRAN sequences in various libraries, of which at least 42% are immortalized or cancerous, at least 18% are in fetal or proliferating tissue, at least 9% involve trauma, and at least 14% involve immune response. Of particular note is the expression of HUTRAN in male and female reproductive, nervous, and gastrointestinal tissues.

A preferred HUTRAN variant is one which has at least about 80%, more preferably at least about 90%, and most preferably at least about 95% amino acid sequence identity to the HUTRAN amino acid sequence, and which contains at least one functional or structural characteristic of HUTRAN.

The invention also encompasses polynucleotides which encode HUTRAN. In a particular embodiment, the invention encompasses a polynucleotide sequence comprising the sequence of SEQ ID NO:4, which encodes a HUTRAN. In a further embodiment, the invention encompasses the polynucleotide sequence comprising the sequence of SEQ ID NO:5. In a further embodiment, the invention encompasses the polynucleotide sequence comprising the sequence of SEQ ID NO:6.

The invention also encompasses a variant of a polynucleotide sequence encoding HUTRAN. In particular, such a variant polynucleotide sequence will have at least about 70%, more preferably at least about 85%, and most preferably at least about 95% polynucleotide sequence identity to the polynucleotide sequence encoding HUTRAN. Any one of the polynucleotide variants described above can encode an amino acid sequence which contains at least one functional or structural characteristic of HUTRAN.

It will be appreciated by those skilled in the art that as a result of the degeneracy of the genetic code, a multitude of polynucleotide sequences encoding HUTRAN, some bearing minimal similarity to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring HUTRAN, and all such variations are to be considered as being specifically disclosed.

Although nucleotide sequences which encode HUTRAN and its variants are preferably capable of hybridizing to the nucleotide sequence of the naturally occurring HUTRAN under appropriately selected conditions of stringency, it may be advantageous to produce nucleotide sequences encoding HUTRAN or its derivatives possessing a substantially different codon usage, e.g., inclusion of non-naturally occurring codons. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding HUTRAN and its derivatives without altering the encoded amino acid sequences include the production of RNA transcripts having more desirable properties, such as a greater half-life, than transcripts produced from the naturally occurring sequence.

The invention also encompasses production of DNA sequences which encode HUTRAN and HUTRAN derivatives, or fragments thereof, entirely by synthetic chemistry. After production, the synthetic sequence may be inserted into any of the many available expression vectors and cell systems using reagents well known in the art. Moreover, synthetic chemistry may be used to introduce mutations into a sequence encoding HUTRAN or any fragment thereof.

Also encompassed by the invention are polynucleotide sequences that are capable of hybridizing to the claimed polynucleotide sequences, and, in particular, to those shown in SEQ ID NO:4–6 and fragments thereof under various conditions of stringency. (See, e.g., Wahl, G. M. and S. L. Berger (1987) Methods Enzymol. 152:399–407; Kimmel, A. R. (1987) Methods Enzymol. 152:507–511.) For example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and most preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37+ C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

The washing steps which follow hybridization can also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include temperature of at least about 25° C., more preferably of at least about 42° C., and most preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a most preferred embodiment, wash steps will occur at 68° C. in 15 mM NaCl, 1.5 mM trisodium citrate, and 0.1% SDS. Additional variations on these conditions will be readily apparent to those skilled in the art.

Methods for DNA sequencing and analysis are well known in the art. The methods may employ such enzymes as the Klenow fragment of DNA polymerase I, SEQUENASE® (Amersham Pharmacia Biotech Ltd., Uppsala, Sweden), Taq polymerase (The Perkin-Elmer Corp., Norwalk, Conn.), thermostable T7 polymerase (Amersham Pharmacia Biotech Ltd., Uppsala, Sweden), or combinations of polymerases and proofreading exonucleases, such as those found in the ELONGASE™ amplification system (Life Technologies, Inc., Gaithersburg, Md.). Preferably, sequence preparation is automated with machines, e.g., the ABI CATALYST™ 800 (Perkin Elmer) or MICROLAB® 2200 (Hamilton Co., Reno, Nev.) sequence preparation machines, in combination with thermal cyclers. Sequencing can also be automated, such as by ABIPRISM™ 373 or 377 DNA sequencers (The Perkin-Elmer Corp., Norwalk, Conn.) or the MEGABACE™ 1000 capillary electrophoresis system (Molecular Dynamics, Inc., Sunnyvale, Calif.). Sequences can be analyzed using computer programs and algorithms well known in the art. (See, e.g., Ausubel, supra, unit 7.7; and Meyers, R. A. (1995) *Molecular Biology and Biotechnology*, Wiley VCH, Inc, New York, N.Y.).

The nucleic acid sequences encoding HUTRAN may be extended utilizing a partial nucleotide sequence and employing various PCR-based methods known in the art to detect upstream sequences, such as promoters and regulatory elements. For example, one method which may be employed, restriction-site PCR, uses universal and nested primers to amplify unknown sequence from genomic DNA within a cloning vector. (See, e.g., Sarkar, G. (1993) PCR Methods Applic. 2:318–322.) Another method, inverse PCR, uses primers that extend in divergent directions to amplify unknown sequence from a circularized template. The template is derived from restriction fragments comprising a known genomic locus and surrounding sequences. (See, e.g., Triglia, T. et al. (1988) Nucleic Acids Res. 16:8186.) A third method, capture PCR, involves PCR amplification of DNA fragments adjacent to known sequences in human and yeast artificial chromosome DNA. (See, e.g., Lagerstrom, M. et al. (1991) PCR Methods Applic. 1:111–119.) In this method, multiple restriction enzyme digestions and ligations may be used to insert an engineered double-stranded sequence into a region of unknown sequence before performing PCR. Other methods which may be used to retrieve unknown sequences are known in the art. (See, e.g., Parker, J. D. et al. (1991) Nucleic Acids Res. 19:3055–306). Additionally, one may use PCR, nested primers, and PromoterFinder™ libraries to walk genomic DNA (Clontech, Palo Alto, Calif.). This procedure avoids the need to screen libraries and is useful in finding intron/exon junctions. For all PCR-based methods, primers may be designed using commercially available software, such as OLIGO™ 4.06 primer analysis software (National Biosciences Inc., Plymouth, Minn.) or another appropriate program, to be about 22 to 30 nucleotides in length, to have a GC content of about 50% or more, and to anneal to the template at temperatures of about 68° C. to 72° C.

When screening for full-length cDNAs, it is preferable to use libraries that have been size-selected to include larger cDNAs. In addition, random-primed libraries, which often include sequences containing the 5' regions of genes, are preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different nucleotide-specific, laser-stimulated fluorescent dyes, and a charge coupled device camera for detection of the emitted wavelengths. Output/light intensity may be converted to electrical signal using appropriate software (e.g., Genotyper™ and Sequence Navigator™, Perkin Elmer), and the entire process from loading of samples to computer analysis and electronic data display may be computer controlled. Capillary electrophoresis is especially preferable for sequencing small DNA fragments which may be present in limited amounts in a particular sample.

In another embodiment of the invention, polynucleotide sequences or fragments thereof which encode HUTRAN may be cloned in recombinant DNA molecules that direct expression of HUTRAN, or fragments or functional equivalents thereof, in appropriate host cells. Due to the inherent degeneracy of the genetic code, other DNA sequences which encode substantially the same or a functionally equivalent amino acid sequence may be produced and used to express HUTRAN.

The nucleotide sequences of the present invention can be engineered using methods generally known in the art in order to alter HUTRAN-encoding sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth.

In another embodiment, sequences encoding HUTRAN may be synthesized, in whole or in part, using chemical methods well known in the art. (See, e.g., Caruthers, M. H. et al. (1980) Nucl. Acids Res. Symp. Ser. 215–223, and Horn, T. et al. (1980) Nucl. Acids Res. Symp. Ser. 225–232.) Alternatively, HUTRAN itself or a fragment thereof may be synthesized using chemical methods. For example, peptide synthesis can be performed using various solid-phase techniques. (See, e.g., Roberge, J. Y. et al. (1995) Science 269:202–204.) Automated synthesis may be achieved using the ABI 431A peptide synthesizer (Perkin Elmer). Additionally, the amino acid sequence of HUTRAN, or any part thereof, may be altered during direct synthesis and/or combined with sequences from other proteins, or any part thereof, to produce a variant polypeptide.

The peptide may be substantially purified by preparative high performance liquid chromatography. (See, e.g, Chiez, R. M. and F. Z. Regnier (1990) Methods Enzymol. 182:392–421.) The composition of the synthetic peptides may be confirmed by amino acid analysis or by sequencing. (See, e.g., Creighton, T. (1984) *Proteins, Structures and Molecular Properties*, WH Freeman and Co., New York, N.Y.)

In order to express a biologically active HUTRAN, the nucleotide sequences encoding HUTRAN or derivatives thereof may be inserted into an appropriate expression vector, i.e., a vector which contains the necessary elements for transcriptional and translational control of the inserted coding sequence in a suitable host. These elements include regulatory sequences, such as enhancers, constitutive and inducible promoters, and 5' and 3' untranslated regions in the vector and in polynucleotide sequences encoding HUTRAN. Such elements may vary in their strength and specificity. Specific initiation signals may also be used to achieve more efficient translation of sequences encoding HUTRAN. Such signals include the ATG initiation codon and adjacent sequences, e.g. the Kozak sequence. In cases where sequences encoding HUTRAN and its initiation codon and upstream regulatory sequences are inserted into the appropriate expression vector, no additional transcriptional or translational control signals may be needed. However, in cases where only coding sequence, or a fragment thereof, is inserted, exogenous translational control signals including an in-frame ATG initiation codon should be provided by the vector. Exogenous translational elements and initiation codons may be of various origins, both natural and synthetic. The efficiency of expression may be enhanced by the inclusion of enhancers appropriate for the particular host cell system used. (See, e.g., Scharf, D. et al. (1994) Results Probl. Cell Differ. 20:125–162.)

Methods which are well known to those skilled in the art may be used to construct expression vectors containing sequences encoding HUTRAN and appropriate transcriptional and translational control elements. These methods include in vitro recombinant DNA techniques, synthetic techniques, and in vivo genetic recombination. (See, e.g., Sambrook, J. et al. (1989) *Molecular Cloning, A Laboratory Manual*, Cold Spring Harbor Press, Plainview, N.Y., ch. 4, 8, and 16–17; and Ausubel, F. M. et al. (1995, and periodic supplements) *Current Protocols in Molecular Biology*, John Wiley & Sons, New York, N.Y., ch. 9, 13, and 16.)

A variety of expression vector/host systems may be utilized to contain and express sequences encoding HUTRAN. These include, but are not limited to, microorganisms such as bacteria transformed with recombinant bacteriophage, plasmid, or cosmid DNA expression vectors; yeast transformed with yeast expression vectors; insect cell systems infected with viral expression vectors (e.g., baculovirus); plant cell systems transformed with viral expression vectors (e.g., cauliflower mosaic virus (CaMV) or tobacco mosaic virus (TMV)) or with bacterial expression vectors (e.g., Ti or pBR322 plasmids); or animal cell systems. The invention is not limited by the host cell employed.

In bacterial systems, a number of cloning and expression vectors may be selected depending upon the use intended for polynucleotide sequences encoding HUTRAN. For example, routine cloning, subcloning, and propagation of polynucleotide sequences encoding HUTRAN can be achieved using a multifunctional *E. coli* vector such as Bluescript® (Stratagene) or pSport1™ plasmid (Life Technologies, Inc., Gaithersburg, Md.). Ligation of sequences encoding HUTRAN into the vector's multiple cloning site disrupts the lacZ gene, allowing a colorimetric screening procedure for identification of transformed bacteria containing recombinant molecules. In addition, these vectors may be useful for in vitro transcription, dideoxy sequencing, single strand rescue with helper phage, and creation of nested deletions in the cloned sequence. (See, e.g., Van Heeke, G. and S. M. Schuster (1989) J. Biol. Chem. 264:5503–5509.) When large quantities of HUTRAN are needed, e.g. for the production of antibodies, vectors which direct high level expression of HUTRAN may be used. For example, vectors containing the strong, inducible T5 or T7 bacteriophage promoter may be used.

Yeast expression systems may be used for production of HUTRAN. A number of vectors containing constitutive or inducible promoters, such as alpha factor, alcohol oxidase, and PGH, may be used in the yeast *Saccharomyces cerevisiae* or *Pichia pastoris*. In addition, such vectors direct either the secretion or intracellular retention of expressed proteins and enable integration of foreign sequences into the host genome for stable propagation. (See, e.g., Ausubel, supra; and Grant et al. (1987) Methods Enzymol. 153:516–54; Scorer, C. A. et al. (1994) Bio/Technology 12:181–184.)

Plant systems may also be used for expression of HUTRAN. Transcription of sequences encoding HUTRAN may be driven viral promoters, e.g., the 35S and 19S promoters of CaMV used alone or in combination with the omega leader sequence from TMV. (Takamatsu, N. (1987) EMBO J. 6:307–311.) Alternatively, plant promoters such as the small subunit of RUBISCO or heat shock promoters may be used. (See, e.g., Coruzzi, G. et al. (1984) EMBO J. 3:1671–1680; Broglie, R. et al. (1984) Science 224:838–843; and Winter, J. et al. (1991) Results Probl. Cell Differ. 17:85–105.) These constructs can be introduced into plant cells by direct DNA transformation or pathogen-mediated transfection. (See, e.g., Hobbs, S. or Murry, L. E. in *McGraw Hill Yearbook of Science and Technology* (1992) McGraw Hill, New York, N.Y.; pp. 191–196.)

In mammalian cells, a number of viral-based expression systems may be utilized. In cases where an adenovirus is used as an expression vector, sequences encoding HUTRAN may be ligated into an adenovirus transcription/translation complex consisting of the late promoter and tripartite leader sequence. Insertion in a non-essential E1 or E3 region of the viral genome may be used to obtain infective virus which expresses HUTRAN in host cells. (See, e.g., Logan, J. and T. Shenk (1984) Proc. Natl. Acad. Sci. 81:3655–3659.) In addition, transcription enhancers, such as the Rous sarcoma virus (RSV) enhancer, may be used to increase expression in mammalian host cells. SV40 or EBV-based vectors may also be used for high-level protein expression.

Human artificial chromosomes (HACs) may also be employed to deliver larger fragments of DNA than can be contained in and expressed from a plasmid. HACs of about 6 kb to 10 Mb are constructed and delivered via conventional delivery methods (liposomes, polycationic amino polymers, or vesicles) for therapeutic purposes.

For long term production of recombinant proteins in mammalian systems, stable expression of HUTRAN in cell lines is preferred. For example, sequences encoding HUTRAN can be transformed into cell lines using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to a selective agent, and its presence allows growth and recovery of cells which successfully express the introduced sequences. Resistant clones of stably transformed cells may be propagated using tissue culture techniques appropriate to the cell type.

Any number of selection systems may be used to recover transformed cell lines. These include, but are not limited to, the herpes simplex virus thymidine kinase and adenine phosphoribosyltransferase genes, for use in $tk^-$ or $apr^-$ cells, respectively. (See, e.g., Wigler, M. et al. (1977) Cell 11:223–232; and Lowy, I. et al. (1980) Cell 22:817–823.) Also, antimetabolite, antibiotic, or herbicide resistance can be used as the basis for selection. For example, dhfr confers resistance to methotrexate; neo confers resistance to the aminoglycosides neomycin and G-418; and als or pat confer resistance to chlorsulfuron and phosphinotricin acetyltransferase, respectively. (See, e.g., Wigler, M. et al. (1980) Proc. Natl. Acad. Sci. 77:3567–3570; Colbere-Garapin, F. et al (1981) J. Mol. Biol. 150:1–14; and Murry, supra.) Additional selectable genes have been described, e.g., trpB and hisD, which alter cellular requirements for metabolites. (See, e.g., Hartman, S. C. and R. C. Mulligan (1988) Proc. Natl. Acad. Sci. 85:8047–8051.) Visible markers, e.g., anthocyanins, green fluorescent proteins (GFP) (Clontech, Palo Alto, Calif.), β glucuronidase and its substrate β-D-glucuronoside, or luciferase and its substrate luciferin may be used. These markers can be used not only to identify transformants, but also to quantify the amount of transient or stable protein expression attributable to a specific vector system. (See, e.g., Rhodes, C. A. et al. (1995) Methods Mol. Biol. 55:121–131.)

Although the presence/absence of marker gene expression suggests that the gene of interest is also present, the presence and expression of the gene may need to be confirmed. For example, if the sequence encoding HUTRAN is inserted within a marker gene sequence, transformed cells containing sequences encoding HUTRAN can be identified by the absence of marker gene function. Alternatively, a marker gene can be placed in tandem with a sequence encoding HUTRAN under the control of a single promoter. Expression of the marker gene in response to induction or selection usually indicates expression of the tandem gene as well.

In general, host cells that contain the nucleic acid sequence encoding HUTRAN and that express HUTRAN may be identified by a variety of procedures known to those of skill in the art. These procedures include, but are not limited to, DNA-DNA or DNA-RNA hybridizations, PCR amplification, and protein bioassay or immunoassay techniques which include membrane, solution, or chip based technologies for the detection and/or quantification of nucleic acid or protein sequences.

Immunological methods for detecting and measuring the expression of HUTRAN using either specific polyclonal or monoclonal antibodies are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on HUTRAN is preferred, but a competitive binding assay may be employed. These and other assays are well known in the art. (See, e.g., Hampton, R. et al. (1990) *Serological Methods, a Laboratory Manual*, APS Press, St Paul, Minn., Section IV; Coligan, J. E. et al. (1997 and periodic supplements) *Current Protocols in Immunology,* Greene Pub. Associates and Wiley-Interscience, New York, N.Y.; and Maddox, D. E. et al. (1983) J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding HUTRAN include oligolabeling, nick translation, end-labeling, or PCR amplification using a labeled nucleotide. Alternatively, the sequences encoding HUTRAN, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Amersham Pharmacia Biotech (Piscataway, N.J.), Promega (Madison, Wis.), and U.S. Biochemical Corp. (Cleveland, Ohio). Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding HUTRAN may be cultured under conditions suitable for the expression and recovery of the protein from cell culture. The protein produced by a transformed cell may be secreted or retained intracellularly depending on the sequence and/or the vector used. As will be understood by those of skill in the art, expression vectors containing polynucleotides which encode HUTRAN may be designed to contain signal sequences which direct secretion of HUTRAN through a prokaryotic or eukaryotic cell membrane.

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to specify protein targeting, folding, and/or activity. Different host cells which have specific cellular machinery and characteristic mechanisms for post-translational activities (e.g., CHO, HeLa, MDCK, HEK293, and W138), are available from the American Type Culture Collection (ATCC, Manassas, VA.) and may be chosen to ensure the correct modification and processing of the foreign protein.

In another embodiment of the invention, natural, modified, or recombinant nucleic acid sequences encoding HUTRAN may be ligated to a heterologous sequence resulting in translation of a fusion protein in any of the aforementioned host systems. For example, a chimeric HUTRAN protein containing a heterologous moiety that can be recognized by a commercially available antibody may facilitate the screening of peptide libraries for inhibitors of HUTRAN activity. Heterologous protein and peptide moieties may also facilitate purification of fusion proteins using commercially available affinity matrices. Such moieties include, but are not limited to, glutathione S-transferase (GST), maltose binding protein (MBP), thioredoxin (Trx), calmodulin binding peptide (CBP), 6-His, FLAG, c-myc, and hemagglutinin (HA). GST, MBP, Trx, CBP, and 6-His enable purification of their cognate fusion proteins on immobilized glutathione, maltose, phenylarsine oxide, calmodulin, and metal-chelate resins, respectively. FLAG, c-myc, and hemagglutinin (HA) enable immunoaffinity purification of fusion proteins using commercially available monoclonal and polyclonal antibodies that specifically recognize these epitope tags. A fusion protein may also be engineered to contain a proteolytic cleavage site located between the HUTRAN encoding sequence and the heterologous protein sequence, so that HUTRAN may be cleaved away from the heterologous moiety following purification. Methods for fusion protein expression and purification are discussed in Ausubel, F. M. et al. (1995 and periodic supplements) *Current Protocols in Molecular Biology*, John Wiley & Sons, New York, N.Y., ch 10. A variety of commercially available kits may also be used to facilitate expression and purification of fusion proteins.

In a further embodiment of the invention, synthesis of radiolabeled HUTRAN may be achieved in vitro using the TNT™ rabbit reticulocyte lysate or wheat germ extract systems (Promega, Madison, Wis.). These systems couple transcription and translation of protein-coding sequences operably associated with the T7, T3, or SP6 promoters. Translation takes place in the presence of a radiolabeled amino acid precursor, preferably $^{35}$S-methionine.

Fragments of HUTRAN may be produced not only by recombinant production, but also by direct peptide synthesis using solid-phase techniques. (See, e.g., Creighton, supra pp. 55–60.) Protein synthesis may be performed by manual techniques or by automation. Automated synthesis may be achieved, for example, using the Applied Biosystems 431A peptide synthesizer (Perkin Elmer). Various fragments of HUTRAN may be synthesized separately and then combined to produce the full length molecule.

Therapeutics

Chemical and structural similarity, e.g., in the context of sequences and motifs, exists between HUTRAN-1 and glutamine-phenylpyruvate aminotransferase from man (GI 758591), between HUTRAN-2 and kynurenine/α-aminoadipate aminotransferase from rat (GI 1050752), and between HUTRAN-3 and arginine methyltransferase from man (GI 1808648). In addition, HUTRAN is expressed in cancerous, inflamed, male and female reproductive, nervous, and gastrointestinal tissues. Therefore, HUTRAN appears to play a role in autoimmune/inflammatory, neurological, reproductive, and gastrointestinal disorders, and cancer.

Therefore, in one embodiment, an antagonist of HUTRAN may be administered to a subject to treat or prevent an autoimmune/inflammatory disorder. Such an autoimmune/inflammatory disorder may include, but is not limited to, acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves'disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjögren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma. In one aspect, an antibody which specifically binds HUTRAN may be used directly as an antagonist or indirectly as a targeting or delivery mechanism for bringing a pharmaceutical agent to cells or tissue which express HUTRAN.

In an additional embodiment, a vector expressing the complement of the polynucleotide encoding HUTRAN may be administered to a subject to treat or prevent an autoimmune/inflammatory disorder including, but not limited to, those described above.

In another embodiment, HUTRAN or a fragment or derivative thereof may be administered to a subject to treat or prevent a neurological disorder. Such neurological disorders can include, but are not limited to, epilepsy, ischemic cerebrovascular disease, stroke, cerebral neoplasms, Alzheimer's disease, Pick's disease, Huntington's disease, dementia, Parkinson's disease and other extrapyramidal disorders, amyotrophic lateral sclerosis and other motor neuron disorders, progressive neural muscular atrophy, retinitis pigmentosa, hereditary ataxias, multiple sclerosis and other demyelinating diseases, bacterial and viral meningitis, brain abscess, subdural empyema, epidural abscess, suppurative intracranial thrombophlebitis, myelitis and radiculitis, viral central nervous system disease; prion diseases including kuru, Creutzfeldt-Jakob disease, and Gerstmann-Straussler-Scheinker syndrome; fatal familial insomnia, nutritional and metabolic diseases of the nervous system, neurofibromatosis, tuberous sclerosis, cerebelloretinal hemangioblastomatosis, encephalotrigeminal syndrome, mental retardation and other developmental disorders of the central nervous system, cerebral palsy, neuroskeletal disorders, autonomic nervous system disorders, cranial nerve disorders, spinal cord diseases, muscular dystrophy and other neuromuscular disorders, peripheral nervous system disorders, dermatomyositis and polymyositis; inherited, metabolic, endocrine, and toxic myopathies; myasthenia gravis, periodic paralysis; mental disorders including mood, anxiety, and schizophrenic disorders; akathesia, amnesia, catatonia, diabetic neuropathy, tardive dyskinesia, dystonias, paranoid psychoses, postherpetic neuralgia, and Tourette's disorder.

In another embodiment, a vector capable of expressing HUTRAN or a fragment or derivative thereof may be administered to a subject to treat or prevent a neurological disorder including, but not limited to, those described above.

In a further embodiment, a pharmaceutical composition comprising a substantially purified HUTRAN in conjunction with a suitable pharmaceutical carrier may be administered to a subject to treat or prevent a neurological disorder including, but not limited to, those provided above.

In still another embodiment, an agonist which modulates the activity of HUTRAN may be administered to a subject to treat or prevent a neurological disorder including, but not limited to, those listed above.

In another embodiment, HUTRAN or a fragment or derivative thereof may be administered to a subject to treat or prevent a reproductive disorder. Such reproductive disorders can include, but are not limited to, disorders of prolactin production; infertility, including tubal disease, ovulatory defects, and endometriosis; disruptions of the estrous cycle, disruptions of the menstrual cycle, polycystic ovary syndrome, ovarian hyperstimulation syndrome, endometrial and ovarian tumors, uterine fibroids, autoimmune disorders, ectopic pregnancies, and teratogenesis; cancer of the breast, fibrocystic breast disease, and galactorrhea; disruptions of spermatogenesis, abnormal sperm physiology, cancer of the testis, cancer of the prostate, benign prostatic hyperplasia, prostatitis, Peyronie's disease, carcinoma of the male breast, and gynecomastia.

In another embodiment, a vector capable of expressing HUTRAN or a fragment or derivative thereof may be administered to a subject to treat or prevent a reproductive disorder including, but not limited to, those described above.

In a further embodiment, a pharmaceutical composition comprising a substantially purified HUTRAN in conjunction with a suitable pharmaceutical carrier may be administered to a subject to treat or prevent a reproductive disorder including, but not limited to, those provided above.

In still another embodiment, an agonist which modulates the activity of HUTRAN may be administered to a subject to treat or prevent a reproductive disorder including, but not limited to, those listed above.

In another embodiment, HUTRAN or a fragment or derivative thereof may be administered to a subject to treat or prevent a gastrointestinal disorder. Such gastrointestinal disorders can include, but are not limited to, dysphagia, peptic esophagitis, esophageal spasm, esophageal stricture, esophageal carcinoma, dyspepsia, indigestion, gastritis, gastric carcinoma, anorexia, nausea, emesis, gastroparesis, antral or pyloric edema, abdominal angina, pyrosis, gastroenteritis, intestinal obstruction, infections of the intestinal tract, peptic ulcer, cholelithiasis, cholecystitis, cholestasis, pancreatitis, pancreatic carcinoma, biliary tract disease, hepatitis, hyperbilirubinemia, cirrhosis, passive congestion of the liver, hepatoma, infectious colitis, ulcerative colitis, ulcerative proctitis, Crohn's disease, Whipple's disease, Mallory-Weiss syndrome, colonic carcinoma, colonic obstruction, irritable bowel syndrome, short bowel syndrome, diarrhea, constipation, gastrointestinal hemorrhage, and acquired immunodeficiency syndrome (AIDS) enteropathy.

In another embodiment, a vector capable of expressing HUTRAN or a fragment or derivative thereof may be administered to a subject to treat or prevent a gastrointestinal disorder including, but not limited to, those described above.

In a further embodiment, a pharmaceutical composition comprising a substantially purified HUTRAN in conjunction with a suitable pharmaceutical carrier may be administered to a subject to treat or prevent a gastrointestinal disorder including, but not limited to, those provided above.

In still another embodiment, an agonist which modulates the activity of HUTRAN may be administered to a subject to treat or prevent a gastrointestinal disorder including, but not limited to, those listed above.

In another embodiment, an antagonist of HUTRAN may be administered to a subject to treat or prevent a cancer. Such a cancer may include, but is not limited to, adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody which specifically binds HUTRAN may be used directly as an antagonist or indirectly as a targeting or delivery mechanism for bringing a pharmaceutical agent to cells or tissue which express HUTRAN.

In an additional embodiment, a vector expressing the complement of the polynucleotide encoding HUTRAN may be administered to a subject to treat or prevent a cancer including, but not limited to, those described above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of HUTRAN may be produced using methods which are generally known in the art. In particular, purified HUTRAN may be used to produce antibodies or to screen libraries of pharmaceutical agents to identify those which specifically bind HUTRAN. Antibodies to HUTRAN may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are especially preferred for therapeutic use.

For the production of polyclonal antibodies, various hosts including goats, rabbits, rats, mice, humans, and others may be immunized by injection with HUTRAN or with any fragment or oligopeptide thereof which has immunogenic properties. Rats and mice are preferred hosts for downstream applications involving monoclonal antibody production. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable. (For review of methods for antibody production and analysis, see, e.g., Harlow, E. and Lane, D. (1988) *Antibodies: A Laboratory Manual,* Cold Spring Harbor Laboratory, Cold Spring Harbor, N.Y.).

It is preferred that the oligopeptides, peptides, or fragments used to induce antibodies to HUTRAN have an amino acid sequence consisting of at least about 5 amino acids, and, more preferably, of at least about 14 amino acids. It is also preferable that these oligopeptides, peptides, or fragments are identical to a portion of the amino acid sequence of the natural protein and contain the entire amino acid sequence of a small, naturally occurring molecule. Short stretches of HUTRAN amino acids may be fused with those of another protein, such as KLH, and antibodies to the chimeric molecule may be produced.

Monoclonal antibodies to HUTRAN may be prepared using any technique which provides for the production of antibody molecules by continuous cell lines in culture. These include, but are not limited to, the hybridoma technique, the human B-cell hybridoma technique, and the EBV-hybridoma technique. (See, e.g., Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; and Cole, S. P. et al. (1984) Mol. Cell Biol. 62:109–120.)

In addition, techniques developed for the production of "chimeric antibodies," such as the splicing of mouse antibody genes to human antibody genes to obtain a molecule with appropriate antigen specificity and biological activity, can be used. (See, e.g., Morrison, S. L. et al. (1984) Proc. Natl. Acad. Sci. 81:6851–6855; Neuberger, M. S. et al. (1984) Nature 312:604–608; and Takeda, S. et al. (1985) Nature 314:452–454.) Alternatively, techniques described for the production of single chain antibodies may be adapted, using methods known in the art, to produce HUTRAN-specific single chain antibodies. Antibodies with related specificity, but of distinct idiotypic composition, may be generated by chain shuffling from random combinatorial immunoglobulin libraries. (See, e.g., Burton D. R. (1991) Proc. Natl. Acad. Sci. 88:10134–10137.)

Antibodies may also be produced by inducing in vivo production in the lymphocyte population or by screening immunoglobulin libraries or panels of highly specific binding reagents as disclosed in the literature. (See, e.g., Orlandi, R. et al. (1989) Proc. Natl. Acad. Sci. 86: 3833–3837; and Winter, G. et al. (1991) Nature 349:293–299.)

Antibody fragments which contain specific binding sites for HUTRAN may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse, W. D. et al. (1989) Science 246:1275–1281.)

Various immunoassays may be used for screening to identify antibodies having the desired specificity and minimal cross-reactivity. Numerous protocols for competitive binding or immunoradiometric assays using either polyclonal or monoclonal antibodies with established specificities are well known in the art. Such immunoassays typically involve the measurement of complex formation between HUTRAN and its specific antibody. A two-site, monoclonal-based immunoassay utilizing monoclonal antibodies reactive to two non-interfering HUTRAN epitopes is preferred, but a competitive binding assay may also be employed. (Maddox, supra.)

Various methods such as Scatchard analysis in conjunction with radioimmunoassay techniques may be used to assess the affinity of antibodies for HUTRAN. Affinity is expressed as an association constant, $K_a$, which is defined as the molar concentration of HUTRAN-antibody complex divided by the molar concentrations of free antigen and free antibody under equilibrium conditions. The $K_a$ determined for a preparation of polyclonal antibodies, which are heterogeneous in their affinities for multiple HUTRAN epitopes, represents the average affinity, or avidity, of the antibodies for HUTRAN. The $K_a$ determined for a preparation of monoclonal antibodies, which are monospecific for a particular HUTRAN epitope, represents a true measure of affinity. High-affinity antibody preparations with $K_a$ ranging from about $10^9$ to $10^{12}$ L/mole are preferred for use in immunoassays in which the HUTRAN-antibody complex must withstand rigorous manipulations. Low-affinity antibody preparations with $K_a$ ranging from about $10^6$ to $10^7$ L/mole are preferred for use in immunopurification and similar procedures which ultimately require dissociation of HUTRAN, preferably in active form, from the antibody. (Catty, D. (1988) *Antibodies. Volume I: A Practical Approach,* IRL Press, Washington, D. C.; and Liddell, J. E. and Cryer, A. (1991) *A Practical Guide to Monoclonal Antibodies,* John Wiley & Sons, New York, N.Y.).

The titre and avidity of polyclonal antibody preparations may be further evaluated to determine the quality and suitability of such preparations for certain downstream applications. For example, a polyclonal antibody preparation containing at least 1–2 mg specific antibody/ml, preferably 5–10 mg specific antibody/ml, is preferred for use in procedures requiring precipitation of HUTRAN-antibody complexes. Procedures for evaluating antibody specificity, titer, and avidity, and guidelines for antibody quality and usage in various applications, are generally available. (See, e.g., Catty, supra, and Coligan et al. supra.)

In another embodiment of the invention, the polynucleotides encoding HUTRAN, or any fragment or complement thereof, may be used for therapeutic purposes. In one aspect, the complement of the polynucleotide encoding HUTRAN may be used in situations in which it would be desirable to block the transcription of the mRNA. In particular, cells may be transformed with sequences complementary to polynucleotides encoding HUTRAN. Thus, complementary molecules or fragments may be used to modulate HUTRAN activity, or to achieve regulation of gene function. Such technology is now well known in the art, and sense or antisense oligonucleotides or larger fragments can be designed from various locations along the coding or control regions of sequences encoding HUTRAN.

Expression vectors derived from retroviruses, adenoviruses, or herpes or vaccinia viruses, or from various bacterial plasmids, may be used for delivery of nucleotide sequences to the targeted organ, tissue, or cell population. Methods which are well known to those skilled in the art can be used to construct vectors to express nucleic acid sequences complementary to the polynucleotides encoding HUTRAN. (See, e.g., Sambrook, supra; and Ausubel, supra.)

Genes encoding HUTRAN can be turned off by transforming a cell or tissue with expression vectors which express high levels of a polynucleotide, or fragment thereof, encoding HUTRAN. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector, and may last even longer if appropriate replication elements are part of the vector system.

As mentioned above, modifications of gene expression can be obtained by designing complementary sequences or antisense molecules (DNA, RNA, or PNA) to the control, 5', or regulatory regions of the gene encoding HUTRAN. Oligonucleotides derived from the transcription initiation site, e.g., between about positions −10 and +10 from the start site, are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee, J. E. et al. (1994) in Huber, B. E. and B. I. Carr, *Molecular and Immunologic Approaches,* Futura Publishing Co., Mt. Kisco, N.Y., pp. 163–177.) A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules may specifically and efficiently catalyze endonucleolytic cleavage of sequences encoding HUTRAN.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides, corresponding to the region of the target gene containing the cleavage site, may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding HUTRAN. Such DNA sequences may be incorporated into a wide variety of vectors with suitable RNA polymerase promoters such as T7 or SP6. Alternatively, these cDNA constructs that synthesize complementary RNA, constitutively or inducibly, can be introduced into cell lines, cells, or tissues.

RNA molecules may be modified to increase intracellular stability and half-life. Possible modifications include, but are not limited to, the addition of flanking sequences at the 5' and/or 3' ends of the molecule, or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (See, e.g., Goldman, C. K. et al. (1997) Nature Biotechnology 15:462–466.)

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical or sterile composition, in conjunction with a pharmaceutically acceptable carrier, for any of the therapeutic effects discussed above. Such pharmaceutical compositions may consist of HUTRAN, antibodies to HUTRAN, and mimetics, agonists, antagonists, or inhibitors of HUTRAN. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs, or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acid. Salts tend to be more soluble in aqueous or other protonic solvents than are the corresponding free base forms. In other cases, the preferred preparation may be a lyophilized powder which may contain any or all of the following: 1 mM to 50 mM histidine, 0.1% to 2% sucrose, and 2% to 7% mannitol, at a pH range of 4.5 to 5.5, that is combined with buffer prior to use.

After pharmaceutical compositions have been prepared, they can be placed in an appropriate container and labeled for treatment of an indicated condition. For administration of HUTRAN, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells or in animal models such as mice, rats, rabbits, dogs, or pigs. An animal model may also be used to determine the appropriate concentration range and route of administration. Such information can then be used to determine useful doses and routes for administration in humans.

A therapeutically effective dose refers to that amount of active ingredient, for example HUTRAN or fragments thereof, antibodies of HUTRAN, and agonists, antagonists or inhibitors of HUTRAN, which ameliorates the symptoms or condition. Therapeutic efficacy and toxicity may be determined by standard pharmaceutical procedures in cell cultures or with experimental animals, such as by calculating the $ED_{50}$ (the dose therapeutically effective in 50% of the population) or $LD_{50}$ (the dose lethal to 50% of the population) statistics. The dose ratio of therapeutic to toxic effects is the therapeutic index, and it can be expressed as the $ED_{50}/LD_{50}$ ratio. Pharmaceutical compositions which exhibit large therapeutic indices are preferred. The data obtained from cell culture assays and animal studies are used to formulate a range of dosage for human use. The dosage contained in such compositions is preferably within a range of circulating concentrations that includes the $ED_{50}$ with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

Normal dosage amounts may vary from about 0.1 $\mu$g to 100,000 $\mu$g, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind HUTRAN may be used for the diagnosis of disorders characterized by expression of HUTRAN, or in assays to monitor patients being treated with HUTRAN or agonists, antagonists, or inhibitors of HUTRAN. Antibodies useful for diagnostic purposes may be prepared in the same manner as described above for therapeutics. Diagnostic assays for HUTRAN include methods which utilize the antibody and a label to detect HUTRAN in human body fluids or in extracts of cells or tissues. The antibodies may be used with or without modification, and may be labeled by covalent or non-covalent attachment of a reporter molecule. A wide variety of reporter molecules, several of which are described above, are known in the art and may be used.

A variety of protocols for measuring HUTRAN, including ELISAs, RIAs, and FACS, are known in the art and provide a basis for diagnosing altered or abnormal levels of HUTRAN expression. Normal or standard values for HUTRAN expression are established by combining body fluids or cell extracts taken from normal mammalian subjects, preferably human, with antibody to HUTRAN under conditions suitable for complex formation. The amount of standard complex formation may be quantitated by various methods, preferably by photometric means. Quantities of HUTRAN expressed in subject samples from biopsied tissues are compared with the standard values. Deviation between standard and subject values establishes the parameters for diagnosing disease.

In another embodiment of the invention, the polynucleotides encoding HUTRAN may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of HUTRAN may be correlated with disease. The diagnostic assay may be used to determine absence, presence, and excess expression of HUTRAN, and to monitor regulation of HUTRAN levels during therapeutic intervention.

In one aspect, hybridization with PCR probes which are capable of detecting polynucleotide sequences, including genomic sequences, encoding HUTRAN or closely related molecules may be used to identify nucleic acid sequences which encode HUTRAN. The specificity of the probe, whether it is made from a highly specific region, e.g., the 5' regulatory region, or from a less specific region, e.g., a conserved motif, and the stringency of the hybridization or amplification (maximal, high, intermediate, or low), will determine whether the probe identifies only naturally occurring sequences encoding HUTRAN, allelic variants, or related sequences.

Probes may also be used for the detection of related sequences, and should preferably have at least 50% sequence identity to any of the HUTRAN encoding sequences. The hybridization probes of the subject invention may be DNA or RNA and may be derived from the sequence of the sequences of SEQ ID NO:4, SEQ ID NO:5, or SEQ ID NO:6 or from genomic sequences including promoters, enhancers, and introns of the HUTRAN gene.

Means for producing specific hybridization probes for DNAs encoding HUTRAN include the cloning of polynucleotide sequences encoding HUTRAN or HUTRAN derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}P$ or $^{35}S$, or by enzymatic labels, such as alkaline phosphatase coupled to the probe via avidin/biotin coupling systems, and the like.

Polynucleotide sequences encoding HUTRAN may be used for the diagnosis of a disorder associated with expression of HUTRAN. Examples of such a disorder include, but are not limited to, autoimmune/inflammatory disorders such as acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves'disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjögren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma; neurological disorders such as epilepsy, ischemic cerebrovascular disease, stroke, cerebral neoplasms, Alzheimer's disease, Pick's disease, Huntington's disease, dementia, Parkinson's disease and other extrapyramidal disorders, amyotrophic lateral sclerosis and other motor neuron disorders, progressive neural muscular atrophy, retinitis pigmentosa, hereditary ataxias, multiple sclerosis and other demyelinating diseases, bacterial and viral meningitis, brain abscess, subdural empyema, epidural abscess, suppurative intracranial thrombophlebitis, myelitis and radiculitis, viral central nervous system disease; prion diseases including kuru, Creutzfeldt-Jakob disease, and Gerstmann-Straussler-Scheinker syndrome; fatal familial insomnia, nutritional and metabolic diseases of the nervous system, neurofibromatosis, tuberous sclerosis, cerebelloretinal hemangioblastomatosis, encephalotrigeminal syndrome, mental retardation and other developmental disorders of the central nervous system, cerebral palsy, neuroskeletal disorders, autonomic nervous system disorders, cranial nerve disorders, spinal cord diseases, muscular dystrophy and other neuromuscular disorders, peripheral nervous system disorders, dermatomyositis and polymyositis; inherited, metabolic, endocrine, and toxic myopathies; myasthenia gravis, periodic paralysis; mental disorders including mood, anxiety, and schizophrenic disorders; akathesia, amnesia, catatonia, diabetic neuropathy, tardive dyskinesia, dystonias, paranoid psychoses, postherpetic neuralgia, and Tourette's disorder; reproductive disorders such as disorders of prolactin production; infertility, including tubal disease, ovulatory defects, and endometriosis; disruptions of the estrous cycle, disruptions of the menstrual cycle, polycystic ovary syndrome, ovarian hyperstimulation syndrome, endometrial and ovarian tumors, uterine fibroids, autoimmune disorders, ectopic pregnancies, and teratogenesis; cancer of the breast, fibrocystic breast disease, and galactorrhea; disruptions of spermatogenesis, abnormal sperm physiology, cancer of the testis, cancer of the prostate, benign prostatic hyperplasia, prostatitis, Peyronie's disease, carcinoma of the male breast, and gynecomastia; gastrointestinal disorders such as; dysphagia, peptic esophagitis, esophageal spasm, esophageal stricture, esophageal carcinoma, dyspepsia, indigestion, gastritis, gastric carcinoma, anorexia, nausea, emesis, gastroparesis, antral or pyloric edema, abdominal angina, pyrosis, gastroenteritis, intestinal obstruction, infections of the intestinal tract, peptic ulcer, cholelithiasis, cholecystitis, cholestasis, pancreatitis, pancreatic carcinoma, biliary tract disease, hepatitis, hyperbilirubinemia, cirrhosis, passive congestion of the liver, hepatoma, infectious colitis, ulcerative colitis, ulcerative proctitis, Crohn's disease, Whipple's disease, Mallory-Weiss syndrome, colonic carcinoma, colonic obstruction, irritable bowel syndrome, short bowel syndrome, diarrhea, constipation, gastrointestinal hemorrhage, and acquired immunodeficiency syndrome (AIDS) enteropathy; and cancers such as adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. The polynucleotide sequences encoding HUTRAN may be used in Southern or Northern analysis, dot blot, or other membrane-based technologies; in PCR technologies; in dipstick, pin, and ELISA assays; and in microarrays utilizing fluids or tissues from patients to detect altered HUTRAN expression. Such qualitative or quantitative methods are well known in the art.

In a particular aspect, the nucleotide sequences encoding HUTRAN may be useful in assays that detect the presence of associated disorders, particularly those mentioned above. The nucleotide sequences encoding HUTRAN may be labeled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly altered in comparison to a control sample then the presence of altered levels of nucleotide sequences encoding HUTRAN in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis of a disorder associated with expression of HUTRAN, a normal or standard profile for expression is established. This may be accomplished by combining body fluids or cell extracts taken from normal subjects, either animal or human, with a sequence, or a fragment thereof, encoding HUTRAN, under conditions suitable for hybridization or amplification. Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to determine if the level of expression in the patient begins to approximate that which is observed in the normal subject. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding HUTRAN may involve the use of PCR. These oligomers may be chemically synthesized, generated enzymatically, or produced in vitro. Oligomers will preferably contain a fragment of a polynucleotide encoding HUTRAN, or a fragment of a polynucleotide complementary to the polynucleotide encoding HUTRAN, and will be employed under optimized conditions for identification of a specific gene or condition. Oligomers may also be employed under less stringent conditions for detection or quantitation of closely related DNA or RNA sequences.

Methods which may also be used to quantitate the expression of HUTRAN include radiolabeling or biotinylating nucleotides, coamplification of a control nucleic acid, and interpolating results from standard curves. (See, e.g., Melby, P. C. et al. (1993) J. Immunol. Methods 159:235–244; and Duplaa, C. et al. (1993) Anal. Biochem. 229–236.) The speed of quantitation of multiple samples may be accelerated by running the assay in an ELISA format where the oligomer of interest is presented in various dilutions and a spectrophotometric or colorimetric response gives rapid quantitation.

In further embodiments, oligonucleotides or longer fragments derived from any of the polynucleotide sequences described herein may be used as targets in a microarray. The microarray can be used to monitor the expression level of large numbers of genes simultaneously and to identify genetic variants, mutations, and polymorphisms. This information may be used to determine gene function, to understand the genetic basis of a disorder, to diagnose a disorder, and to develop and monitor the activities of therapeutic agents.

Microarrays may be prepared, used, and analyzed using methods known in the art. (See, e.g., Brennan, T. M. et al. (1995) U.S. Pat. No. 5,474,796; Schena, M. et al. (1996) Proc. Natl. Acad. Sci. 93:10614–10619; Baldeschweiler et al. (1995) PCT application WO95/251116; Shalon, D. et al. (1995) PCT application WO95/35505; Heller, R. A. et al. (1997) Proc. Natl. Acad. Sci. 94:2150–2155; and Heller, M. J. et al. (1997) U.S. Pat. No. 5,605,662.)

In another embodiment of the invention, nucleic acid sequences encoding HUTRAN may be used to generate hybridization probes useful in mapping the naturally occurring genomic sequence. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial P1 constructions, or single chromosome cDNA libraries. (See, e.g., Price, C. M. (1993) Blood Rev. 7:127–134; and Trask, B. J. (1991) Trends Genet. 7:149–154.)

Fluorescent in situ hybridization (FISH) may be correlated with other physical chromosome mapping techniques and genetic map data. (See, e.g., Heinz-Ulrich, et al. (1995) in Meyers, R. A. (ed.) *Molecular Biology and Biotechnology,* VCH Publishers New York, N.Y., pp. 965–968.) Examples of genetic map data can be found in various scientific journals or at the Online Mendelian Inheritance in Man (OMIM) site. Correlation between the location of the gene encoding HUTRAN on a physical chromosomal map and a specific disorder, or a predisposition to a specific disorder, may help define the region of DNA associated with that disorder. The nucleotide sequences of the invention may be used to detect differences in gene sequences among normal, carrier, and affected individuals.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the number or arm of a particular human chromosome is not known. New sequences can be assigned to chromosomal arms by physical mapping. This provides valuable information to investigators searching for disease genes using positional cloning or other gene discovery techniques. Once the disease or syndrome has been crudely localized by genetic linkage to a particular genomic region, e.g., ataxia-telangiectasia to 11q22-23, any sequences mapping to that area may represent associated or regulatory genes for further investigation. (See, e.g., Gatti, R. A. et al. (1988) Nature 336:577–580.) The nucleotide sequence of the subject invention may also be used to detect differences in the chromosomal location due to translocation, inversion, etc., among normal, carrier, or affected individuals.

In another embodiment of the invention, HUTRAN, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between HUTRAN and the agent being tested may be measured.

Another technique for drug screening provides for high throughput screening of compounds having suitable binding affinity to the protein of interest. (See, e.g., Geysen, et al. (1984) PCT application WO084/03564.) In this method, large numbers of different small test compounds are synthesized on a solid substrate, such as plastic pins or some other surface. The test compounds are reacted with HUTRAN, or fragments thereof, and washed. Bound HUTRAN is then detected by methods well known in the art. Purified HUTRAN can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding HUTRAN specifically compete with a test compound for binding HUTRAN. In this manner, antibodies can be used to detect the presence of any peptide which shares one or more antigenic determinants with HUTRAN.

In additional embodiments, the nucleotide sequences which encode HUTRAN may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I. Construction of cDNA Libraries

RNA was isolated from tissues described in Table 4. Some tissues were homogenized and lysed in guanidinium isothiocyanate, while others were homogenized and lysed in phenol or in a suitable mixture of denaturants, such as TRIZOL™ (Life Technologies, Inc., Gaithersburg, Md.), a monophasic solution of phenol and guanidine isothiocyanate. The resulting lysates were centrifuged over CsCl cushions or extracted with chloroform. RNA was precipitated from the lysates with either isopropanol or sodium acetate and ethanol, or by other routine methods.

Phenol extraction and precipitation of RNA were repeated as necessary to increase RNA purity. In some cases, RNA was treated with DNase. For most libraries, poly(A+) RNA was isolated using oligo d(T)-coupled paramagnetic particles (Promega Corp., Madison, Wis.), OLIGOTEX™ latex particles (QIAGEN Inc., Valencia, Calif.), or an OLIGOTEX™ mRNA purification kit (QIAGEN Inc., Valencia, Calif.). Alternatively, RNA was isolated directly from tissue lysates using other RNA isolation kits, e.g., the POLY(A) PURE™ mRNA purification kit (Ambion, Austin, Tex.).

cDNA was synthesized and cDNA libraries were constructed with the SUPERSCRIPT™ plasmid system (Life Technologies, Inc., Gaithersburg, Md.), using the recommended procedures or similar methods known in the art. (See, e.g., Ausubel, supra, 1997, units 5.1–6.6) Reverse transcription was initiated using oligo d(T) or random primers. Synthetic oligonucleotide adapters were ligated to double stranded cDNA, and the cDNA was digested with the appropriate restriction enzyme or enzymes. For most libraries, the cDNA was size-selected (300–1000 bp) using SEPHACRYL® S1000, SEPHAROSE® CL2B, or SEPHAROSE® CL4B column chromatography (Amersham Pharmacia Biotech, Piscataway, N.J.) or preparative agarose gel electrophoresis. cDNAs were ligated into compatible restriction enzyme sites of the polylinker of pINCY (Incyte Pharmaceuticals, Inc., Palo Alto, Calif.). Recombinant plasmids were transformed into competent *E. coli* cells, e.g., the XL1-Blue, XL1-BlueMRF, or SOLR™ strains (Stratagene, Inc., La Jolla, Calif.), or DH5α™, DH10B, or ElectroMAX DH10B (Life Technologies, Inc., Gaithersburg, Md.).

II. Isolation of cDNA Clones

Plasmids were recovered from host cells by cell lysis. Plasmids were purified using at least one of the following: a Magic or WIZARD® Minipreps DNA purification system (Promega Corp., Madison, Wis.); an AGTC® Miniprep purification kit (Edge Biosystems, Gaithersburg, Md.); the QIAWELL® 8 Plasmid, QIAWELL® 8 Plus Plasmid, or the QIAWELL® 8 Ultra Plasmid purification systems (QIAGEN Inc., Valencia, Calif.); or the R.E.A.L.™ Prep 96 plasmid kit (QIAGEN Inc., Valencia, Calif.). Following precipitation, plasmids were resuspended in 0.1 ml of distilled water and stored, with or without lyophilization, at 4° C.

Alternatively, plasmid DNA was amplified from host cell lysates using direct link PCR in a high-throughput format. (Rao, V. B. (1994) Anal. Biochem. 216:1–14.) Host cell lysis and thermal cycling steps were carried out in a single reaction mixture. Samples were processed and stored in 384-well plates, and the concentration of amplified plasmid DNA was quantified fluorometrically using PICOGREEN® dye (Molecular Probes, Inc., Eugene, Oreg.) and a Fluoroskan II fluorescence scanner (Labsystems Oy, Helsinki, Finland).

III. Sequencing and Analysis

The cDNAs were prepared for sequencing using either an ABI CATALYST 800 (Perkin Elmer) or a MICROLAB 2200 (Hamilton, Reno, Nev.) in combination with Peltier thermal cyclers (PTC200; MJ Research, Watertown Mass.). The cDNAs were sequenced on the ABI 373 or 377 DNA sequencing systems (Perkin Elmer) by the method of Sanger F. and A. R. Coulson (1975; J. Mol. Biol. 94:441–448) using standard ABI protocols, base calling software, and kits. Alternatively, cDNAs were sequenced using solutions and dyes from Amersham Pharmacia Biotech. Reading frame was determined using standard methods (Ausubel, supra).

The cDNA sequences presented in Table 1 and the full length nucleotide and amino acid sequences disclosed in the Sequence Listing were queried against databases such as GenBank primate (pri), rodent (rod), mammalian (mamp), vertebrate (vrtp), and eukaryote (eukp) databases, SwissProt, BLOCKS, and other databases which contain previously identified and annotated motifs and sequences. Algorithms such as Smith Waterman which deal with primary sequence patterns and secondary structure gap penalties (Smith, T. et al. (1992) Protein Engineering 5:35–51) and programs and algorithms such as BLAST (Basic Local Alignment Search Tool; Altschul, S. F. (1993) J. Mol. Evol 36:290–300; and Altschul et al. (1990) J. Mol. Biol. 215:403–410), and HMM (Hidden Markov Models; Eddy, S. R. (1996) Cur. Opin. Str. Biol. 6:361–365 and Sonnhammer, E. L. L. et al. (1997) Proteins 28:405–420) were used to assemble and analyze nucleotide and amino acid sequences. The databases, programs, algorithms, methods and tools are available, well known in the art, and described in Ausubel (supra, unit 7.7), in Meyers, R. A. (1995; *Molecular Biology and Biotechnology*, Wiley VCH, Inc, New York N.Y., p 856–853), in documentation provided with software (Genetics Computer Group (GCG), Madison Wis.), and on the world wide web (www). Two comprehensive websites which list, describe, and/or link many of the databases and tools are: 1) the www resource in practical sequence analysis (http://genome.wustl.edu/), and 2) the bibliography of computational gene recognition (http://linkage.rockefeller.edu/wli/gene/ programs.html). For example, the first website links PFAM as a database (http:// genome.wustl.edu/Pfam/) and as an HMM search tool (http://genome.wustl.edu/eddy/cgi-bin/hmm$_{13}$ page.cgi).

Table 5 summarizes the databases and tools used herein.

IV. Northern Analysis

Northern analysis is a laboratory technique used to detect the presence of a transcript of a gene and involves the hybridization of a labeled nucleotide sequence to a membrane on which RNAs from a particular cell type or tissue have been bound. (See, e.g., Sambrook, supra, ch. 7; and Ausubel, supra, ch. 4 and 16.)

Analogous computer techniques applying BLAST are used to search for identical or related molecules in nucleotide databases such as GenBank or LIFESEQ™ database (Incyte Pharmaceuticals). This analysis is much faster than multiple membrane-based hybridizations. In addition, the sensitivity of the computer search can be modified to determine whether any particular match is categorized as exact or similar.

The basis of the search is the product score, which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1% to 2% error, and, with a product score of 70, the match will be exact. Similar molecules are usually identified by selecting those which show product scores between 15 and 40, although lower scores may identify related molecules.

The results of Northern analysis are reported as a list of libraries in which the transcript encoding HUTRAN occurs. Abundance and percent abundance are also reported. Abundance directly reflects the number of times a particular transcript is represented in a cDNA library, and percent abundance is abundance divided by the total number of sequences examined in the cDNA library.

V. Extension of HUTRAN Encoding Polynucleotides

The nucleic acid sequences of Incyte Clones 1815528, 2150892, and 2525071 were used to design oligonucleotide primers for extending partial nucleotide sequences to full length. For each nucleic acid sequence, one primer was synthesized to initiate extension of an antisense polynucleotide, and the other was synthesized to initiate extension of a sense polynucleotide. Primers were used to facilitate the extension of the known sequence "outward" generating amplicons containing new unknown nucleotide sequence for the region of interest. The initial primers were designed from the cDNA using OLIGO™ 4.06 software (National Biosciences, Plymouth, Minn.), or another appropriate program, to be about 22 to 30 nucleotides in length, to have a GC content of about 50% or more, and to anneal to the target sequence at temperatures of about 68° C. to about 72° C.. Any stretch of nucleotides which would result in hairpin structures and primer-primer dimerizations was avoided.

Selected human cDNA libraries (Life Technologies, Inc., Gaithersburg, Md.) were used to extend the sequence. If more than one extension is necessary or desired, additional sets of primers are designed to further extend the known region.

High fidelity amplification was obtained by following the instructions for the XL-PCR™ kit (Perkin Elmer) and thoroughly mixing the enzyme and reaction mix. PCR was performed using the Peltier Thermal Cycler (PTC200; M. J. Research, Watertown, Mass.), beginning with 40 pmol of each primer and the recommended concentrations of all other components of the kit, with the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat steps 4 through 6 for an additional 15 cycles |
| Step 8 | 94° C. for 15 sec |
| Step 9 | 65° C. for 1 min |
| Step 10 | 68° C. for 7:15 min |
| Step 11 | Repeat steps 8 through 10 for an additional 12 cycles |
| Step 12 | 72° C. for 8 min |
| Step 13 | 4° C. (and holding) |

A 5 μl to 10 μl aliquot of the reaction mixture was analyzed by electrophoresis on a low concentration (about 0.6% to 0.8%) agarose mini-gel to determine which reactions were successful in extending the sequence. Bands thought to contain the largest products were excised from the gel, purified using QIAQUICK™ (QIAGEN Inc.), and trimmed of overhangs using Klenow enzyme to facilitate religation and cloning.

After ethanol precipitation, the products were redissolved in 13 μl of ligation buffer, 1 μl T4-DNA ligase (15 units) and 1 μl T4 polynucleotide kinase were added, and the mixture was incubated at room temperature for 2 to 3 hours, or overnight at 16° C. Competent E. coli cells (in 40 μl of appropriate media) were transformed with 3 μl of ligation mixture and cultured in 80 μl of SOC medium. (See, e.g., Sambrook, supra, Appendix A, p. 2.) After incubation for one hour at 37° C., the E. coli mixture was plated on Luria Bertani (LB) agar (See, e.g., Sambrook, supra, Appendix A, p. 1) containing carbenicillin (2×carb). The following day, several colonies were randomly picked from each plate and cultured in 150 μl of liquid LB/2× carb medium placed in an individual well of an appropriate commercially-available sterile 96-well microtiter plate. The following day, 5 μl of each overnight culture was transferred into a non-sterile 96-well plate and, after dilution 1:10 with water, 5 μl from each sample was transferred into a PCR array.

For PCR amplification, 18 μl of concentrated PCR reaction mix (3.3×) containing 4 units of rTth DNA polymerase, a vector primer, and one or both of the gene specific primers used for the extension reaction were added to each well. Amplification was performed using the following conditions:

| | |
|---|---|
| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2 through 4 for an additional 29 cycles |
| Step 6 | 72° C. for 180 sec |
| Step 7 | 4° C. (and holding) |

Aliquots of the PCR reactions were run on agarose gels together with molecular weight markers.

The sizes of the PCR products were compared to the original partial cDNAs, and appropriate clones were selected, ligated into plasmid, and sequenced.

In like manner, the nucleotide sequences of SEQ ID NO:4–6 are used to obtain 5' regulatory sequences using the procedure above, oligonucleotides designed for 5' extension, and an appropriate genomic library.

VI. Labeling and Use of Individual Hybridization Probes

Hybridization probes derived from SEQ ID NO:4–6 are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO™ 4.06 software (National Biosciences) and labeled by combining 50 pmol of each oligomer, 250 µCi of [$\gamma$-$^{32}$P] adenosine triphosphate (Amersham, Chicago, Ill.), and T4 polynucleotide kinase (DuPont NEN®, Boston, Mass.). The labeled oligonucleotides are substantially purified using a Sephadex™ G-25 superfine size exclusion dextran bead column (Pharmacia & Upjohn, Kalamazoo, Mich.). An aliquot containing $10^7$ counts per minute of the labeled probe is used in a typical membrane-based hybridization analysis of human genomic DNA digested with one of the following endonucleases: Ase I, Bgl II, Eco RI, Pst I, Xbal, or Pvu II (DuPont NEN, Boston, Mass.).

The DNA from each digest is fractionated on a 0.7% agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT AR™ film (Kodak, Rochester, N.Y.) is exposed to the blots, hybridization patterns are compared visually.

VII. Microarrays

A chemical coupling procedure and an ink jet device can be used to synthesize array elements on the surface of a substrate. (See, e.g., Baldeschweiler, supra.) An array analogous to a dot or slot blot may also be used to arrange and link elements to the surface of a substrate using thermal, UV, chemical, or mechanical bonding procedures. A typical array may be produced by hand or using available methods and machines and contain any appropriate number of elements. After hybridization, nonhybridized probes are removed and a scanner used to determine the levels and patterns of fluorescence. The degree of complementarity and the relative abundance of each probe which hybridizes to an element on the microarray may be assessed through analysis of the scanned images.

Full-length cDNAs, Expressed Sequence Tags (ESTs), or fragments thereof may comprise the elements of the microarray. Fragments suitable for hybridization can be selected using software well known in the art such as LASERGENE™. Full-length cDNAs, ESTs, or fragments thereof corresponding to one of the nucleotide sequences of the present invention, or selected at random from a cDNA library relevant to the present invention, are arranged on an appropriate substrate, e.g., a glass slide. The cDNA is fixed to the slide using, e.g., UV cross-linking followed by thermal and chemical treatments and subsequent drying. (See, e.g., Schena, M. et al. (1995) Science 270:467–470; and Shalon, D. et al. (1996) Genome Res. 6:639–645.) Fluorescent probes are prepared and used for hybridization to the elements on the substrate. The substrate is analyzed by procedures described above.

VIII. Complementary Polynucleotides

Sequences complementary to the HUTRAN-encoding sequences, or any parts thereof, are used to detect, decrease, or inhibit expression of naturally occurring HUTRAN. Although use of oligonucleotides comprising from about 15 to 30 base pairs is described, essentially the same procedure is used with smaller or with larger sequence fragments. Appropriate oligonucleotides are designed using OLIGO™ 4.06 software and the coding sequence of HUTRAN. To inhibit transcription, a complementary oligonucleotide is designed from the most unique 5' sequence and used to prevent promoter binding to the coding sequence. To inhibit translation, a complementary oligonucleotide is designed to prevent ribosomal binding to the HUTRAN-encoding transcript.

IX. Expression of HUTRAN

Expression and purification of HUTRAN is achieved using bacterial or virus-based expression systems. For expression of HUTRAN in bacteria, cDNA is subcloned into an appropriate vector containing an antibiotic resistance gene and an inducible promoter that directs high levels of cDNA transcription. Examples of such promoters include, but are not limited to, the trp-lac (tac) hybrid promoter and the T5 or T7 bacteriophage promoter in conjunction with the lac operator regulatory element. Recombinant vectors are transformed into suitable bacterial hosts, e.g., BL21 (DE3). Antibiotic resistant bacteria express HUTRAN upon induction with isopropyl beta-D-thiogalactopyranoside (IPTG). Expression of HUTRAN in eukaryotic cells is achieved by infecting insect or mammalian cell lines with recombinant *Autographica californica* nuclear polyhedrosis virus (AcMNPV), commonly known as baculovirus. The nonessential polyhedrin gene of baculovirus is replaced with cDNA encoding HUTRAN by either homologous recombination or bacterial-mediated transposition involving transfer plasmid intermediates. Viral infectivity is maintained and the strong polyhedrin promoter drives high levels of cDNA transcription. Recombinant baculovirus is used to infect *Spodoptera frugiperda* (Sf9) insect cells in most cases, or human hepatocytes, in some cases. Infection of the latter requires additional genetic modifications to baculovirus. (See Engelhard, E. K. et al. (1994) Proc. Natl. Acad. Sci. U.S.A. 91:3224–3227; Sandig, V. et al. (1996) Hum. Gene Ther. 7:1937–1945.)

In most expression systems, HUTRAN is synthesized as a fusion protein with, e.g., glutathione S-transferase (GST) or a peptide epitope tag, such as FLAG or 6-His, permitting rapid, single-step, affinity-based purification of recombinant fusion protein from crude cell lysates. GST, a 26-kilodalton enzyme from *Schistosoma japonicum*, enables the purification of fusion proteins on immobilized glutathione under conditions that maintain protein activity and antigenicity (Pharmacia, Piscataway, N.J.). Following purification, the GST moiety can be proteolytically cleaved from HUTRAN at specifically engineered sites. FLAG, an 8-amino acid peptide, enables immunoaffinity purification using commercially available monoclonal and polyclonal anti-FLAG antibodies (Eastman Kodak, Rochester, N.Y.). 6-His, a stretch of six consecutive histidine residues, enables purification on metal-chelate resins (QIAGEN Inc, Chatsworth, Calif.). Methods for protein expression and purification are discussed in Ausubel, F. M. et al. (1995 and periodic supplements) *Current Protocols in Molecular Biology*, John Wiley & Sons, New York, N.Y., ch 10, 16. Purified HUTRAN obtained by these methods can be used directly in the following activity assay.

X. Demonstration of HUTRAN Activity

HUTRAN-1

HUTRAN-1 activity may be demonstrated by the ability to convert L-phenylalanine and $\alpha$-keto-$\gamma$-methiolbutyrate to phenylpyruvate and L-methionine. (Cooper, A. J. L. and Meister, A. (1985) Meth. Enzymol. 113:344–349.) The amount of phenylpyruvate formed is measured. The reaction mixture contains 200 mM ammediol-HCl buffer (pH 9.0), 10 mM L-phenylalanine, 5 mM $\alpha$-keto-$\gamma$-methiolbutyrate, and HUTRAN-1 in a final volume of 0.1 ml. After incubating at 37° C. for 10 minutes, 0.9 ml of 3.33 M NaOh is added. The absorbance at 322 nm, measured using a spectrophotometer, is proportional to the phentlpyruvate formed, and thus to the HUTRAN-1 in the starting sample. The absorbance due to phenylpyruvate is stable for at least 15 minutes.

HUTRAN-2

HUTRAN-2 activity may be demonstrated by the ability to convert L-glutamate and α-ketoadipate to α-aminoadipate and α-ketoglutarate. (Nakatani, supra.) The amount of α-ketoglutarate formed is measured. The standard assay contains, in a volume of 0.3 ml, 50 μmoles potassium phosphate buffer (pH 7.5), 20 μg pyridoxal phosphate, 0.5 μmoles α-ketoadipate, and HUTRAN-2. After a 5 minute incubation at 37° C., the reaction is started by addition of 0.2 ml of 0.1 M potassium L-glutamate and allowed to proceed for 10 minutes at 37° C. The reaction (Reaction 1) is terminated by adding 0.1 ml of 1 M HCl. After neutralization of the mixture with 0.1 ml of 1 M KOH, a 0.3 ml aliquot is taken for the determination of the presence of α-ketoglutarate. α-Ketoglutarate is estimated by the amount of NADH oxidized in the presence of $NH_4^+$ and glutamate dehydrogenase. The estimation of α-ketoglutarate is performed in a system consisting of 300 μmoles potassium phosphate buffer (pH 7.5), 150 μmoles $NH_4Cl$, 0.3 μmole NADH, and the neutralized reaction mixture in a total volume of 3.0 ml. The decrease in absorbance at 340 nm after the addition of glutamate dehydrogenase, measured using a spectrophotometer, is proportional to the α-ketoglutarate formed in Reaction 1, and thus to the HUTRAN-2 in the starting sample.

HUTRAN-3

HUTRAN-3 activity may be demonstrated by the ability to methylate hnRNP A1 protein in vitro. (Lin, supra). The reaction contains 490 ng bacterially expressed recombinant human hnRNP A1, 0.93 μM [$^3$H]S-adenosyl-L-methionine (2.2 μCi), 2.0 μg HUTRAN-3, and buffer (25 mM Tris-HCl, 1 mM EDTA, and 1 mM EGTA at pH 7.5) in a final volume of 30 μl. The reaction mixtures are incubated at 30° C. for 30 minutes and then subjected to SDS-polyacrylamide gel electrophoresis. The gel is stained with Coomassie Blue, dried and subjected to fluorography. The position of hnRNP A1 is determined by Coomassie Blue staining. The amount of [$^3$H]methylated hnRNP A1, as determined by densitometry or PhosphorImager analysis (Molecular Dynamics, Sunnyvale, Calif.), is proportional to the amount of HUTRAN-3 in the starting sample.

XI. Functional Assays

HUTRAN function is assessed by expressing the sequences encoding HUTRAN at physiologically elevated levels in mammalian cell culture systems. cDNA is subcloned into a mammalian expression vector containing a strong promoter that drives high levels of cDNA expression. Vectors of choice include pCMV SPOT™ (Life Technologies, Gaithersburg, Md.) and pCR™ 3.1 (Invitrogen, Carlsbad, Calif., both of which contain the cytomegalovirus promoter. 5–10 μg of recombinant vector are transiently transfected into a human cell line, preferably of endothelial or hematopoietic origin, using either liposome formulations or electroporation. 1–2 μg of an additional plasmid containing sequences encoding a marker protein are co-transfected. Expression of a marker protein provides a means to distinguish transfected cells from nontransfected cells and is a reliable predictor of cDNA expression from the recombinant vector. Marker proteins of choice include, e.g., Green Fluorescent Protein (GFP) (Clontech, Palo Alto, Calif.), CD64, or a CD64-GFP fusion protein. Flow cytometry (FCM), an automated, laser optics-based technique, is used to identify transfected cells expressing GFP or CD64-GFP, and to evaluate properties, for example, their apoptotic state. FCM detects and quantifies the uptake of fluorescent molecules that diagnose events preceding or coincident with cell death. These events include changes in nuclear DNA content as measured by staining of DNA with propidium iodide; changes in cell size and granularity as measured by forward light scatter and 90 degree side light scatter; down-regulation of DNA synthesis as measured by decrease in bromodeoxyuridine uptake; alterations in expression of cell surface and intracellular proteins as measured by reactivity with specific antibodies; and alterations in plasma membrane composition as measured by the binding of fluorescein-conjugated Annexin V protein to the cell surface. Methods in flow cytometry are discussed in Ormerod, M. G. (1994) *Flow Cytometry*, Oxford, New York, N.Y.

The influence of HUTRAN on gene expression can be assessed using highly purified populations of cells transfected with sequences encoding HUTRAN and either CD64 or CD64-GFP. CD64 and CD64-GFP are expressed on the surface of transfected cells and bind to conserved regions of human immunoglobulin G (IgG). Transfected cells are efficiently separated from nontransfected cells using magnetic beads coated with either human IgG or antibody against CD64 (DYNAL, Lake Success, N.Y.). mRNA can be purified from the cells using methods well known by those of skill in the art. Expression of mRNA encoding HUTRAN and other genes of interest can be analyzed by Northern analysis or microarray techniques.

XII. Production of HUTRAN Specific Antibodies

HUTRAN substantially purified using polyacrylamide gel electrophoresis (PAGE)(see, e.g., Harrington, M. G. (1990) Methods Enzymol. 182:488–495), or other purification techniques, is used to immunize rabbits and to produce antibodies using standard protocols.

Alternatively, the HUTRAN amino acid sequence is analyzed using LASERGENE™ software (DNASTAR Inc.) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art. (See, e.g., Ausubel supra, ch. 11.)

Typically, oligopeptides 15 residues in length are synthesized using an Applied Biosystems Peptide Synthesizer Model 431A using fmoc-chemistry and coupled to KLH (Sigma, St. Louis, Mo.) by reaction with N-maleimidobenzoyl-N-hydroxysuccinimide ester (MBS) to increase immunogenicity. (See, e.g., Ausubel supra.) Rabbits are immunized with the oligopeptide-KLH complex in complete Freund's adjuvant. Resulting antisera are tested for antipeptide activity by, for example, binding the peptide to plastic, blocking with 1% BSA, reacting with rabbit antisera, washing, and reacting with radio-iodinated goat anti-rabbit IgG.

XIII. Purification of Naturally Occurring HUTRAN Using Specific Antibodies

Naturally occurring or recombinant HUTRAN is substantially purified by immunoaffinity chromatography using antibodies specific for HUTRAN. An immunoaffinity column is constructed by covalently coupling anti-HUTRAN antibody to an activated chromatographic resin, such as CNBr-activated Sepharose (Pharmacia & Upjohn). After the coupling, the resin is blocked and washed according to the manufacturer's instructions.

Media containing HUTRAN are passed over the immunoaffinity column, and the column is washed under conditions that allow the preferential absorbance of HUTRAN (e.g., high ionic strength buffers in the presence of detergent). The column is eluted under conditions that disrupt antibody/HUTRAN binding (e.g., a buffer of pH 2 to pH 3, or a high concentration of a chaotrope, such as urea or thiocyanate ion), and HUTRAN is collected.

XIV. Identification of Molecules Which Interact with HUTRAN

HUTRAN, or biologically active fragments thereof, are labeled with $^{125}$I Bolton-Hunter reagent. (See, e.g., Bolton et al. (1973) Biochem. J. 133:529.) Candidate molecules previously arrayed in the wells of a multi-well plate are incubated with the labeled HUTRAN, washed, and any wells with labeled HUTRAN complex are assayed. Data obtained using different concentrations of HUTRAN are used to calculate values for the number, affinity, and association of HUTRAN with the candidate molecules.

Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

TABLE 1

| Protein SEQ ID NO: | Nucleotide SEQ ID NO: | Clone ID | Library | Fragments |
|---|---|---|---|---|
| 1 | 4 | 1815528 | PROSNOT20 | 1815528H1 (PROSNOT20), 2880980F6 (UTRSTUT05), 1815528x12C1 (PROSNOT20), 1815528x17C1 (PROSNOT20), 1819092T6 (PROSNOT20), 269916F1 (HNT2NOT01), 1717401F6 (UCMCNOT02) (SEQ ID NO: 7–13) |
| 2 | 5 | 2150892 | BRAINOT09 | 2150892H1 (BRAINOT09), SAGA00872F1, SAGA01877F1, SAGA01269R1, SAGA02228F1, SAGA01614F1, 301251T6 (TESTNOT04) (SEQ ID NO: 14–20) |
| 3 | 6 | 2525071 | BRAITUT21 | 2525071H1 (BRAITUT21), 1889292H1 (BLADTUT07), 2525071F6 (BRAITUT21), SAEA10009P1, SAEA03283F1, SAEAO1931R1, 1253024T6 (LUNGFET03), 1664573F6 (BRSTNOT09), 1474156T1 (LUNGTUT03) (SEQ ID NO: 21–29) |

TABLE 2

| Seq ID NO: | Amino Acid Residues | Potential Phosphorylation Sites | Potential Glycosylation Sites | Signature Sequences | Identification | Analytical Methods |
|---|---|---|---|---|---|---|
| 1 | 454 | S189 S408 S124 S189 S378 S422 S437 S12 S23 S32 S36 Y338 Y395 | | S277AGKTF (pyridoxal phosphate binding site) M268 through V284 (transmembrane sequence) | glutamine-phenylpyruvate aminotransferase | BLAST BLOCKS PFAM MOTIFS PFAM MOTIFS TM |
| 2 | 425 | T21 S170 S11 T190 S210 | | 5260FSK (pyridoxal phosphate binding site) | kynurenine/alpha-aminoadipate aminotransferase | BLAST MOTIFS |
| 3 | 447 | S286 S85 T127 S330 T355 T71 S191 | N18 N69 N343 N384 | methyltransferase motifs: V27LDVGCGSG (region I) I49YAVE (post-region I) E88QVDIIIS (region II) Y117LKPSGNMFP (region III) L165RGAA (post-region III) M1 through A46 (signal sequence) | arginine methyltransferase | BLAST MOTIFS SPSCAN |

TABLE 3

| Seq ID NO: | Tissue Expression (Fraction of Total) | Diseases or Conditions (Fraction of Total) | Vector |
|---|---|---|---|
| 1 | Reproductive (0.302) Cardiovascular (0.163) Hematopoietic/Immune (0.116) Gastrointestinal (0.093) Nervous (0.070) | Cancer (0.465) Inflammation (0.256) Fetal (0.233) Trauma (0.093) | pINCY |
| 2 | Reproductive (0.429) Nervous (0.214) Developmental (0.143) Gastrointestinal (0.143) | Cancer (0.429) Fetal (0.214) Trauma (0.214) Inflammation (0.1443) | pINCY |
| 3 | Gastrointestinal (0.259) Reproductive (0.241) Developmental (0.111) Nervous (0.111) | Cancer (0.537) Fetal (0.185) Inflammation (0.167) Trauma (0.093) | pINCY |

TABLE 4

| Protein SEQ ID NO: | Clone ID | Library | Library Comment |
|---|---|---|---|
| 1 | 1815528 | PROSNOT20 | PROSNOT20 Library was constructed using RNA isolated from diseased prostate tissue removed from a 65-year-old Caucasian male during a radical prostatectomy. Pathology indicated adenofibromatous hyperplasia. Pathology for the associated tumor tissue indicated an adenocarcinoma. |
| 2 | 2150892 | BRAINOT09 | BRAINOT09 Library was constructed using RNA isolated from brain tissue removed from a Caucasian male fetus who died at 23 weeks' gestation. |
| 3 | 2525071 | BRAITUT21 | BRAITUT21 Library was constructed using RNA isolated from brain tumor tissue removed from the midline frontal lobe of a 61-year-old Caucasian female during excision of a cerebral meningeal lesion. Pathology indicated subfrontal meningothelial meningioma with no atypia. One ethmoid and cerebrovascular disease, senile demential, hyperlipidemia, benign hypertension, atherosclerotic coronary artery disease, congestive heart failure, and breast cancer. |

TABLE 5

| Program/algorithm | Databases | Description | Useful Parameters |
|---|---|---|---|
| ESTs | | | |
| Smith Waterman | GenBank | Local alignment algorithm for homology searching | min length = 49 nt <12% uncalled bases |
| FASTA | GenBank | Fast nucleotide sequence database searching program for UNIX, VMS | |
| BLAST | GenBank | Ultra-fast database searching program for UNIX, VMS C source | Log likelihood for exact matches is $\sim 10^{-25}$ and for homologs $>10^{-8}$ |
| Full Length | | | |
| Phred | | Reads trace data from sequencing runs, makes base calls for assembly of cDNA sequences, produces quality scores | |
| Phrap | | Quality-score based assembly program for shotgun sequences | match >56 score >120 |
| CONSED | | Graphical tool for editing Phrap contigs | |
| GCG Assembly, Motifs, Profilescan, | GenBank PROSITE | Wisconsin Package Programs for the assembly, editing, and characterization of nucleotide sequences | |
| Spscan | | Examines proteins for secretory, signal sequences | >7 strong, 4.5–7 suggestive |
| GENEMARK | | Statistical analysis of nucleotide sequences to identify open reading frame | |
| BLAST | GenBank SwissProt | Ultra-fast database searching program for UNIX, VMS C source | score >1000, P < 1e–5 |
| FASTX | GenBank SwissProt | Fast amino acid sequence database searching program for UNIX, VMS | log likelihood >17 |
| BLIMPS | BLOCKS PRINTS | Weighted matrix analysis for prediction of protein family | >1300 strong, 1000–1300 suggestive, P < 1c–3 |
| PFAM | PROSITE | Analyses sequences 3–60 amino acids long which correspond to highly conserved regions of a protein family | Score >11 strong, 8–10 suggestive |
| HMM | | Probabilistic approaches and modeling of the primary structure of protein families | Score >11 strong, 8–10 suggestive |
| McDNAsis Pro | | Software for sequence analysis | |
| LASERGENE | | Software programs (EditSeq, MegAlign, PrimerSelect, Protean, SeqMan, etc.) for sequence analysis | |

What is claimed is:

1. An isolated and purified polynucleotide encoding a polypeptide comprising an amino acid sequence selected from the group consisting of SEQ ID NO:1, SEQ ID NO:2, and SEQ ID NO:3.

2. An isolated and purified polynucleotide which hybridizes under hybridization conditions of 250 mM NaCl, 25 mM trisodium citrate, 1% SDS, 50% formamide, and 200 μg/ml ssDNA at 42° C., and wash conditions of 15 mM NaCl, 1.5 mM trisodium citrate, and 0.1% SDS at 68° C. to the polynucleotide of claim 1.

3. An isolated and purified polynucleotide which is completely complementary to the polynucleotide of claim 1.

4. An isolated and purified polynucleotide selected from the group consisting of SEQ ID NO:4, SEQ ID NO:5, and SEQ ID NO:6.

5. An isolated and purified polynucleotide which is completely complementary to the polynucleotide of claim 4.

6. An expression vector comprising the polynucleotide of claim 1.

7. A host cell comprising the expression vector of claim 6.

8. A method for producing a polypeptide comprising the amino acid sequence selected from the group consisting of SEQ ID NO:1, SEQ ID NO:2, and SEQ ID NO:3, the method comprising the steps of:

(a) culturing the host cell of claim 7 under conditions suitable for the expression of the polypeptide; and (b) recovering the polypeptide from the host cell culture.

9. A method for detecting a polynucleotide encoding a polypeptide comprising the amino acid sequence selected from the group consisting of SEQ ID NO:1, SEQ ID NO:2, and SEQ ID NO:3, in a biological sample containing nucleic acids, the method comprising the steps of:

(a) hybridizing the polynucleotide of claim 3 under hybridization conditions of 250 mM NaCl, 25 mM trisodium citrate, 1% SDS, 50% formamide, and 200 μg/ml ssDNA at 42° C., to at least one of the nucleic acids in the biological sample, thereby forming a hybridization complex;

(b) subjecting the hybridization complex to wash conditions of 15 mM NaCl, 1.5 mM trisodium citrate, and 0.1% SDS at 68° C.; and (c) detecting the hybridization complex, wherein the presence of the hybridization complex correlates with the presence of the polynucleotide encoding the polypeptide in the biological sample.

10. The method of claim 9 further comprising amplifying the nucleic acids of the biological sample by the polymerase chain reaction prior to the hybridizing step.

* * * * *